(12) United States Patent
Wurzer et al.

(10) Patent No.: US 11,634,683 B2
(45) Date of Patent: Apr. 25, 2023

(54) NON-ENZYMATIC METHOD AND MILLING DEVICE

(71) Applicant: LIPOREGENA GMBH, Breitenfurt bei Wien (AT)

(72) Inventors: Christoph Wurzer, Linz (AT); Eleni Priglinger, Traun (AT); Heinz Redl, Vienna (AT)

(73) Assignee: LIPOREGENA GMBH, Breitenfurt bei Wien (AT)

( * ) Notice: Subject to any disclaimer, the term of this patent is extended or adjusted under 35 U.S.C. 154(b) by 486 days.

(21) Appl. No.: 16/096,327

(22) PCT Filed: Apr. 26, 2017

(86) PCT No.: PCT/EP2017/059934
§ 371 (c)(1),
(2) Date: Oct. 25, 2018

(87) PCT Pub. No.: WO2017/186795
PCT Pub. Date: Nov. 2, 2017

(65) Prior Publication Data
US 2019/0127681 A1    May 2, 2019

(30) Foreign Application Priority Data

Apr. 26, 2016   (EP) ..................... 16167009

(51) Int. Cl.
*C12N 5/077*   (2010.01)
*C12M 1/33*    (2006.01)

(52) U.S. Cl.
CPC .......... *C12M 45/02* (2013.01); *C12N 5/0653* (2013.01); *A61M 2202/08* (2013.01); *A61M 2205/103* (2013.01)

(58) Field of Classification Search
CPC .............. C12M 45/02; A61M 2202/08; A61M 2205/103; A61M 2205/10; C12N 5/0653; C12N 5/0652; C12N 5/0602
See application file for complete search history.

(56) References Cited

U.S. PATENT DOCUMENTS

| 4,028,190 A | 6/1977 | McAleer et al. |
| 2004/0067582 A1* | 4/2004 | Wolfinbarger, Jr. ........... A61L 27/3683 |
| | | 435/366 |

(Continued)

FOREIGN PATENT DOCUMENTS

| CN | 103038333 | 4/2013 |
| CN | 103153376 | 6/2013 |

(Continued)

OTHER PUBLICATIONS

Office action of Applicant's counterpart Japanese Application No. 2018-557018, dated Oct. 27, 2020, and English language translation of the Office action.

(Continued)

*Primary Examiner* — Samuel P Siefke
*Assistant Examiner* — Tingchen Shi
(74) *Attorney, Agent, or Firm* — Greenblum & Bernstein, P.L.C.

(57) ABSTRACT

Non-enzymatic method and milling device for preparing therapeutic cells from adipose tissue comprising: continuously feeding the adipose tissue to the milling device (2); mechanically separating the cells or cell aggregates from adipose tissue moving through the milling device (2) by means of a multiplicity of blades (19) of a rotor (10), wherein the blades (19) are arranged in a spaced arrangement with respect to the overall direction of flow and the blades (19) are moving about an axis of rotation (18), wherein the axis of rotation (18) is provided essentially (Continued)

parallel to said overall direction of flow; continuously withdrawing the processed tissue comprising the separated cells from the milling device (2).

20 Claims, 43 Drawing Sheets

(56) References Cited

U.S. PATENT DOCUMENTS

| | | | | |
|---|---|---|---|---|
| 2009/0270896 | A1* | 10/2009 | Sullivan | A61B 17/00234 606/170 |
| 2010/0112696 | A1* | 5/2010 | Min | C12M 45/09 435/378 |
| 2010/0285521 | A1* | 11/2010 | Vossman | C12M 45/05 435/34 |
| 2012/0052559 | A1* | 3/2012 | Haraguchi | G01N 1/286 435/286.1 |
| 2013/0164731 | A1* | 6/2013 | Cimino | C12M 47/04 435/1.1 |
| 2014/0193852 | A9 | 7/2014 | Vossman et al. | |
| 2015/0037436 | A1* | 2/2015 | Huang | A61L 27/3604 424/574 |
| 2015/0118752 | A1* | 4/2015 | Cimino | C12M 47/04 422/534 |
| 2016/0030486 | A1 | 2/2016 | Cimino et al. | |
| 2016/0069781 | A1* | 3/2016 | Middlebrook | C12M 45/02 241/38 |

FOREIGN PATENT DOCUMENTS

| | | |
|---|---|---|
| EP | 2 423 301 | 2/2012 |
| WO | 2010/129817 | 11/2010 |
| WO | 2012/006587 | 1/2012 |
| WO | 2015/035221 | 3/2015 |
| WO | 2015/163010 | 10/2015 |
| WO | WO-2015163010 A1 * 10/2015 | ............. B02C 18/06 |

OTHER PUBLICATIONS

Office Action issued in China Counterpart Patent Appl. No. 201780036236.2, dated Jun. 23, 2021, in English.

* cited by examiner

Invention

Shaking

Cutting

Collagenase 0.2 U/ml

Adipogenesis (Oil Red O)

NON-ENZYMATIC METHOD AND MILLING DEVICE

The present invention concerns a non-enzymatic method and a corresponding milling device for preparing therapeutic cells from adipose tissue as well as a processing device for performing said method and a set provided for liposuction applications of said method and device. The milling device comprises a casing having an inlet and an outlet and defining an operating volume and a rotor received within the operating volume and pivotable with respect to the casing around an axis of rotation.

Human adipose tissue is an attractive and abundantly available source of adult stem cells applicable in regenerative medicine and tissue engineering. The adipose tissue and the derived stromal vascular fraction (SVF) and the adipose derived stromal/stem cells (ASC) contained therein have been successfully used in clinical studies and clinical trials for treating soft tissue defects, bone defects, gastrointestinal lesions, immune disorders, neurological injuries and cardiovascular diseases.

The addition of therapeutic cells, such as contained in the SVF, in cell assisted lipotransfer (CAL) can reduce postoperative atrophy in breast augmentation, increases fat graft survival and leads to neo-vascularization inside the grafts. The interaction between cells of the grafted adipose tissue and cells of the surrounding tissue triggers repair mechanisms by releasing cytokines and growth factors.

Prerequisite for the translation into clinics is the production of adipose tissue-derived cells under good manufacturing practice. A number of companies developed systems aiming for a closed, sterile, safe and reproducible cell isolation process limiting donor variations, risk for contamination and unpredictability of the cell material. However, many of these systems are based on enzymatic digestion with collagenase.

WO 2015/035221 A1 (Cimino, W. W., et al., Tissue processing apparatus and method for processing adipose tissue. 2015, WO 2015035221 A1) and the earlier WO 2012/006587 A2 (from the same inventors) both describe a method for processing adipose tissue in a portable apparatus for cell preparation. The container of the apparatus is separated by a filter into a tissue retention volume and a filtrate volume. A rotatable mixer is provided in the tissue retention volume and connected to a hand-manipulable handle for operating the mixer. The separation of cells is achieved by digesting the tissue inside the container by means of an enzyme-containing digestion medium during a retention time following a wash cycle. Hence the method and device described in WO 2015/035221 A1 (Cimino, W. W., et al. 2015 as cited above) and WO 2012/006587 A2 are limited to batch processing of tissue. The rotatable mixer in both instances achieves only mixing of tissue and digestion medium; a method or device for mechanical separation of cells is not disclosed in either of the two documents.

The device and method described in US 2014/0193852 A9 (Vossman, E., et al., Adipose tissue collection and pre-processing devices for use in liposuction procedure. 2014, US 20140193852 A9) make use of a shredding and separating device for pre-processing of adipose tissue by extracting fibrous material from a tissue sample. The shredding and separating device consists of a basket forming a retention volume for fibrous tissue components, whereas an intermediate cell product composition may pass through a screen at the bottom of the basket and thus avoid shredding by a set of rotatable blades included in the basket. The non-fibrous sample passing through the screen is then washed, centrifuged and digested by adding a digestion enzyme such as collagenase. Hence the device and method disclosed in US 2014/0193852 A9 (Vossman, E., et al. 2014 as cited above) is only used for pre-processing the adipose tissue and it is only by means of said digestion that a liberated cell suspension is obtained.

The use of enzymes such as collagenase complicates regulatory authorization regarding safety and efficacy, is expensive, which is reflected in the cost of cell products, and may have negative impacts on cell potency and efficacy. Therefore, several non-enzymatic adipose tissue-derived cell isolation methods have been developed and transferred into closed devices. However, each method or system have different advantages and disadvantages and is under continuous development and optimization (see Oberbauer, E., et al., Enzymatic and non-enzymatic isolation systems for adipose tissue-derived cells: current state of the art. Cell Regen (Lond), 2015. 4: p. 7.).

An object of the present invention is to provide a non-enzymatic method and device to enrich adipose tissue with therapeutic cells. The efficiency of the method in terms of processing duration and throughput and the quality of the obtained cell material should be at least comparable to existing methods.

The method according to the present invention comprises:
continuously feeding the adipose tissue to a milling device;
mechanically separating the cells or cell aggregates from adipose tissue moving through the milling device by means of a multiplicity of blades, wherein the blades are arranged in a spaced arrangement with respect to the overall direction of flow and the blades are moving about an axis of rotation, wherein the axis of rotation is provided essentially parallel to said overall direction of flow;
continuously withdrawing the processed tissue comprising the separated cells from the milling device.

In operation, there is a continuous flow of adipose tissue into the milling device and out of the milling device. Consequently, the method provides continuous controlled processing of adipose tissue inside the milling device, i.e. without the need of collecting or retaining the unprocessed tissue in separate batches prior to processing. During operation there is an essentially constant flow rate of feed and resulting processed material through the milling device.

The present method is preferably conducted as a process for homogenizing liposuction material (comprising adipose tissue according to the present invention). The cell aggregates obtained by the present method (from e.g. the liposuction material) are preferably referred to as "microtissue". Such microtissues are homogenized tissue fragments, which maintain the cellular components within their natural microenvironment.

Correspondingly the milling device as defined in the outset as having
a casing having an inlet and an outlet and defining an operating volume and
a rotor received within the operating volume and pivotable with respect to the case around an axis of rotation,
if further defined according to the present invention in that
the rotor comprises at least eight rows of blades in a spaced arrangement with respect to the axis of rotation of the rotor and in that
the inlet and the outlet are offset in a direction parallel to the axis of rotation of the rotor.

The arrangement of the inlet and outlet with respect to the rotor is such that a flow of material between the inlet and the outlet has an overall direction (i.e. average or mean direction) that is essentially parallel to the axis of rotation of the rotor. The material being processed in the milling device is essentially moved along an elongate shaft of the rotor. The blades or paddles of the rotor are preferably arranged along and around said elongate shaft. In operation of the device the blades are rotated normally to the length of the shaft. In order to minimize any dead volume within the casing, the inlet and outlet are preferably arranged at opposite ends of the rotor, essentially close to the first and last blade row respectively in a direction of flow.

By means of the above method and device the present invention thus provides a closed and sterile, non-enzymatic means for mild homogenization of adipose tissue and subsequently enrichment of therapeutic cells for autologous clinical applications such as tissue reconstruction, repair or replacement. Without the need of enzyme digestion or further tissue processing it presents a safe method and device for performing the same, with a very high throughput rate within a short processing time. The possibility to be used in a closed system improves sterility without air contamination, which is a major criterion for production of cell therapeutics.

Thus the present method and device when used for cell enrichment are able to generate therapeutic cells of high quality with defined properties for direct clinical application. It has been found that the cells obtained by the present non-enzymatic method possess higher intra- and extracellular ATP and stronger adipogenic, osteogenic and chondrogenic differentiation potential compared to cells isolated by enzymatic and known non-enzymatic isolation methods. Cells derived from the present non-enzymatic method have the potential to form tube-like structures indicating vasculogenesis. Furthermore, the present method affected the freshly isolated and adherent cell composition regarding specific subpopulations, which may be important for neovascularization and differentiation such as endothelial progenitor cells (CD45-/CD31+/CD34+), pericyte like-cells (CD45-/CD31-/CD146+), and supra-adventitial ASC (CD45-/CD31-/CD146-/CD34+) (James, A. W., et al., An abundant perivascular source of stem cells for bone tissue engineering. Stem Cells Transl Med, 2012. 1(9): p. 673-84; Hager, G., et al., Three specific antigens to isolate endothelial progenitor cells from human liposuction material. Cytotherapy, 2013. 15(11): p. 1426-35; Holnthoner, W., et al., Adipose-derived stem cells induce vascular tube formation of outgrowth endothelial cells in a fibrin matrix. J Tissue Eng Regen Med, 2015. 9(2): p. 127-36).

Advantageously, the operating volume defined by the casing corresponds to the solid of revolution created by a line connecting the radii of the blades (i.e. the radius of the tip of the longest blade of each row) of each subsequent row of the rotor rotated around the axis of rotation of the rotor. In other words, the operating volume corresponds to a reference volume consisting of the disks swept by the blades during one turn of the rotor and the cylindrical or conical space between two subsequent such disks. For practical reasons, e.g. to reduce contact between the blades and the inner wall of the casing, the operating volume can be 20%, preferably 10%, in particular 5% larger than said reference volume. The shape of the operating volume defined above is such that the dead volume inside the milling device is minimized while keeping the flow resistance low and essentially defined by the blades of the rotor inside the operating volume.

In a preferred configuration of the present milling device, the rotor comprises between 20 and 80 rows of blades. A lower number of blade rows decreases the processing efficacy significantly and unnecessarily reduces the yield of separated cells. A higher number of blade rows increases the operating volume and thus also the amount of tissue remaining in the device once all feed material has been consumed, without significantly increasing the processing efficacy and the yield of separated cells. Furthermore, a longer contact of the tissue and the device may promote potentially more cell damage.

Preferably at least eight of the rows of blades each comprise two, three or four blades arranged circumferentially with respect to the axis of rotation of the rotor. The number of blades per row determines the working surface acting transversely on the tissue being processed. On the other hand, too many blades per row complicate the fabrication of the device and decrease the reliability with respect to damages as well as with respect to occlusion during operation.

It has been found most effective, that the blades of at least one row are formed by flat plate-like elements. Moreover the length and width of each blade may preferably be in the range of 1 to 50 mm. Regarding the orientation of the blades, it is advantageous when for at least some of the rows, preferably between four and 70 rows, the axis of rotation of the rotor is essentially perpendicular to the midplane of the blades. Also for at least some of the rows, preferably between three and 20 rows, the axis of rotation of the rotor may be arranged essentially parallel to the midplane of the blades. Preferably a mixed configuration of both blade arrangements is used within a single device. The term "midplane" refers to the mid-surface plane of the flat plate-like blades. Thus the midplane is the plane in which the planar dimensions of the plate-like elements are defined. According to the above preferred properties of the rotor, the blades of the present device can be arranged in two different orientations, for instance in two groups of different orientations. One group of blades, e.g. an upstream group, may be arranged having midplanes parallel to the axis of rotation. The blades therefore essentially provide circular propulsion of the tissue when it moves along this group of blades. The second group of blades, e.g. a downstream group, may be arranged having midplanes transverse to the axis of rotation. The blades of this group therefore act on the tissue with their narrow edge, thus producing a cutting effect on the cell structures passing this group of blades.

In order to achieve a relatively low flow resistance within the operating volume, it is preferred that at least some of the rows have an equal number of blades, wherein the blades are arranged in columns parallel to the axis of rotation of the rotor.

Advantageously, the flow rate through the milling device in operation is at least 100 ml/min, preferably at least 200 ml/min. The flow rate determines the time the tissue being processed remains within the operating volume and also determines the speed of flow of the material hitting the blades. It is thus advantageous to adapt the flow rate to the shape and movement of the blades and to the desired processing time.

In order to provide for homogeneous movement over the entire cross-section of the device, the rotor may comprise a propeller, preferably formed by at least one row of blades configured as propeller blades. Such propeller blades may be arranged with their midplanes inclines with respect to the plane of movement (which is normal to the axis of rotation). In this instance the device acts as an axial-flow pump. Where a relatively low and accurate flow rate is desired, the rotor may additionally or alternatively comprise a screw propeller.

Accordingly, the present method may comprise: pumping the tissue through the milling device, preferably by means of the rotation of the blades. The pumping refers to a pumping pressure which drives or pushes the tissue through the device and effectively leads to a forward movement of the tissue within the device, parallel to the axis of rotation. This forward movement pushes the tissue against the blades normal to the movement of the blades and thus participates in the mechanical separation of cells or cell aggregates from adipose tissue.

Advantageously, at least one of the blades comprises two or more radially spaced teeth, preferably extending parallel to the axis of rotation. The teeth may also be inclined by an angle between 0 and 80° with respect to a plane parallel to the axis of rotation of the rotor. By means of said radially spaced teeth, a temporary retention of fibrous tissue between the teeth can be achieved. This increases the processing time of said fibrous tissue relative to other, non-fibrous tissue and thus improves separation performance with respect to the fibrous tissue without decreasing the throughput for non-fibrous tissue.

In a preferred embodiment at least a section of the operating volume has a tapered shape with a cross-section decreasing in a direction from the inlet to the outlet. The section or tapered section here refers to a part of the overall length of the operating volume parallel to the axis of rotation of the rotor. The tapered shape is preferably frustoconical with the symmetry axis of the cone being the axis of rotation of the rotor. The tapered section is preferably located adjacent to the inlet of the casing, wherein a subsequent cylindrical section of the operating volume follows between the tapered section and the outlet of the casing.

The casing is preferably formed from one or more components connected to each other in a fixed arrangement. In particular, the casing has no moving parts and the components of the casing are welded or glued together after insertion of the rotor into the operating volume formed by the casing. Due to the absence of moving parts in the casing, deposits of tissue material in gaps or joints of the casing can be effectively avoided. This helps to avoid unpredictable dead zones within the casing and also to facilitate handling and cleaning of the device.

The processing efficiency of the present device and the efficacy of the mechanical separation of cells are basically a function of the length and cross section of the operating volume in which the blades are being rotated. It has turned out that the preferred ratio of the average cross section of the operating volume transversely to the axis of rotation of the rotor with respect to the overall length of the operating volume parallel to the axis of rotation of the rotor is between 0.02 and 0.5. This means that the operating volume is at least twice as long as it is wide and up to 50 times as long as it is wide (on average). Higher lengths would lead to significant dead volume without significantly improving the separation result.

In terms of absolute numbers, which are tailored to the preferred application in processing tissue removed by liposuction, the length of the operating volume parallel to the axis of rotation of the rotor is below 500 mm.

In order to achieve highest possible standards in terms of cleanliness and sterility, the milling device may be provided as a milling cartridge. In other words, the milling device can be provided as a single use device. In this instance the device is basically used for processing the tissue of a single patient or removed from a single patient during one treatment session. Once the entire tissue volume associated with a given treatment session has been processed, the milling cartridge is discarded.

The milling device employed within the present method preferably is a milling device according to one of the above-discussed more detailed structural variants and embodiments.

The invention further concerns the overall use of the present milling device as part of a processing device for preparing therapeutic cells or microtissue from adipose tissue (e.g. by homogenizing liposuction material), said processing device comprising: at least one milling device as defined above, and a drive connected to the rotor of the milling device via a driveshaft, wherein the drive preferably is formed by a motor. I.e. the processing device effectively complements the milling device with a drive for driving the rotor and thus automatically performing the desired processing and separation.

Where such a processing device is foreseen, the drive may preferably be connected to the rotor of the milling device by a magnetic coupling. The magnetic coupling has the advantage of applying the driving torque to the rotor without the need for moving parts of the casing. Also the magnetic coupling naturally limits the maximum transmitted torque and thus avoids damage of the rotor. It also helps to avoid cell damage due to unintended peaks of the torque applied by the drive (e.g. during start and stop of the drive).

An improved processing efficacy has been observed when the present method comprises: controlling the speed of rotation to a predefined constant speed, preferably between 700-1100 rpm. The use of a predefined constant speed is possible due to the continuous flow and essentially constant flow rate. The actual speed of rotation can be chosen as a function of the length and maximum radius of the rotor blades. With regard to the processing device as defined above, the drive may correspondingly be connected to a controller for controlling the rotation speed to a constant speed, preferably between 700-1100 rpm.

In order to achieve the desired continuous flow and processing within the milling device, the method may comprise: continuously withdrawing the processed tissue comprising the separated cells from the milling device by applying a suction to an outlet or pressure to an inlet of the milling device and/or by applying a pressure to an inlet of the milling device.

Moreover, the milling device of the processing device may be formed by a milling cartridge as defined above, which is provided as an expendable part of the processing device. In this instance, the milling cartridge can be discarded after every use, e.g. after every treatment session including the processing of adipose tissue. The used milling cartridge can be released and decoupled from the drive of the processing device and replaced with a new, unused milling cartridge.

In a preferred application of the present method, the method comprises: receiving the adipose tissue through a hose connected to a cannula, i.e. a needle used in liposuction, before continuously feeding the adipose tissue to the milling device. In this preferred use-case, the milling device is used for processing adipose tissue removed during liposuction, i.e. for processing the "lipoaspirate".

A further preferred embodiment of the present invention with regard to this application is a set for liposuction applications comprising: a milling device (or milling cartridge) as defined above, and a cannula, which is connected to the inlet of the milling device. The set has the advantage, that a ready-to-use and reliable connection between the cannula and the milling device can be provided. Existing liposuction equipment (pump, collection vessel, etc.) can be connected to the milling device instead of directly to the cannula using the same interface. Thus no additional equipment is needed.

In the following, preferred embodiments of the method, the milling device, the processing device and the set according to the invention will be defined, as well as preferred combinations thereof:

1. Non-enzymatic method for preparing therapeutic cells from adipose tissue comprising:
   continuously feeding the adipose tissue to a milling device;
   mechanically separating the cells or cell aggregates from adipose tissue moving through the milling device by means of a multiplicity of blades, wherein the blades are arranged in a spaced arrangement with respect to the overall direction of flow and the blades are moving about an axis of rotation, wherein the axis of rotation is provided essentially parallel to said overall direction of flow;
   continuously withdrawing the processed tissue comprising the separated cells from the milling device.

2. Method according to embodiment 1, wherein the flow rate through the milling device in operation is at least 100 ml/min, preferably at least 200 ml/min.

3. Method according to embodiment 1 or 2, comprising: controlling the speed of rotation to a predefined constant speed, preferably between 700-1100 rpm.

4. Method according to one of the preceding embodiments, comprising: pumping the tissue through the milling device, preferably by means of the rotation of the blades.

5. Method according to one of the preceding embodiments, comprising: continuously withdrawing the processed tissue comprising the cell aggregates separated cells from the milling device by applying a suction to an outlet of the milling device.

6. Method according to one of the preceding embodiments, comprising: receiving the adipose tissue through a hose connected to a cannula before continuously feeding the adipose tissue to the milling device.

7. Method according to one of the preceding embodiments, wherein the milling device is a milling device according to one of embodiments 9 to 23.

8. Milling device for preparing therapeutic cells from adipose tissue comprising:
   a casing having an inlet and an outlet and defining an operating volume and
   a rotor received within the operating volume and pivotable with respect to the casing around an axis of rotation, characterized in that
   the rotor comprises at least eight rows of blades in a spaced arrangement with respect to the axis of rotation of the rotor and in that
   the inlet and the outlet are offset in a direction parallel to the axis of rotation of the rotor.

9. Milling device according to embodiment 8, characterized in that the operating volume defined by the casing corresponds to the solid of revolution created by a line connecting the radii of the blades of each subsequent row of the rotor rotated around the axis of rotation of the rotor.

10. Milling device according to embodiment 8 or 9, characterized in that the rotor comprises between 20 and 80 rows of blades.

11. Milling device according to one of embodiments 8 to 10, characterized in that at least eight of the rows of blades each comprise two, three or four blades arranged circumferentially with respect to the axis of rotation of the rotor.

12. Milling device according to one of embodiments 8 to 11, characterized in that the blades of at least one row are formed by flat plate-like elements.

13. Milling device according to embodiment 12, characterized in that the length and width of each blade is in the range of 1 to 50 mm.

14. Milling device according to embodiment 12 or 13, characterized in that for at least some of the rows, preferably between four and 70 rows, the axis of rotation of the rotor is essentially perpendicular to the midplane of the blades.

15. Milling device according to one of embodiments 12 to 14, characterized in that for at least some of the rows, preferably between three and 20 rows, the axis of rotation of the rotor is essentially parallel to the midplane of the blades.

16. Milling device according to one of embodiments 8 to 15, characterized in that at least some of the rows have an equal number of blades, wherein the blades are arranged in columns parallel to the axis of rotation of the rotor.

17. Milling device according to one of embodiments 8 to 16, characterized in that the rotor comprises a propeller, preferably formed by at least one row of blades configured as propeller blades.

18. Milling device according to one of embodiments 8 to 17, characterized in that at least one of the blades comprises two or more radially spaced teeth, preferably extending parallel to the axis of rotation.

19. Milling device according to one of embodiments 8 to 18, characterized in that at least a section of the operating volume has a tapered shape with a cross-section decreasing in a direction from the inlet to the outlet.

20. Milling device according to one of embodiments 8 to 19, characterized in that the casing is formed from one or more components connected to each other in a fixed arrangement.

21. Milling device according to one of embodiments 8 to 20, characterized in that the ratio of the average cross section of the operating volume transversely to the axis of rotation of the rotor with respect to the overall length of the operating volume parallel to the axis of rotation of the rotor is between 0.02 and 0.5.

22. Milling device according to one of embodiments 8 to 21, characterized in that the length of the operating volume parallel to the axis of rotation of the rotor is below 500 mm.

23. Milling device according to one of embodiments 8 to 22, characterized in that the milling device is provided as a milling cartridge.

24. Processing device for preparing therapeutic cells from adipose tissue comprising:
   at least one milling device according to one of embodiments 8 to 23, and
   a drive connected to the rotor of the milling device via a driveshaft, wherein the drive preferably is formed by a motor.

25. Processing device according to embodiment 24, characterized in that the drive is connected to the rotor of the milling device by a magnetic coupling.

26. Processing device according to embodiment 24 or 25, characterized in that the drive is connected to a controller for controlling the rotation speed, preferably to a constant speed, in particular to a constant speed between 700-1100 rpm.

27. Processing device according to one of embodiments 24 to 26, characterized in that the milling device is formed by a milling cartridge according to embodiment 22, which is provided as an expendable part of the processing device.

28. Set for liposuction applications comprising:
   a milling device according to one of embodiments 8 to 23, and
   a cannula, which is connected to the inlet of the milling device by tubing which preferably accommodates also a roller pump.

The invention will be defined in more detail below by means of preferred exemplary embodiments, to which it is not to be limited to, however, and with reference to the drawings. In detail:

FIG. 1 schematically shows an exploded view of a processing device comprising a milling device according to the present invention;

FIG. 2 schematically shows the rotor of the milling device shown in FIG. 1;

Figure 9:
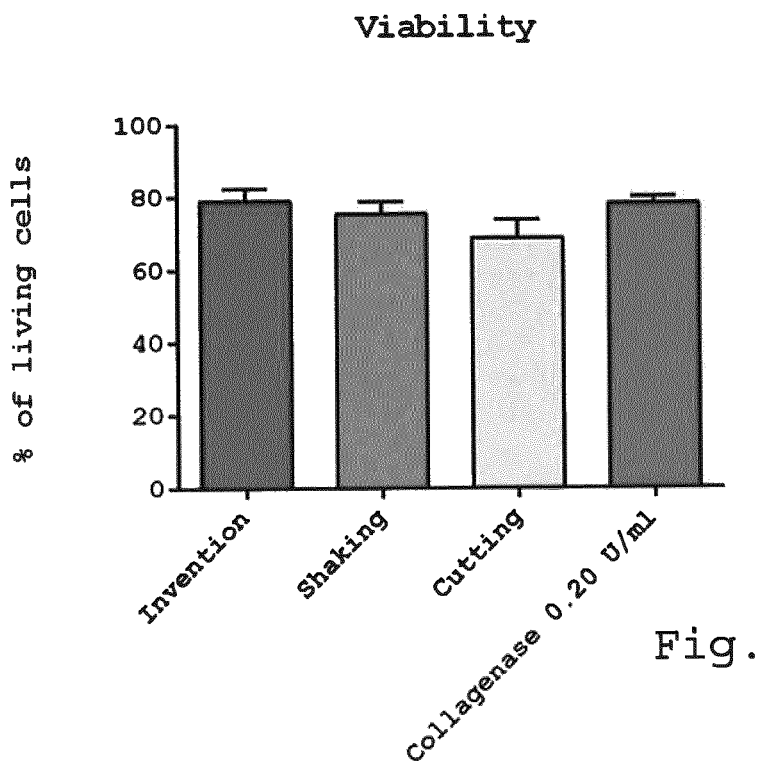
Figure 10A:
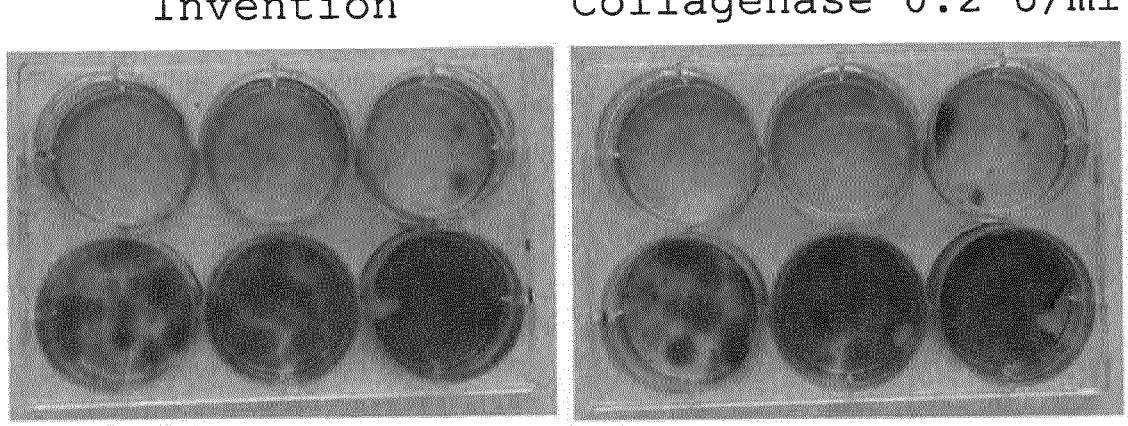
Figure 10B:
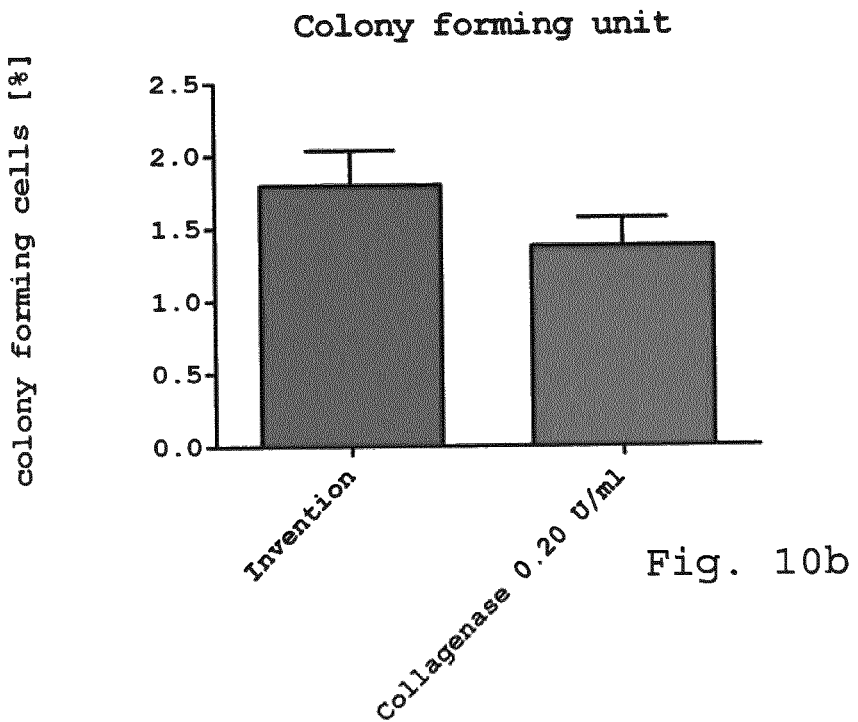
Figure 11:
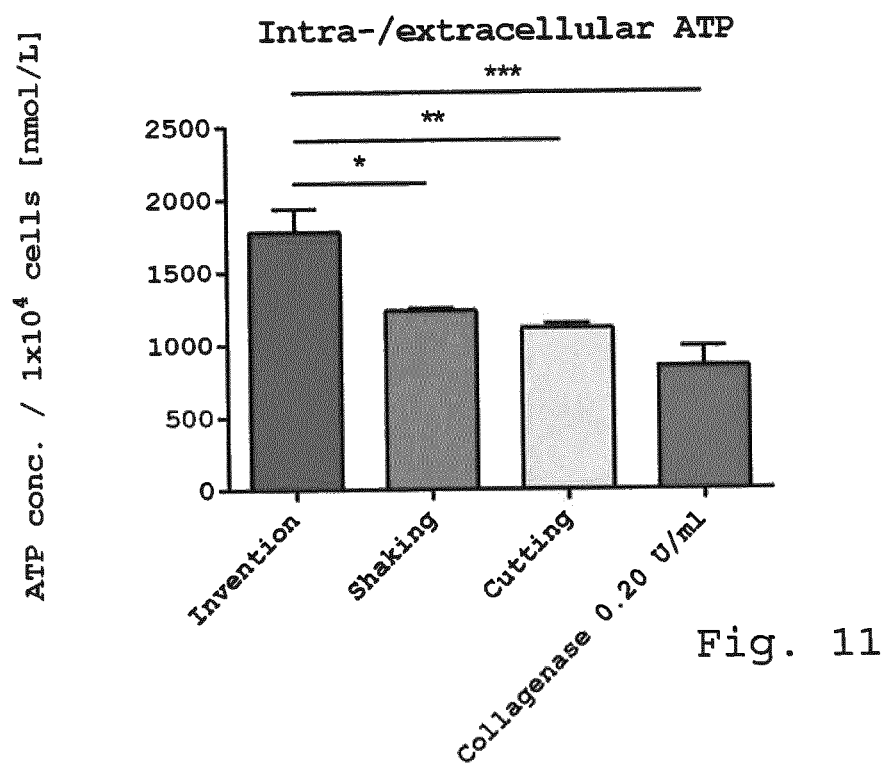
Figure 12A:
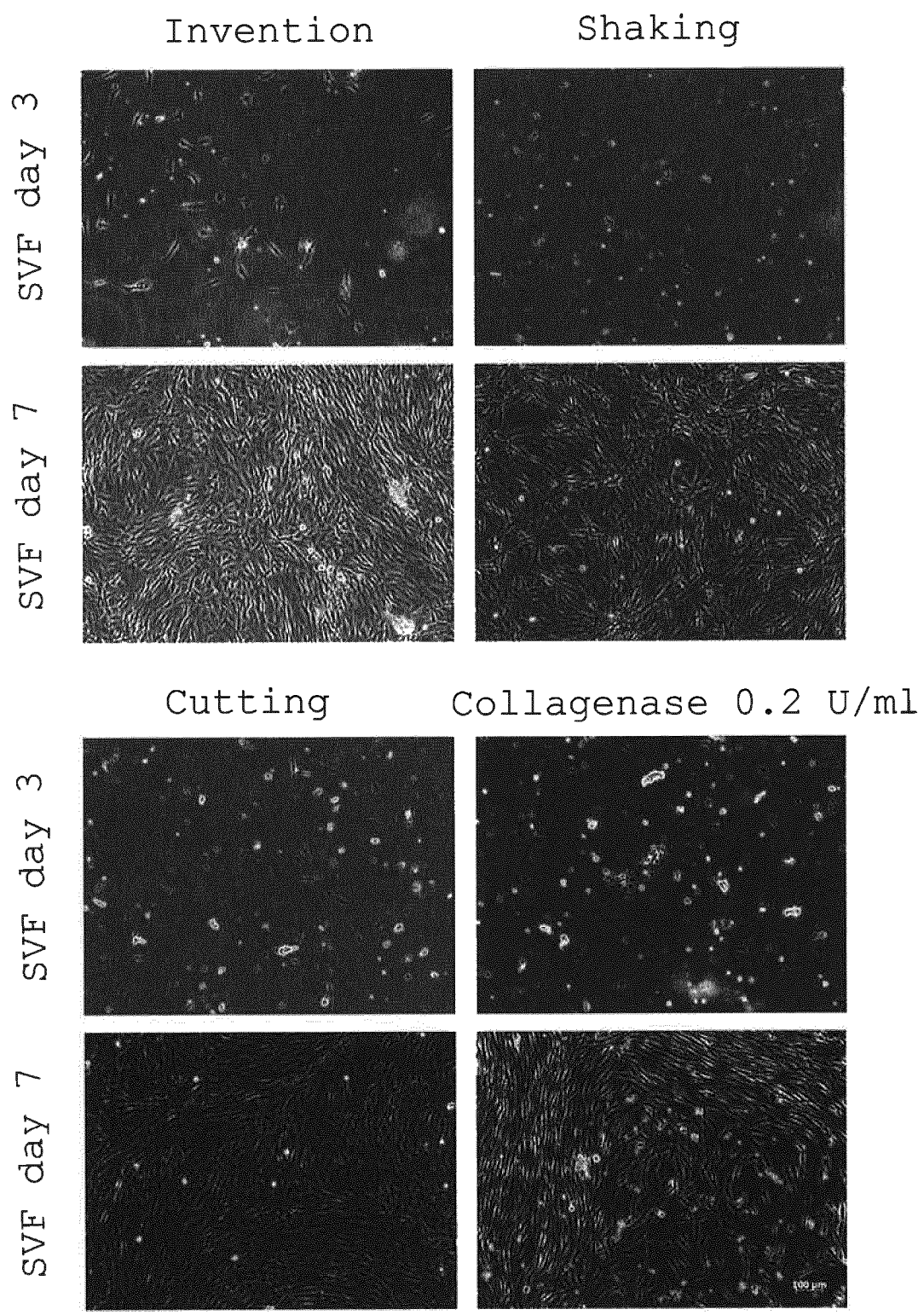
Figure 12B:
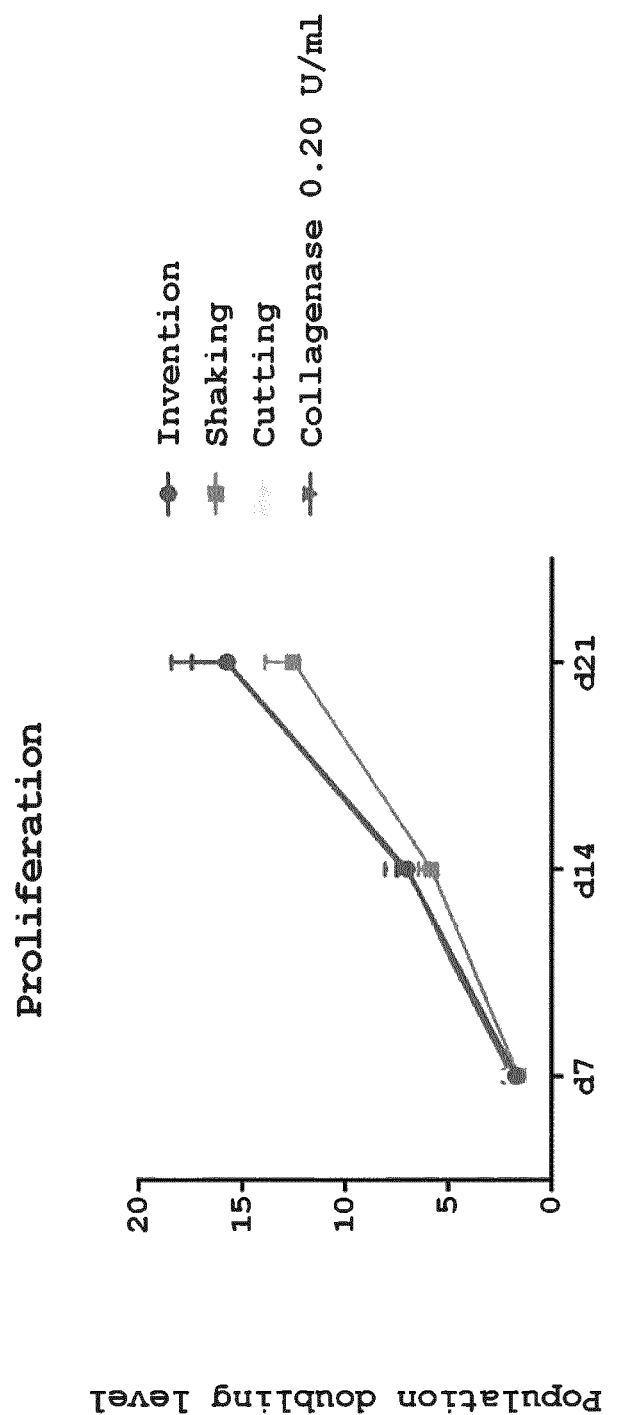
Figure 13A:
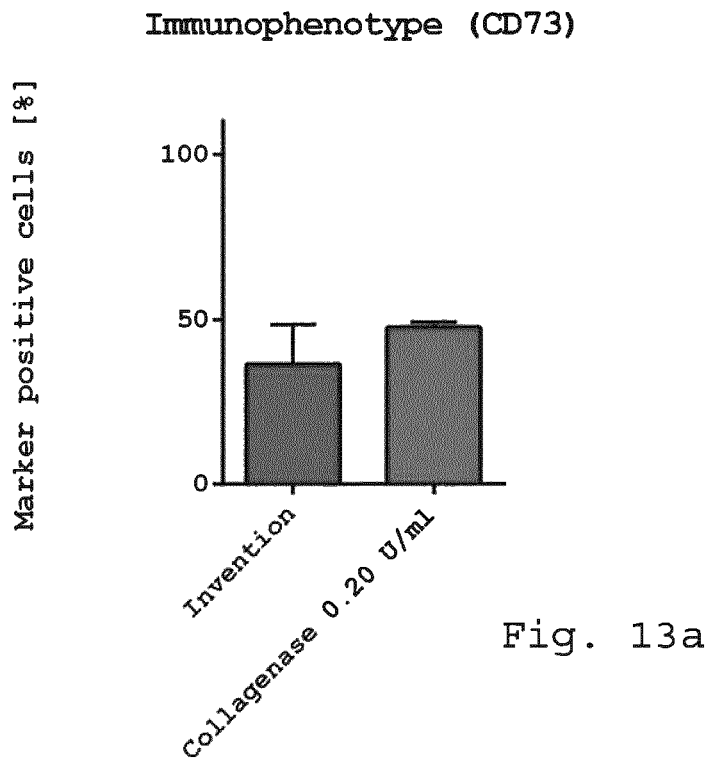
Figure 13B:
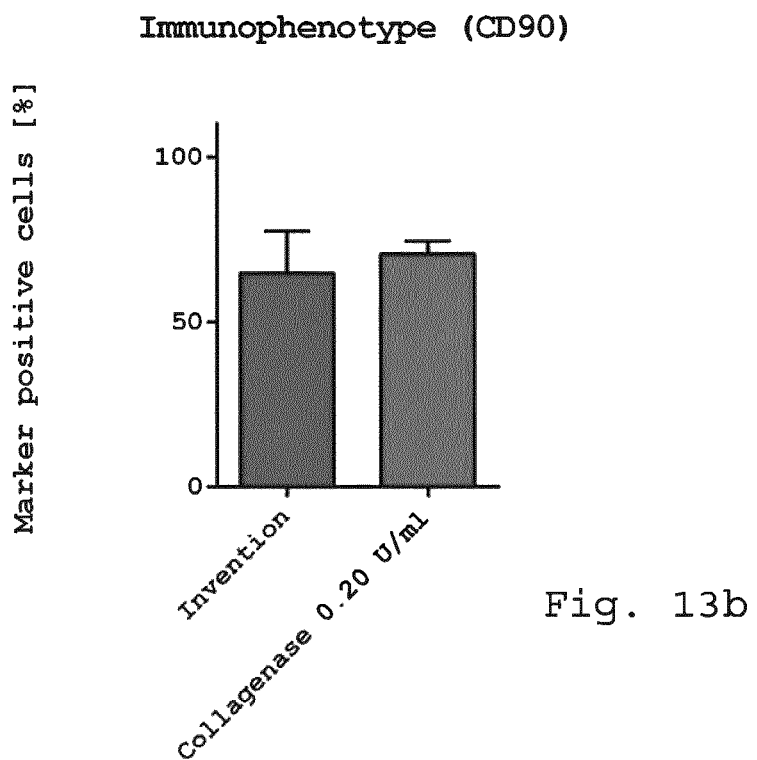
Figure 13C:
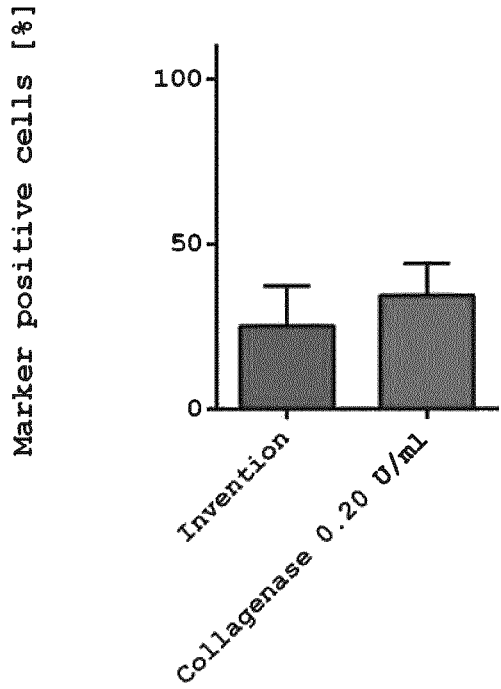
Figure 13D:
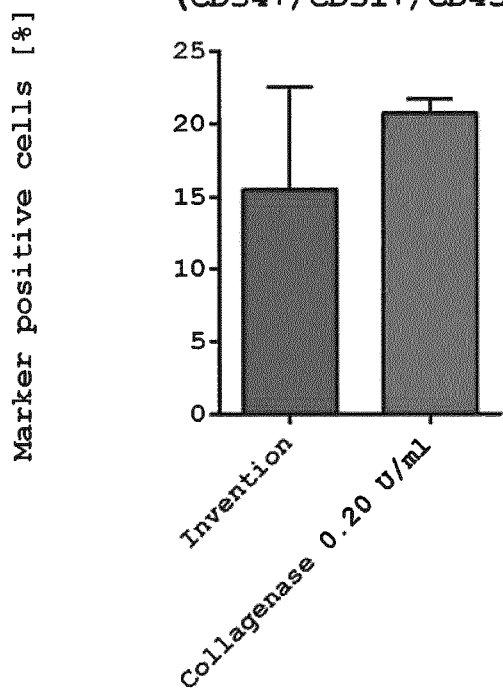
Figure 13E:
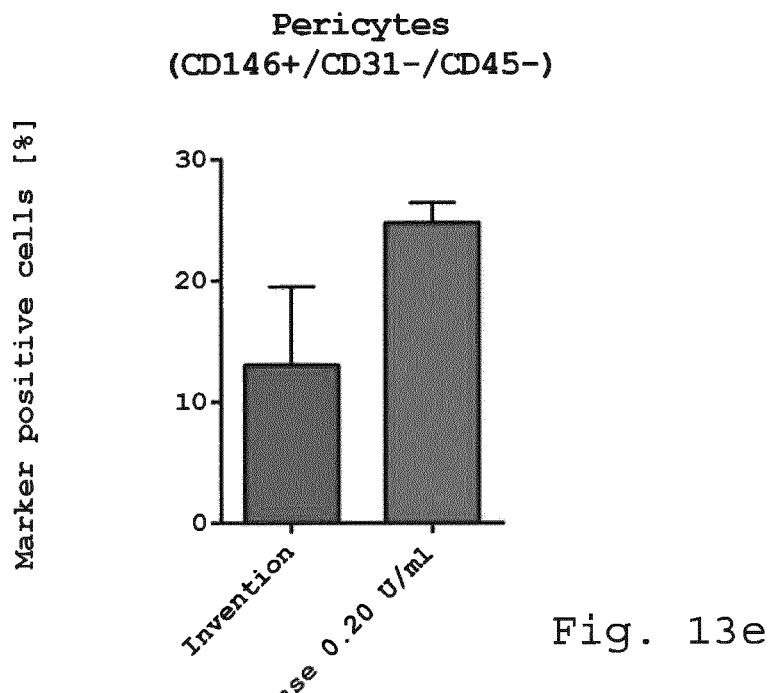
Figure 13F:
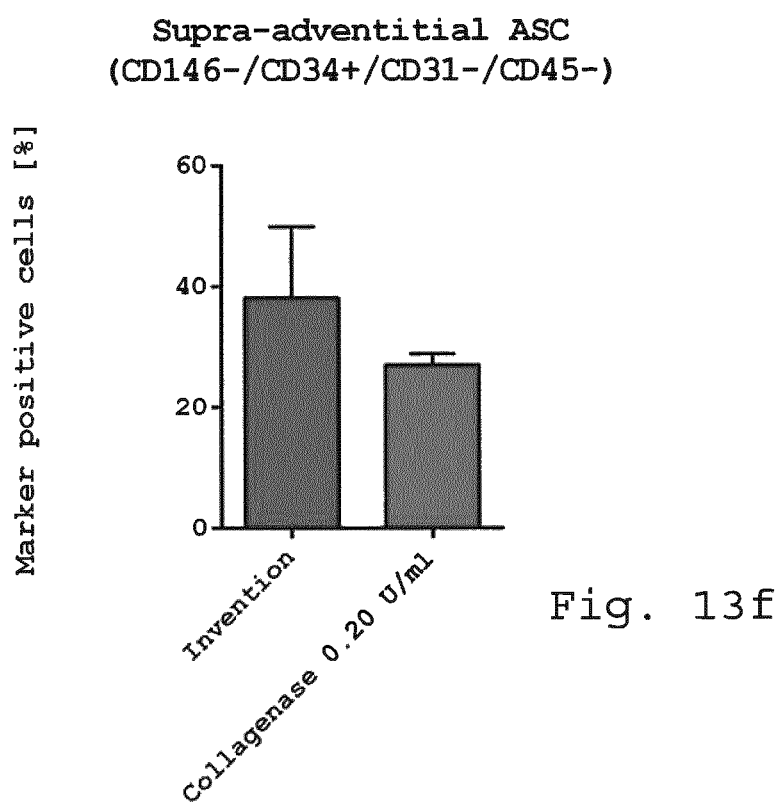
Figure 14A:
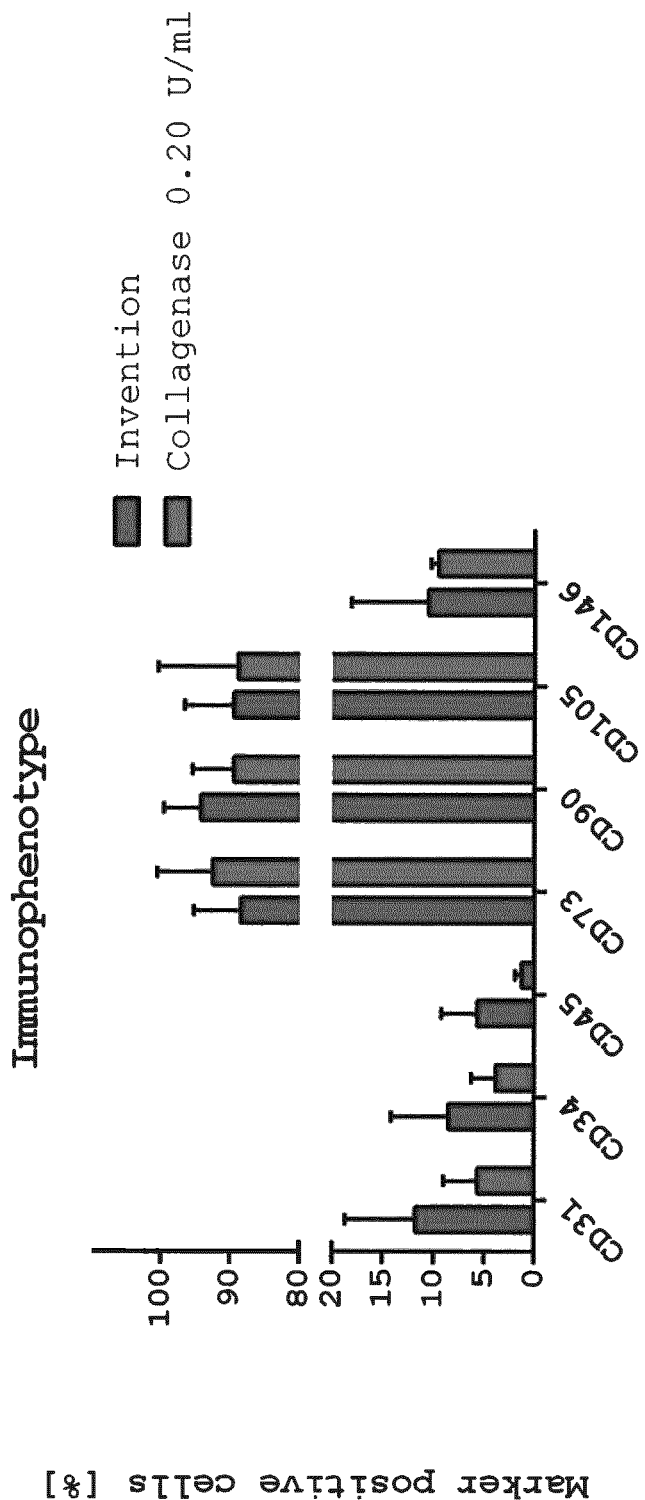
Figure 14B:
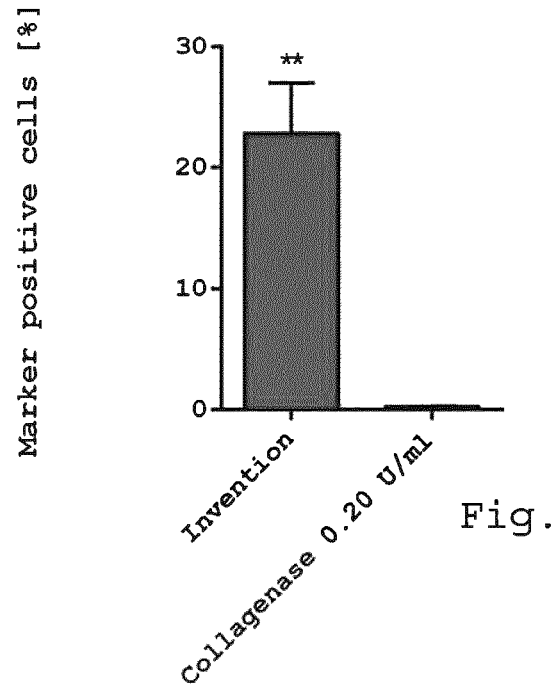
Figure 14C:
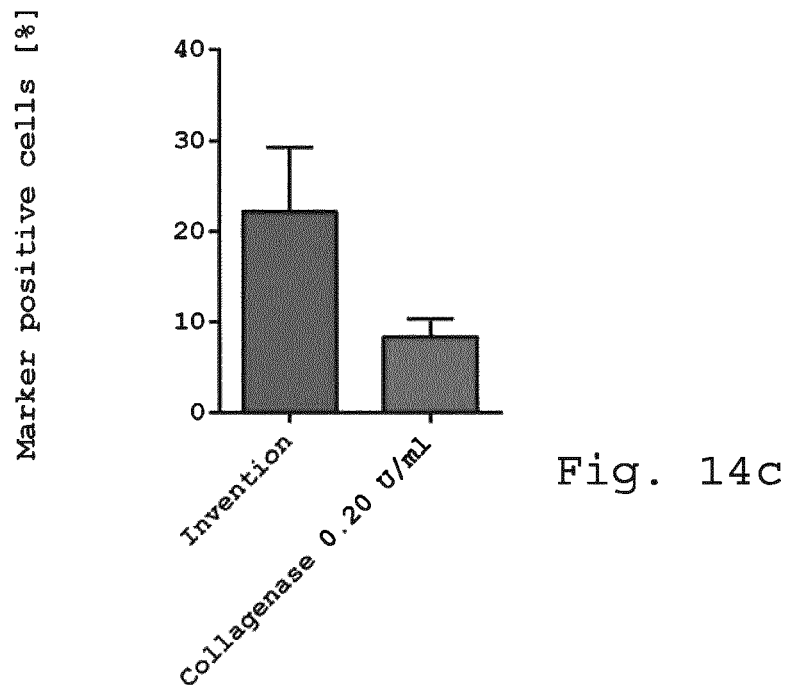
Figure 14D:
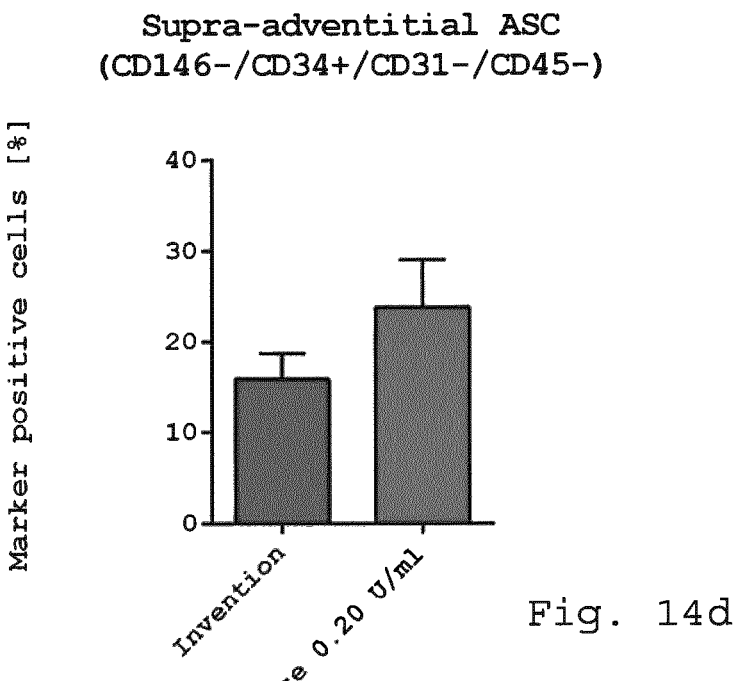
Figure 15:
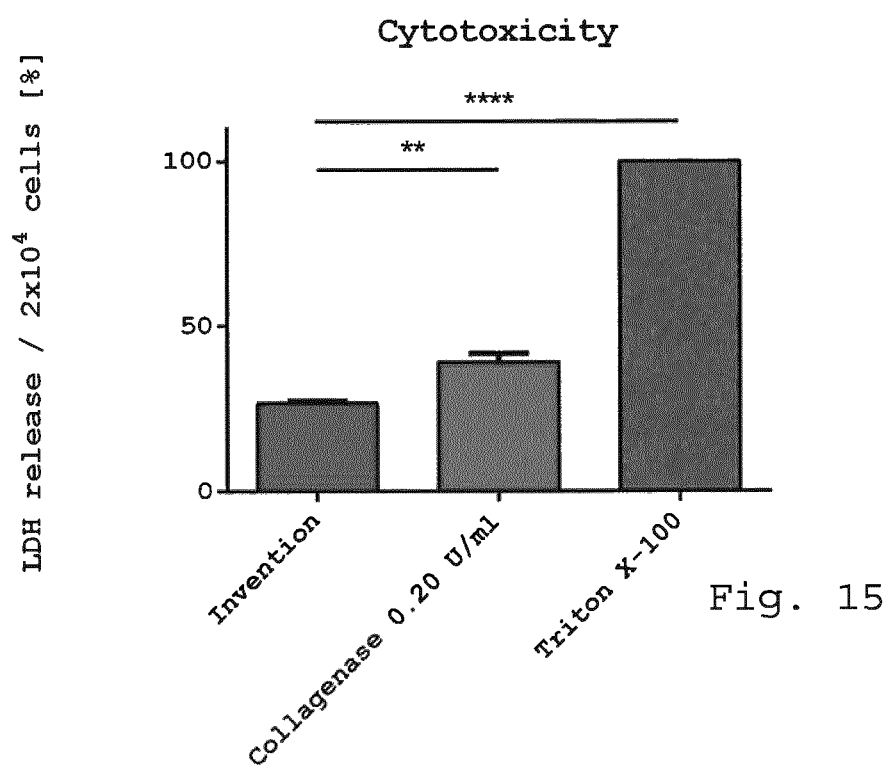
Figure 16A:
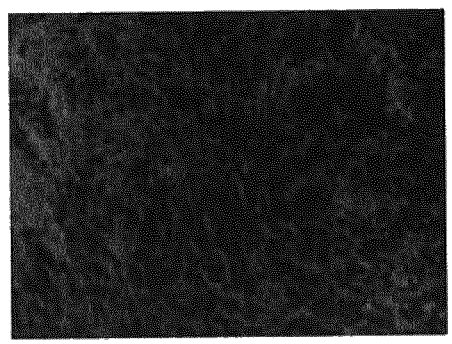
Figure 16A:
Figure 16A:
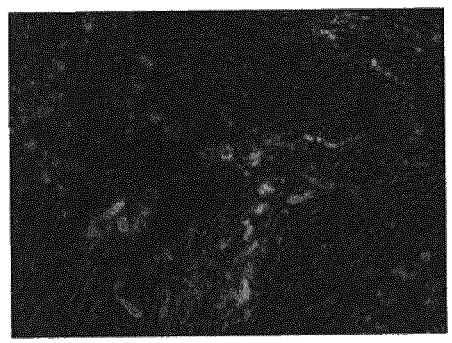
Figure 16A:
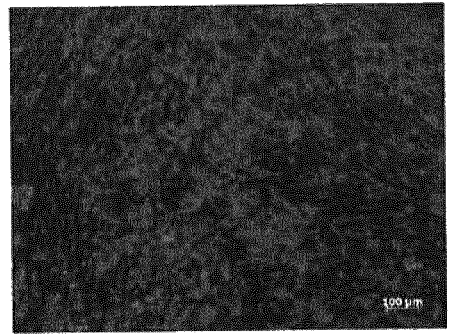
Figure 16B:
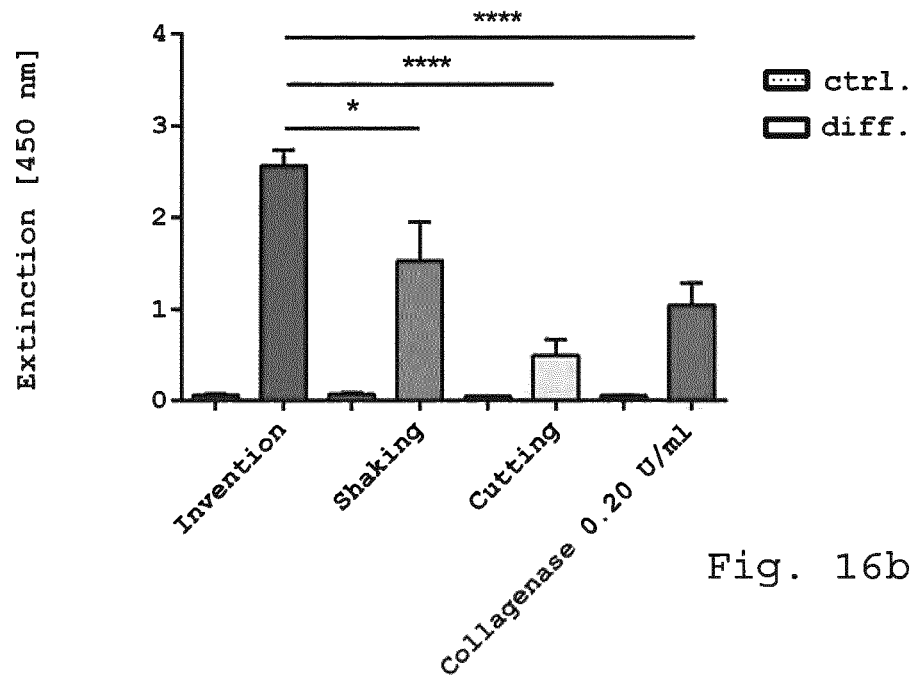
Figure 17:
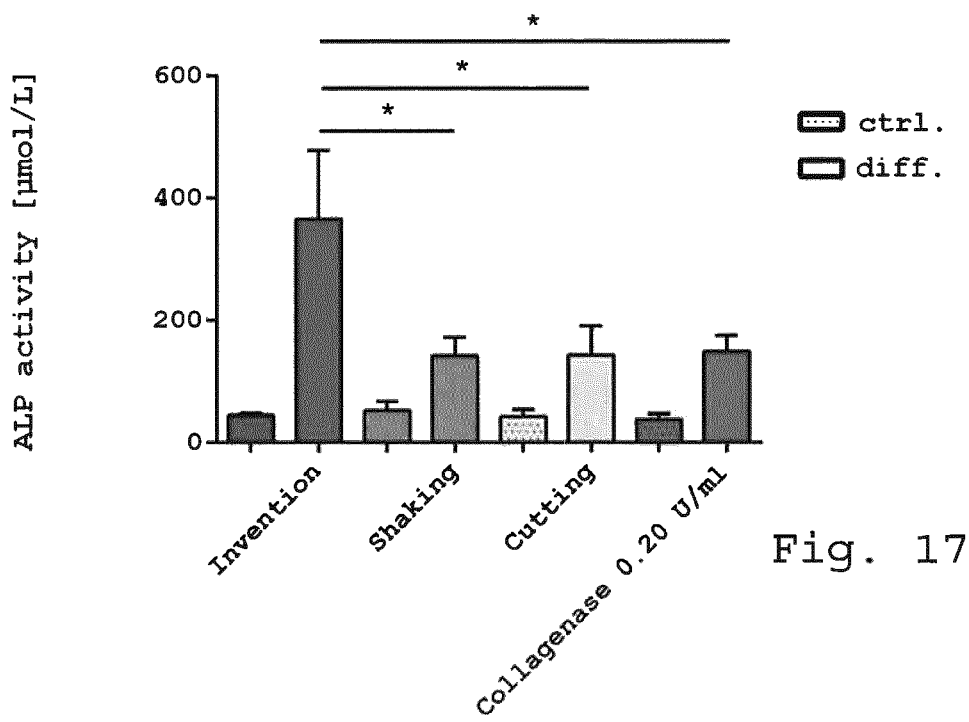
Figure 18A:
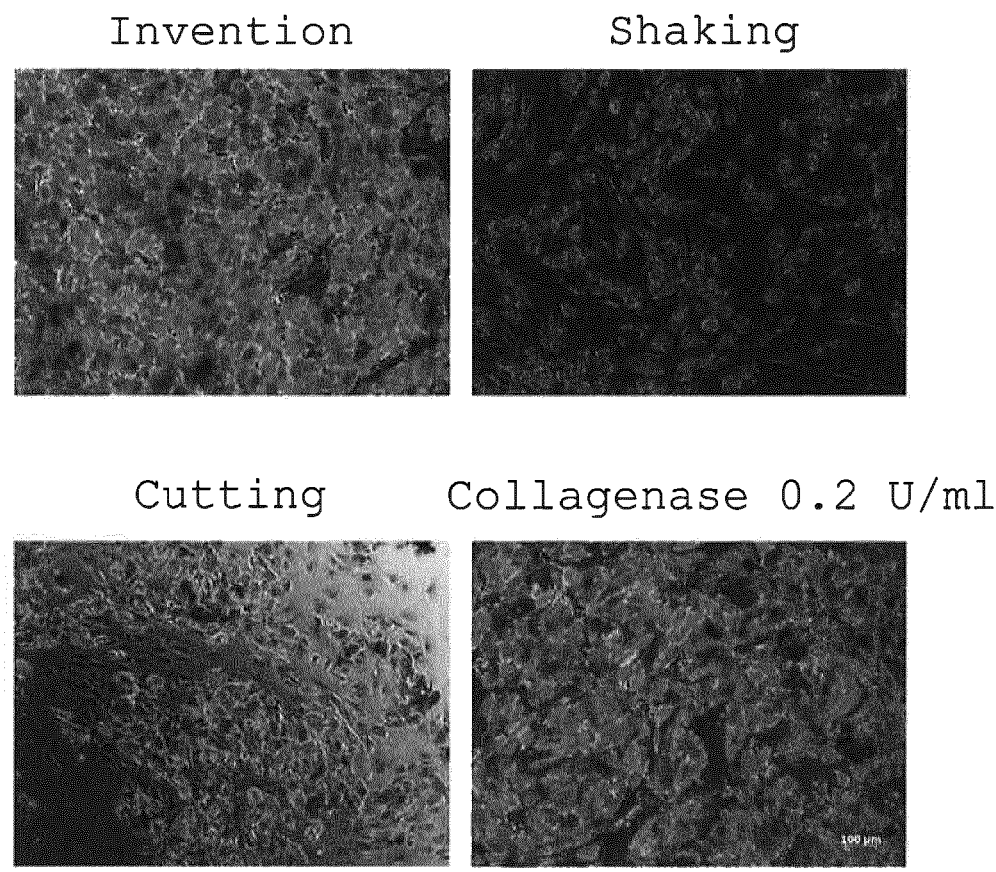
Figure 18B:
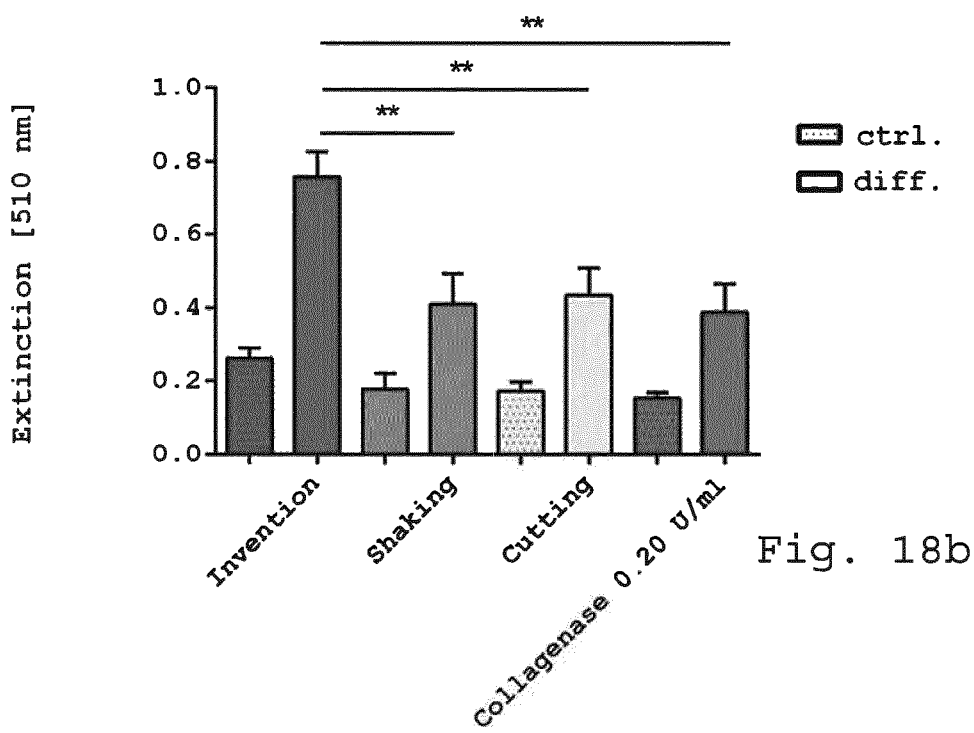
Figure 19A:
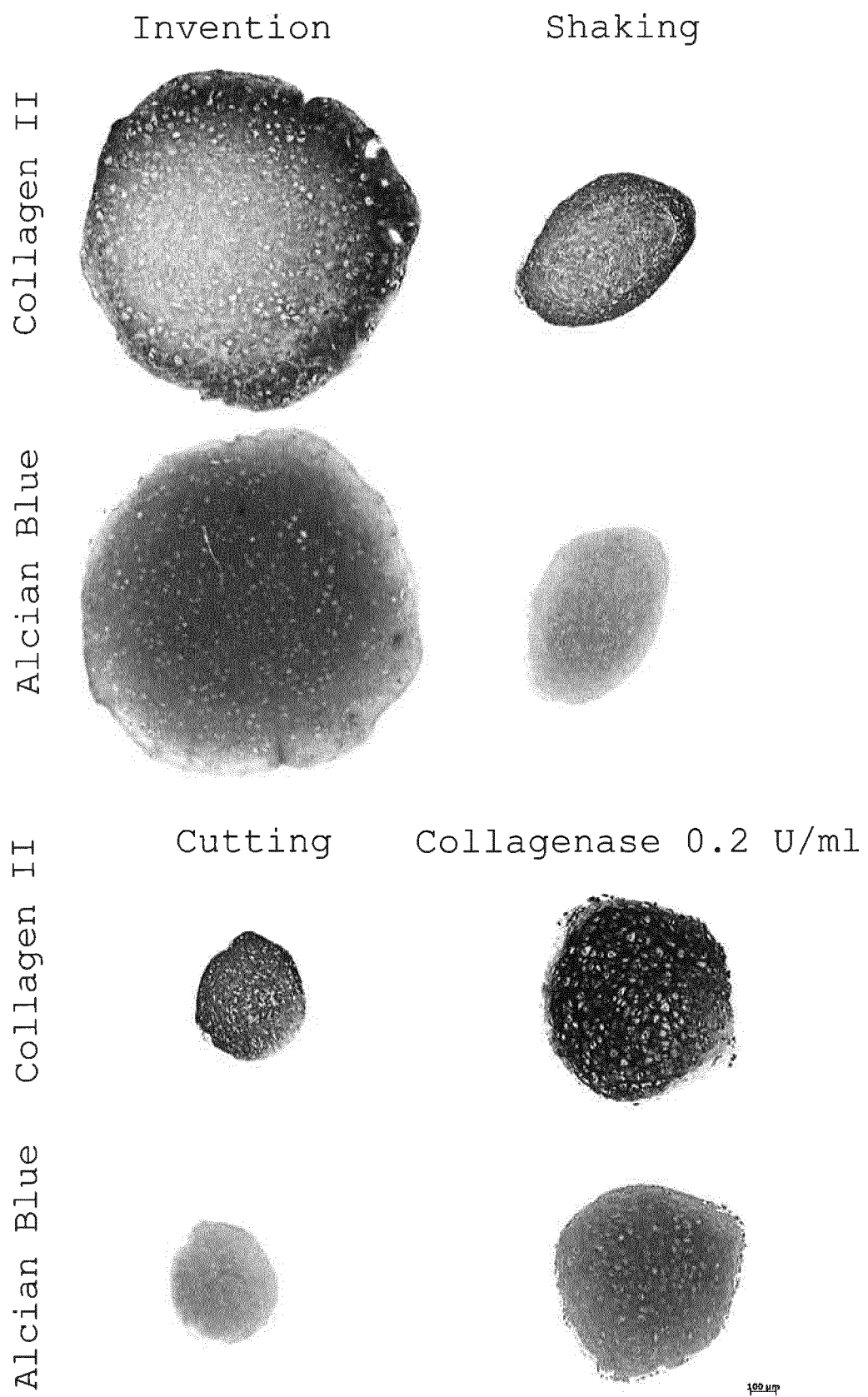
Figure 19B:
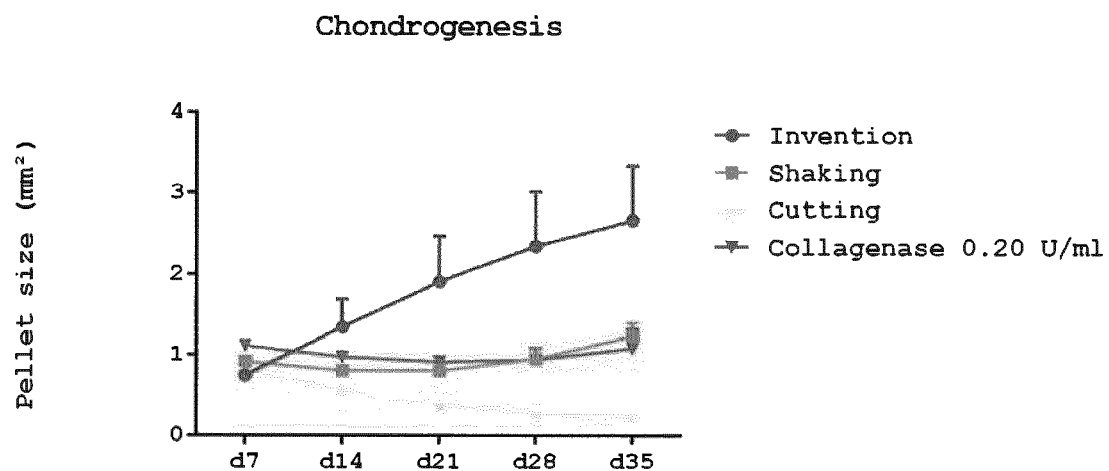
Figure 20:
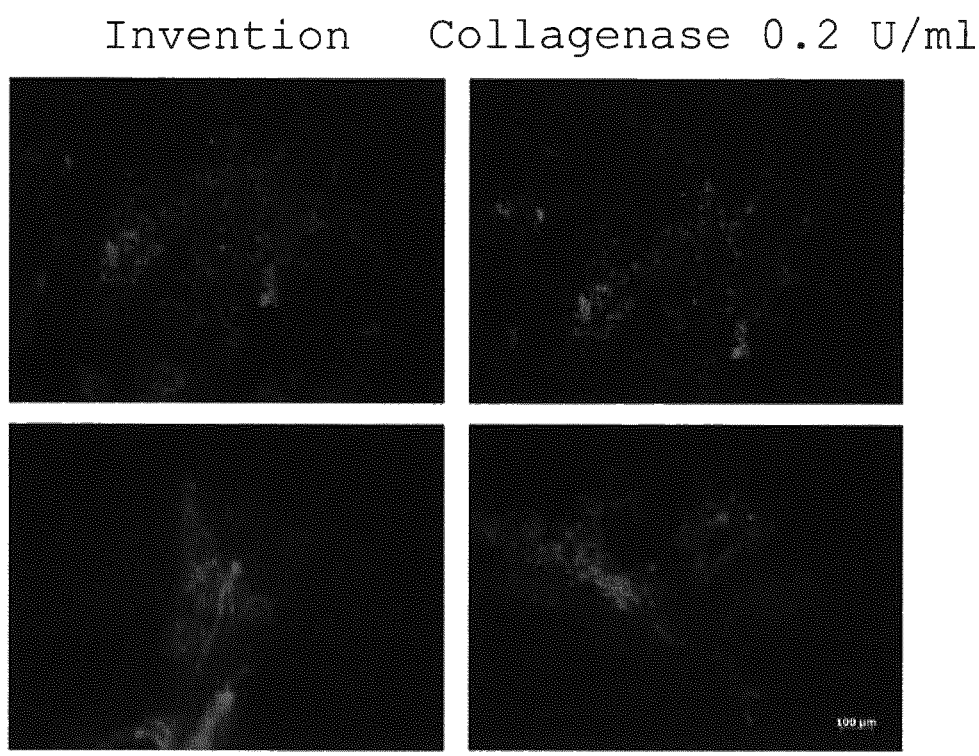
Figure 21:
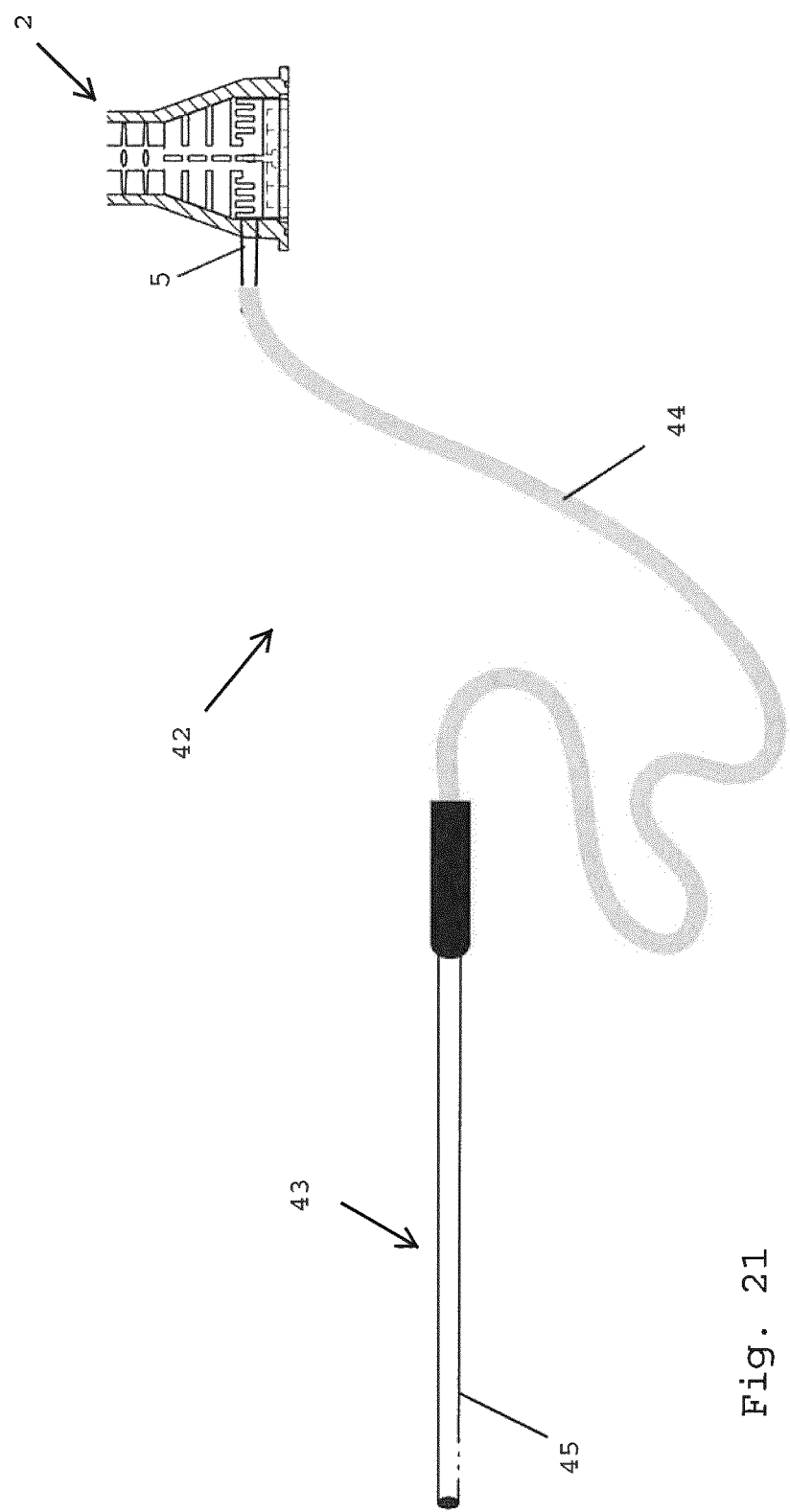

FIG. 9 shows the cell viability of freshly isolated therapeutic cells/microtissue from 100 ml liposuction material, wherein the percentage of freshly isolated living cells derived from enzymatic and non-enzymatic isolation methods was examined by Acridine Orange/DAPI fluorescence staining. There were no significant differences in the cell viability between the applied enzymatic and non-enzymatic isolation methods. (n=7);

FIG. 10a shows representative pictures of a colony-forming unit fibroblast (CFU-F) assay of freshly isolated cells. Freshly isolated cells derived from enzymatic isolation (right-hand side) and according to the invention (left-hand side) were seeded in a defined number of cells in each well of a 6-well plate and after 14 days cultivation the formed colonies were stained with hematoxylin/eosin;

FIG. 10b shows the result of a quantitative analysis, which revealed that cells isolated according to the invention showed a higher potential to form colonies compared to cells obtained by the enzymatic isolation method (n=5);

FIG. 11 shows a diagram of intra-/extracellular ATP of adherent cells. Adherent cells derived from enzymatic and non-enzymatic isolation methods were examined for intra-/extracellular ATP concentration. Cells isolated according to the invention showed significant higher intra-/extracellular ATP concentration compared to the enzymatic isolation method and to the non-enzymatic isolation methods shaking and cutting (*$p<0.05$; **$p<0.01$; n=5);

FIGS. 12a and 12b illustrate the proliferation potential of adherent cells. Adherent cells derived from enzymatic and non-enzymatic isolation methods were examined after 3 and 7 days in expansion media by light microscopy (FIG. 12a) and after 7, 14 and 21 days in expansion media for their proliferation potential by population doubling level (PDL) (FIG. 12b). Cells derived from all isolation methods showed spindle-shaped cell morphology on day 7. Size bar=100 µm (FIG. 12a). Cells isolated after processing according to the invention showed similar PDL compared to the enzymatic isolation method or to the non-enzymatic isolation methods shaking and cutting (FIG. 12b) (*$p<0.05$; **$p<0.01$; n=5);

FIG. 13a-f show diagrams comparing the immunophenotype of freshly isolated cells. Freshly isolated cells derived from enzymatic isolation method (0.2 U/ml collagenase) and non-enzymatic isolation according to the invention were examined for cellular composition. While there was no difference in the mesenchymal stem cell marker CD73 (FIG. 13a), CD90 (FIG. 13b) and CD105 (FIG. 13c) endothelial progenitor cells (CD45−/CD31+/CD34+) (FIG. 13d) and pericyte like-cells (FIG. 13e) were slightly reduced when using the invention compared to enzymatic isolation. The number of SA-ASC was enhanced when using the invention compared to enzymatic isolation (FIG. 13f). (n=3-4);

FIG. 14a-d show diagrams comparing the immunophenotype of adherent cells. Adherent cells derived with the invention or enzymatic isolation method (0.2 U/ml collagenase) were examined for cellular composition. While there was no difference in the mesenchymal stem cell marker CD73, CD90 and CD105 as well as the endothelial/pericytic marker CD146, an increase in the hematopoietic marker CD45 and the endothelial marker CD31 and CD34 was visible with the invention (FIG. 14a). Endothelial progenitor cells (CD45−/CD31+/CD34+) were significantly enhanced with the invention compared to enzymatic isolation (FIG. 14b). Also the number of pericyte like-cells (CD45−/CD31−/CD146+) was positively affected by the invention (FIG. 14c). The number of SA-ASC was still high after 6 days in culture with the invention but lower than with enzymatic isolation (FIG. 14d). (*$p<0.05$; **$p<0.01$. n=3);

FIG. 15 shows a diagram comparing the cytotoxicity of freshly isolated cells (LDH release). Cell death was assessed by LDH release after 24 h in expansion media. Cells derived using the invention and enzymatic isolation method (collagenase 0.2 U/ml) were compared to a control using Triton X-100 where 100% of the cells died. Cells derived from the inventive method showed significant lower LDH release compared to the enzymatic isolation method. ($p<0.01$; **$p<0.0001$. n=3);

FIGS. 16a and 16b illustrate a comparison of the osteogenic differentiation potential of adherent cells analyzed with Alizarin red staining (FIG. 16a) and quantification (FIG. 16b). Adherent cells derived by the invention, enzymatic and non-enzymatic isolation methods were examined after 1 week in expansion media and 3 more weeks in osteogenic differentiation media for their osteogenic differentiation potential stained with Alizarin red for matrix mineralization and calcification. Alizarin red staining demonstrated less mineralization for cells isolated with the enzymatic isolation method and the non-enzymatic isolation methods shaking and cutting but intense staining for cells derived with the invention. Size bar=100 µm (FIG. 16a). The quantitative analysis revealed that cells isolated with the invention showed significantly higher Alizarin red extinction compared to cells obtained by the enzymatic isolation method and the non-enzymatic isolation methods cutting and shaking (FIG. 16b). (Ctrl.: cells in control media without growth factors and stimuli, diff.: cells in osteogenic differentiation media. *$p<0.05$; ****$p<0.0001$. n=5);

FIG. 17 shows a diagram of the osteogenic differentiation potential of adherent cells analyzed with alkaline phosphatase (ALP). Adherent cells derived with the invention, enzymatic and non-enzymatic isolation methods were examined after 1 week in expansion media and 3 more weeks in osteogenic differentiation media for their osteogenic differentiation potential stained with ALP which is expressed in active osteoblasts. Cells isolated using the invention showed significant higher ALP activity compared to all other methods. (Ctrl.: cells in control media without growth factors and stimuli, diff.: cells in osteogenic differentiation media. For statistical analysis one-way ANOVA Tukey's post hoc was performed. *p<0.05. n=5);

FIGS. 18a and 18b illustrate a comparison of the adipogenic differentiation potential of adherent cells analyzed with Oil red O staining (FIG. 18a) and quantification (FIG. 18b). Adherent cells derived with the invention, enzymatic and non-enzymatic isolation methods were examined after 1 week in expansion media and 3 more weeks in adipogenic differentiation media for their adipogenic differentiation potential stained with Oil red O for lipid droplet formation. Oil red O staining demonstrated less lipid droplet formation for cells isolated with the enzymatic isolation method and the non-enzymatic isolation methods shaking and cutting but intense lipid droplet formation for cells derived by the invention. Size bar=100 μm (a). The quantitative analysis revealed that cells isolated with the invention showed significant higher Oil red O extinction compared to cells obtained by the enzymatic isolation method and the non-enzymatic isolation methods cutting and shaking (FIG. 18b). (Ctrl.: cells in control media without growth factors and stimuli, diff.: cells in adipogenic differentiation media. p<0.01 *p<0.001. n=5);

FIGS. 19a and 19b illustrate a comparison of the chondrogenic differentiation potential of 3D micromass pellets analyzed with Alcian blue and collagen type II staining (FIG. 19a) and increasing pellet size over time (FIG. 19b). Adherent cells derived with the invention, enzymatic and non-enzymatic isolation methods were transferred after 1 week in expansion media as 3D micromass pellets for 5 more weeks in chondrogenic differentiation media. The 3D micromass pellets were measured every week for their cross section area and after 5 weeks stained with Alcian blue and collagen type II for their chondrogenic differentiation potential. Alcian blue and collagen type II staining demonstrated weak or absent staining for cells isolated with the enzymatic isolation method and the non-enzymatic isolation methods shaking and cutting but intense staining for cells derived with the invention. Size bar=100 μm (FIG. 19a). Cells obtained with the invention showed a faster growth of pellet size in chondrogenic differentiation media compared to all other isolation methods although the increase did not reach statistical significance (FIG. 19b). (p<0.01; *p<0.001. n=5);

FIG. 20 illustrates the vascularization potential of freshly isolated cells analyzed in 3D fibrin matrices. Freshly isolated cells derived from enzymatic isolation and with the invention were mixed with fibrinogen and thrombin for fibrin clot formation. After 2 weeks in expansion media including aprotinin they were analyzed for their vascularization potential with endothelial marker CD31 (green). The staining demonstrated development of tube-like morphology for cells derived from enzymatic isolation and with the invention. Size bar=200 μm (upper row), 100 μm (lower row). (n=1); and FIG. 21 shows a set for liposuction applications comprising a milling device according to FIG. 1 and a cannula.

Figure 22:
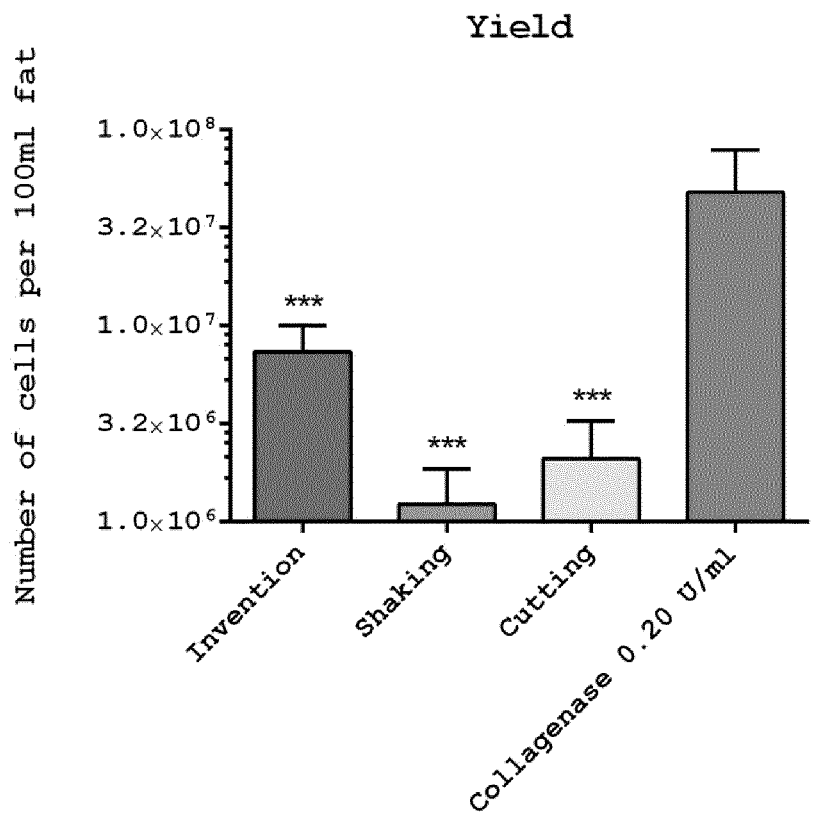
Figure 23:
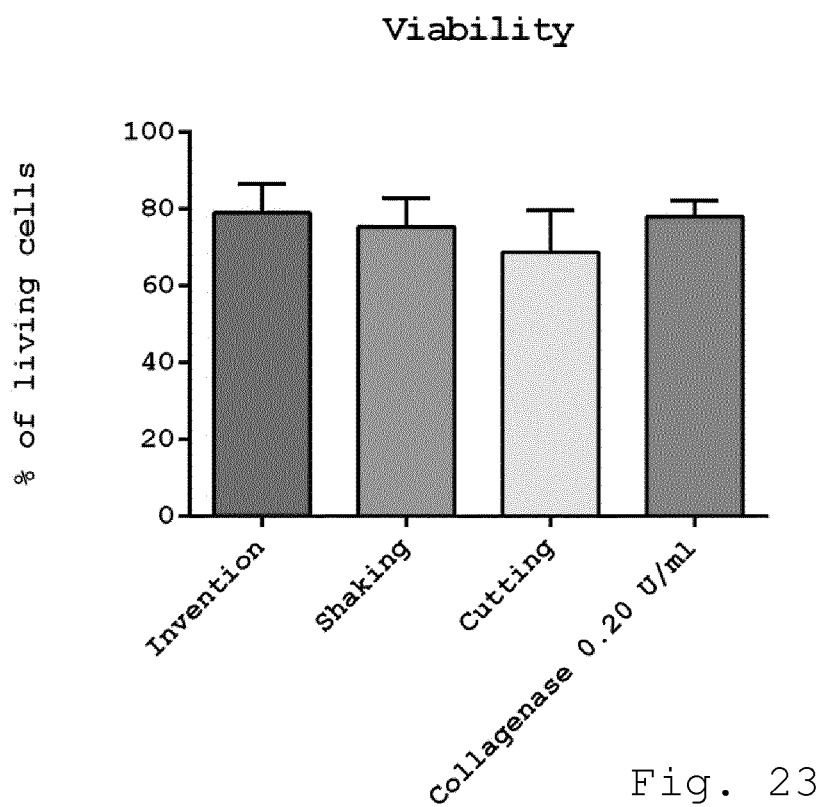
Figure 24A:
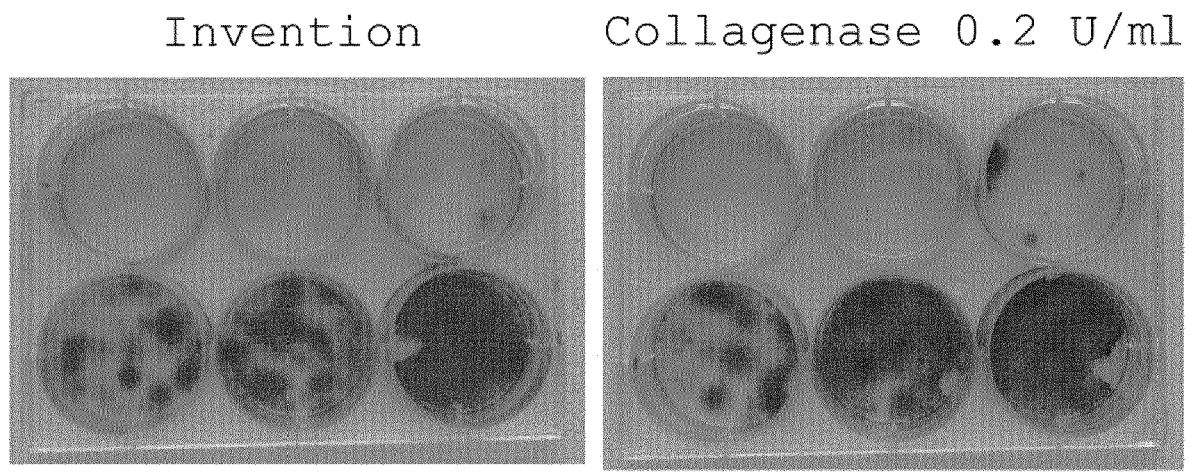
Figure 24B:
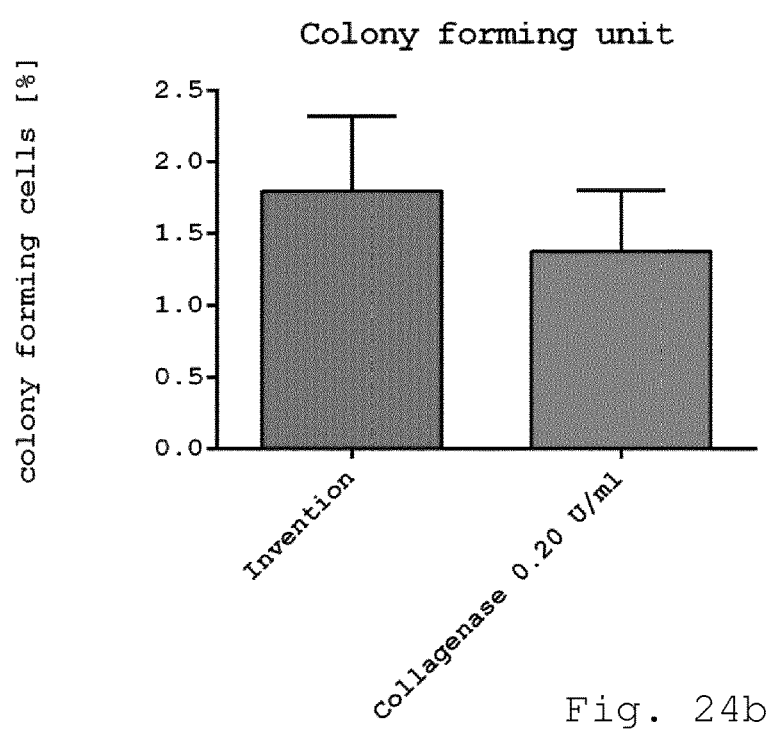
Figure 25:
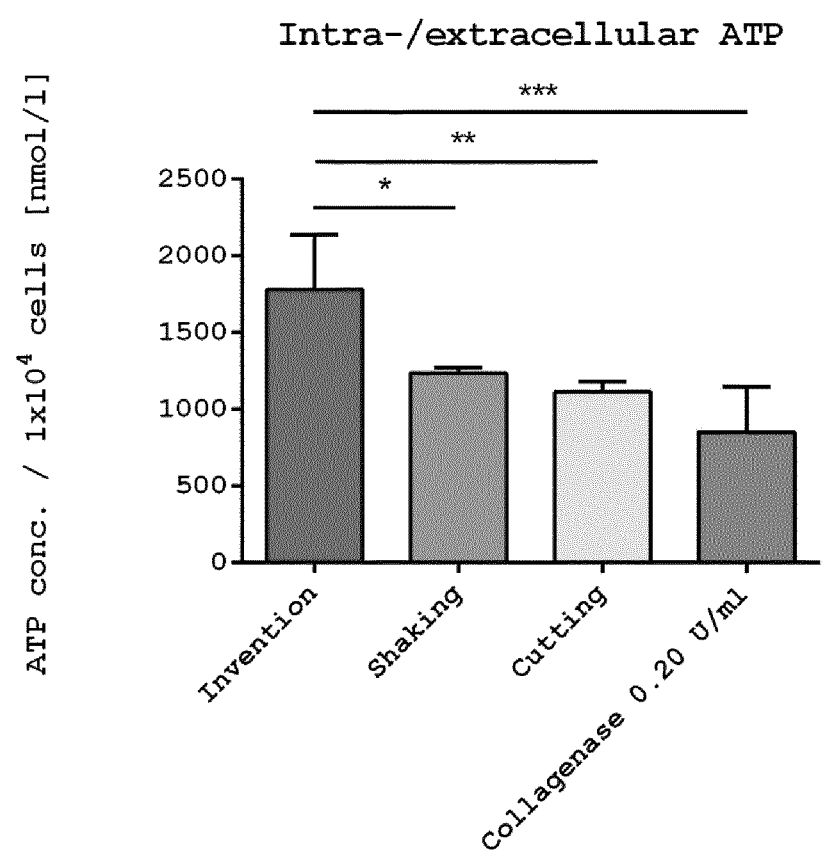
Figure 26A:
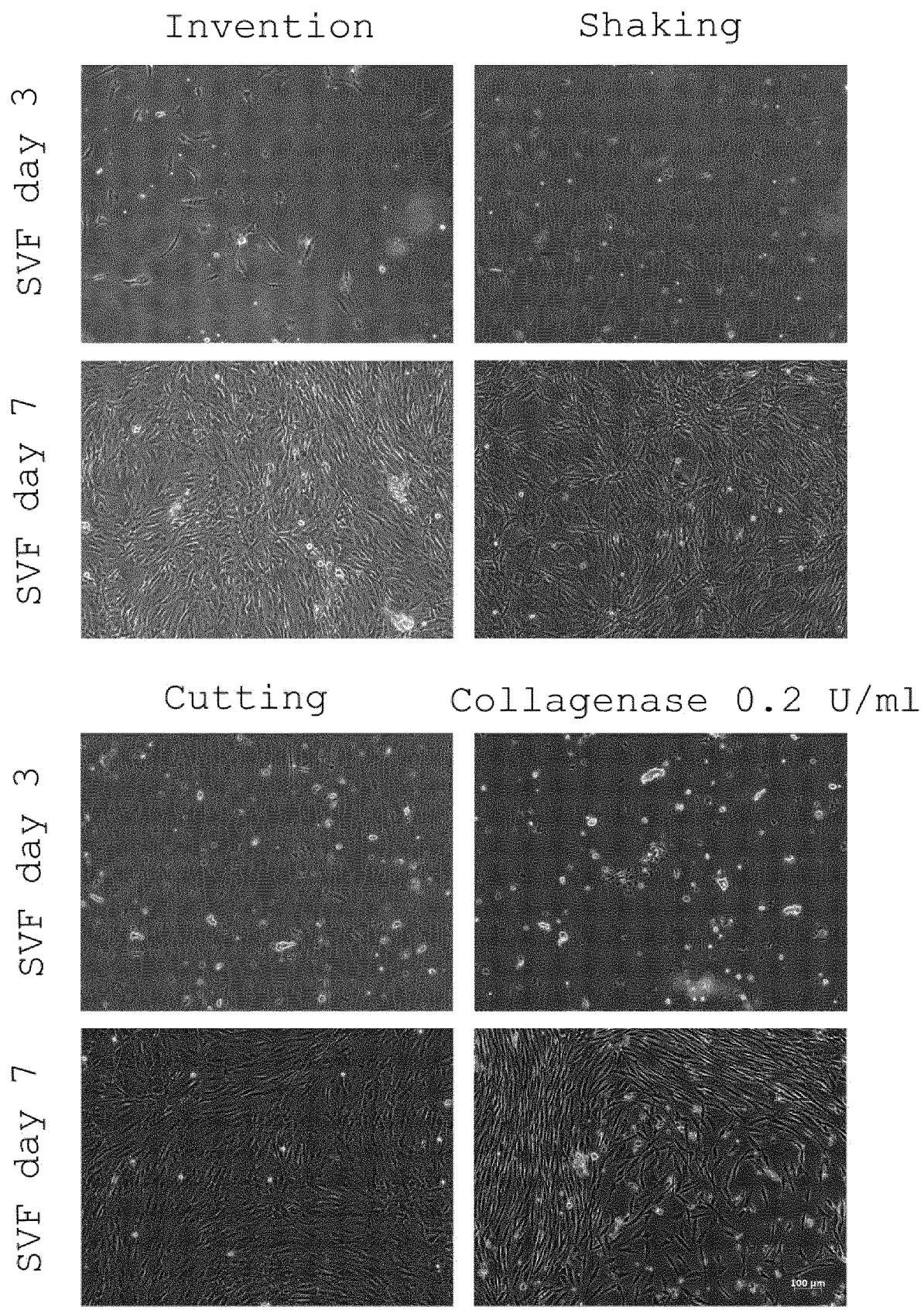
Figure 26B:
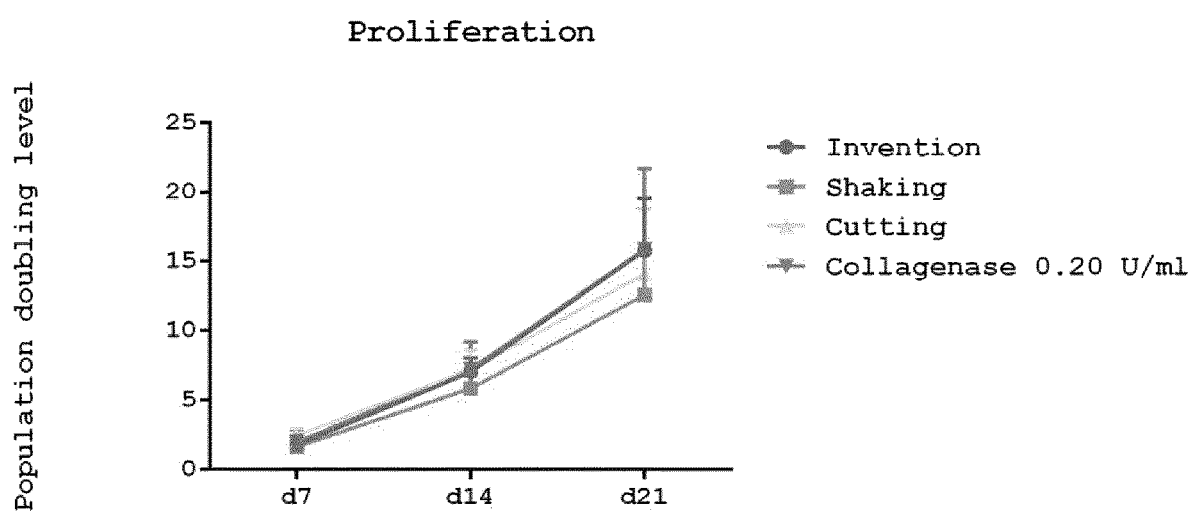
Figure 27A:
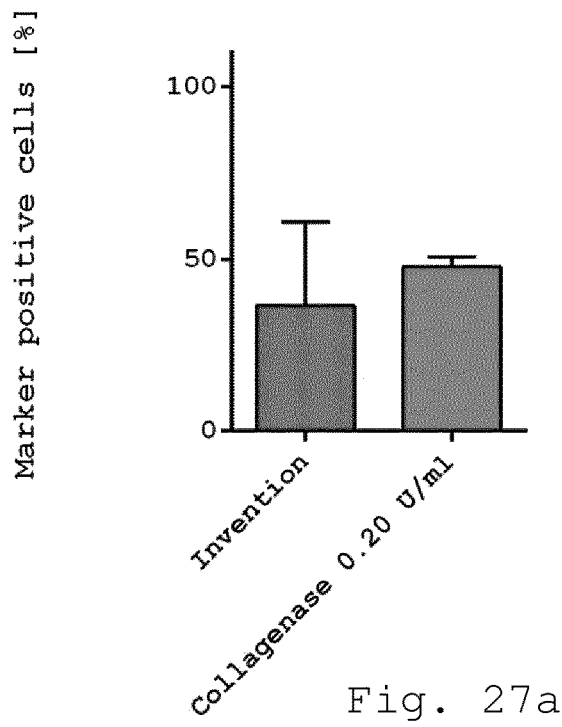
Figure 27B:
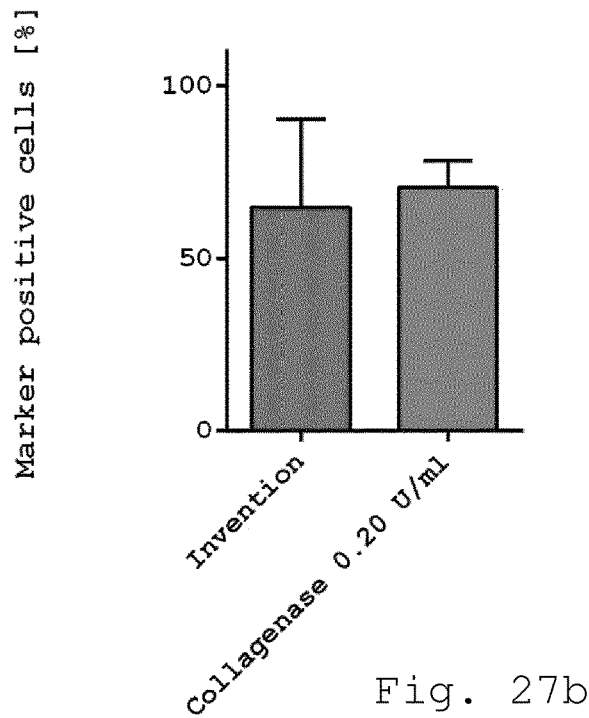
Figure 27C:
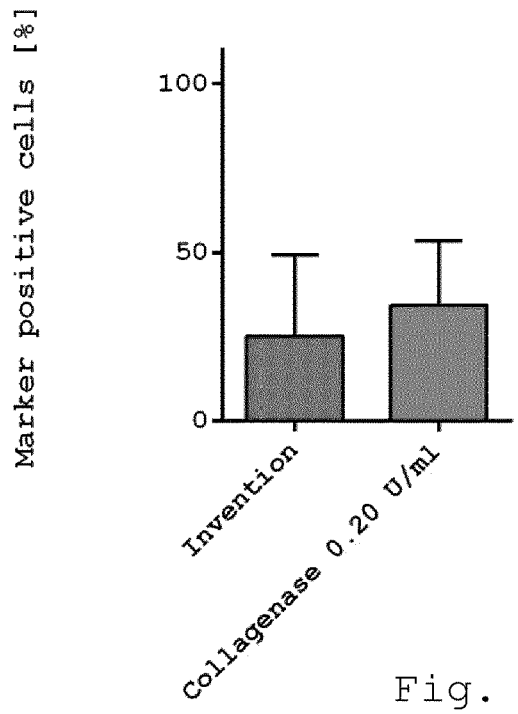
Figure 27D:
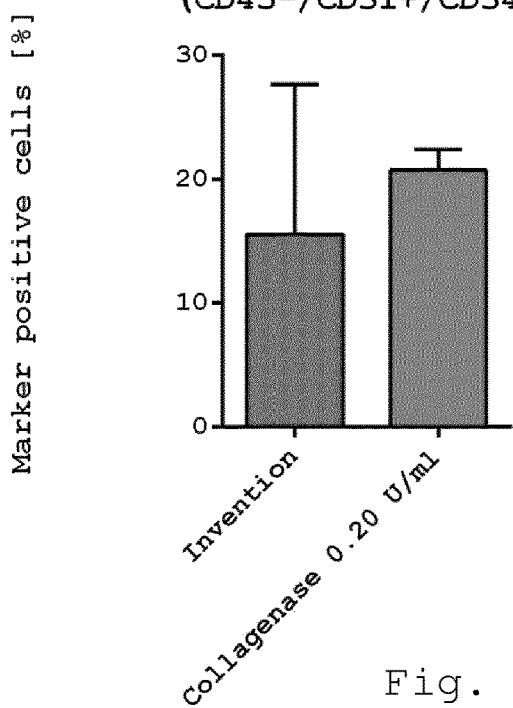
Figure 27E:
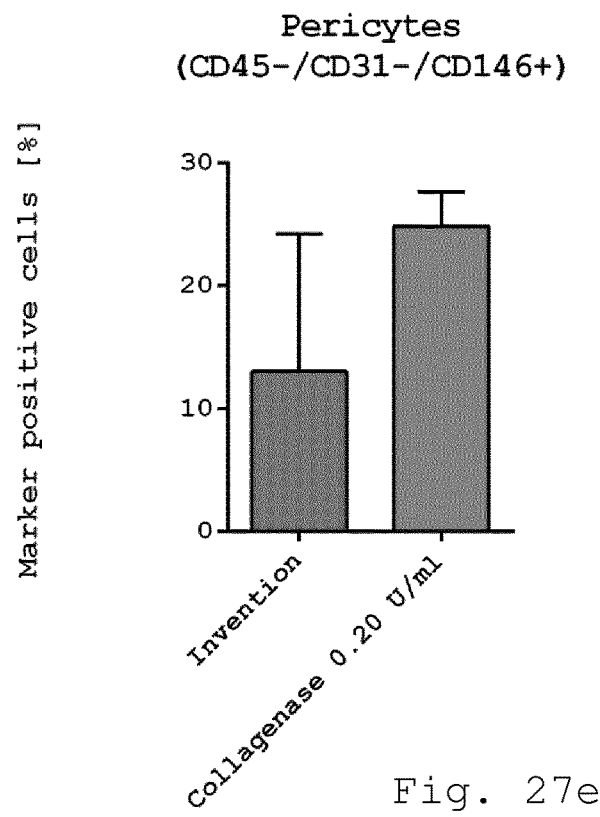
Figure 27F:
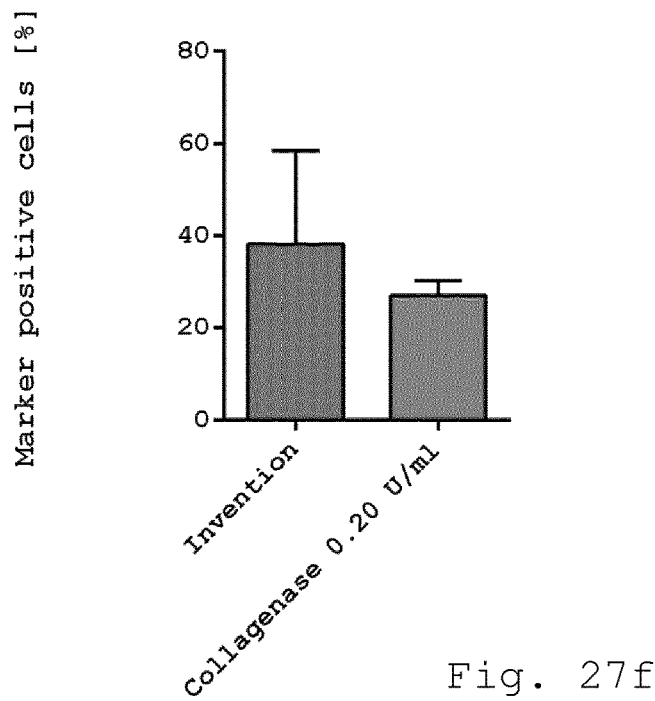
Figure 28A:
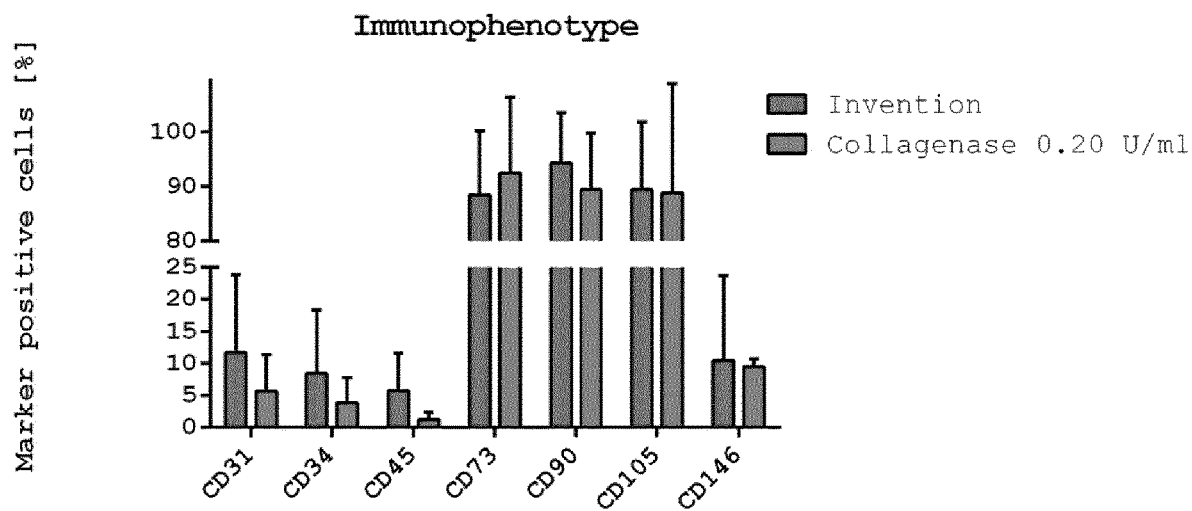
Figure 28B:
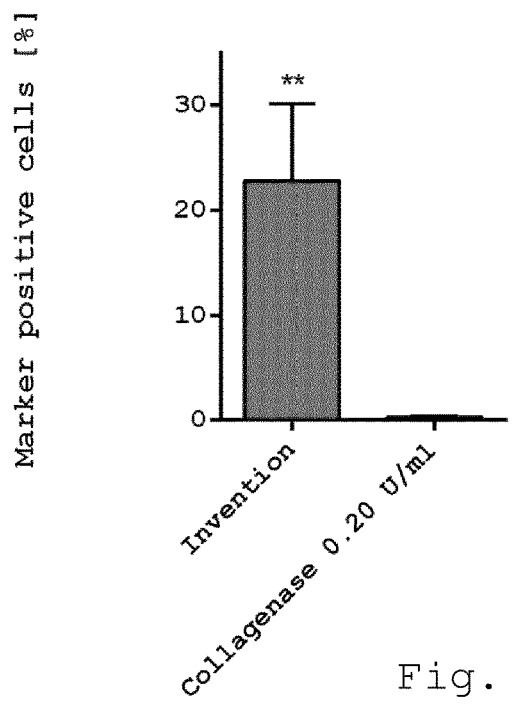
Figure 28C:
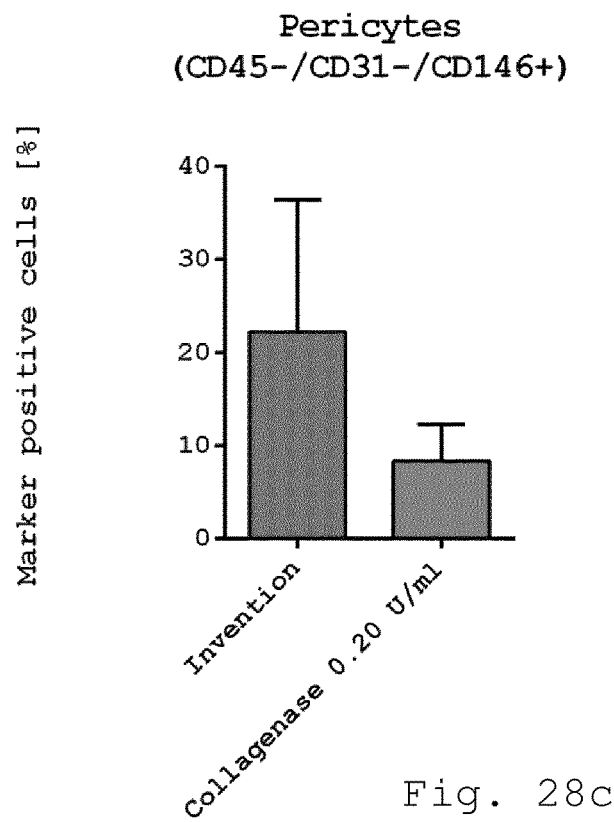
Figure 28D:
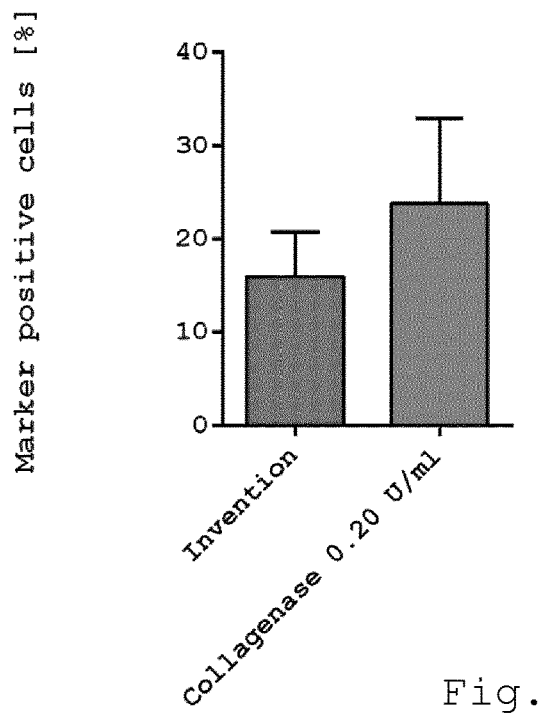
Figure 29:
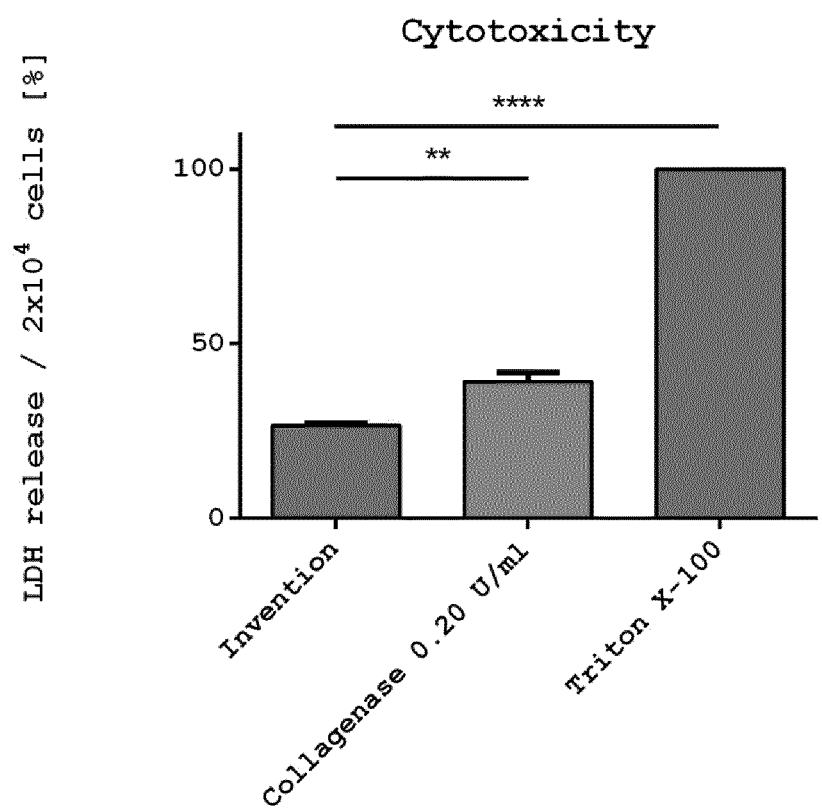
Figure 30A:
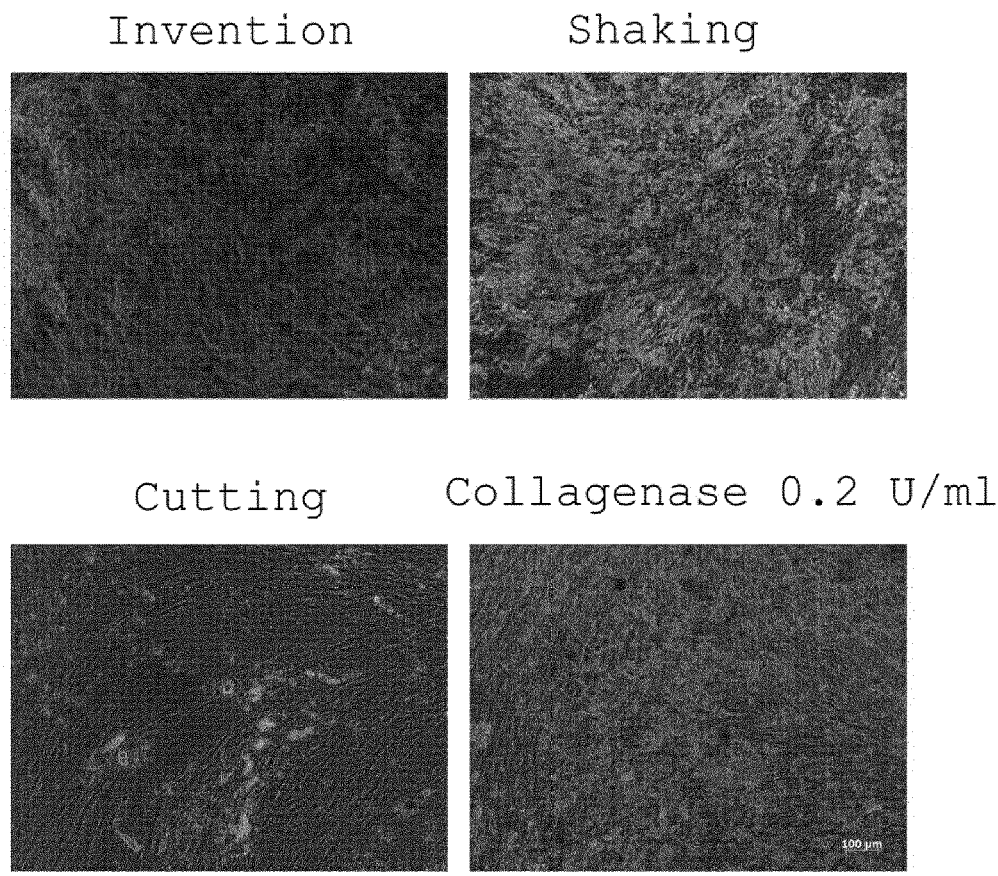
Figure 30B:
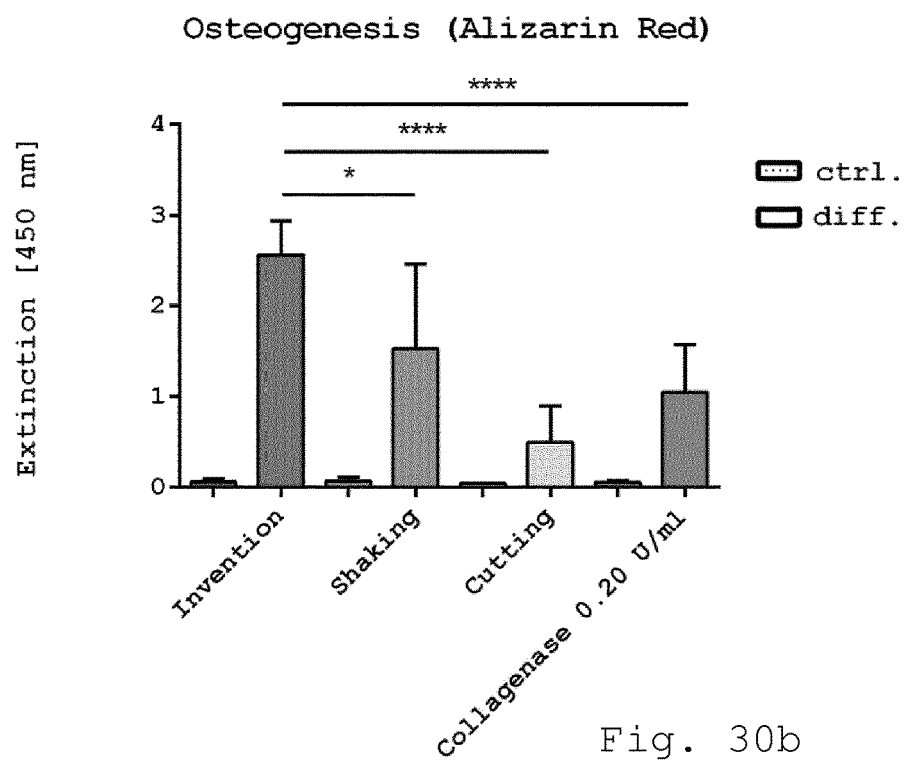
Figure 31:
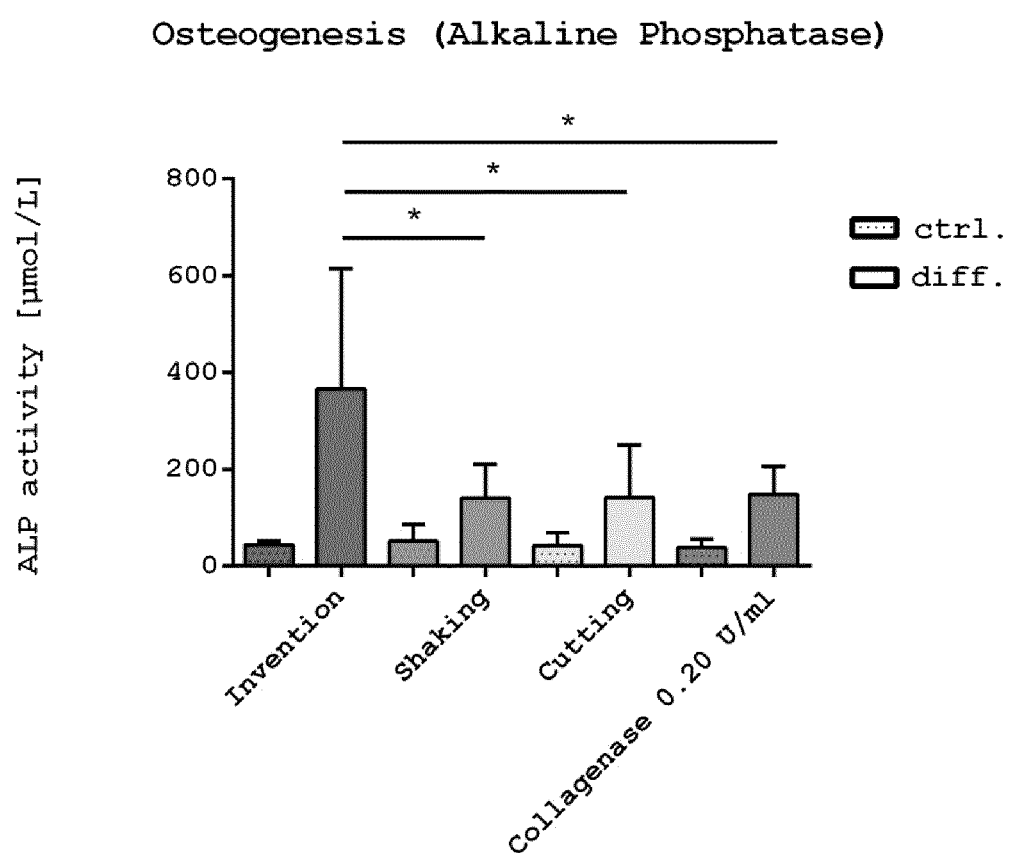
Figure 32A:
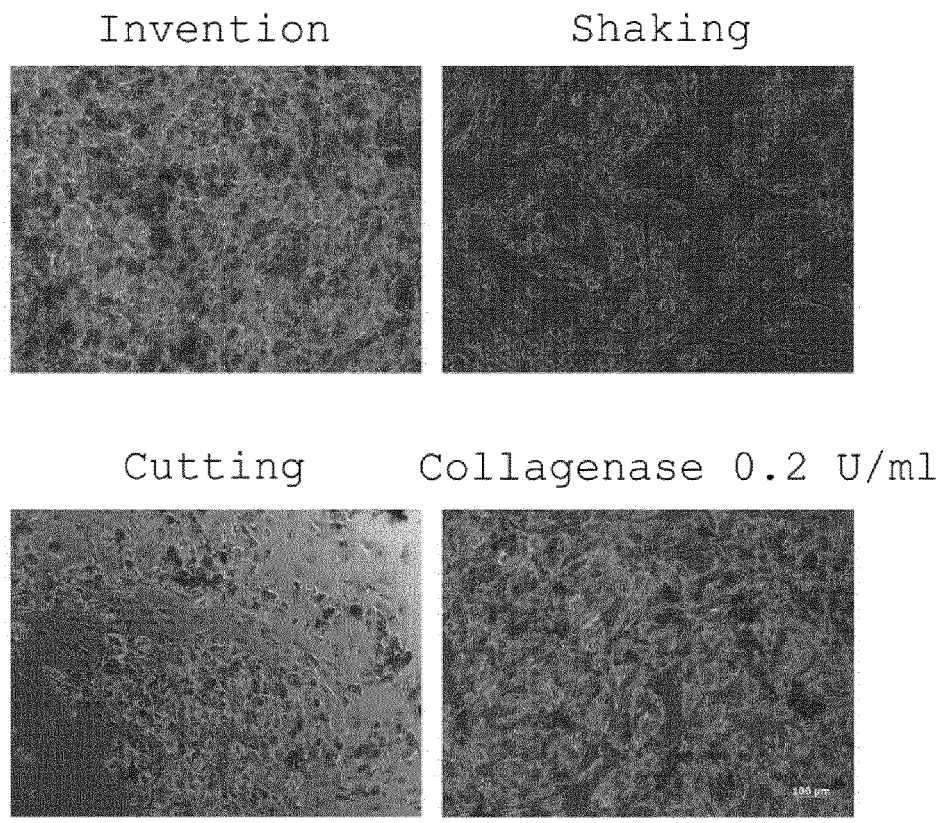
Figure 32B:
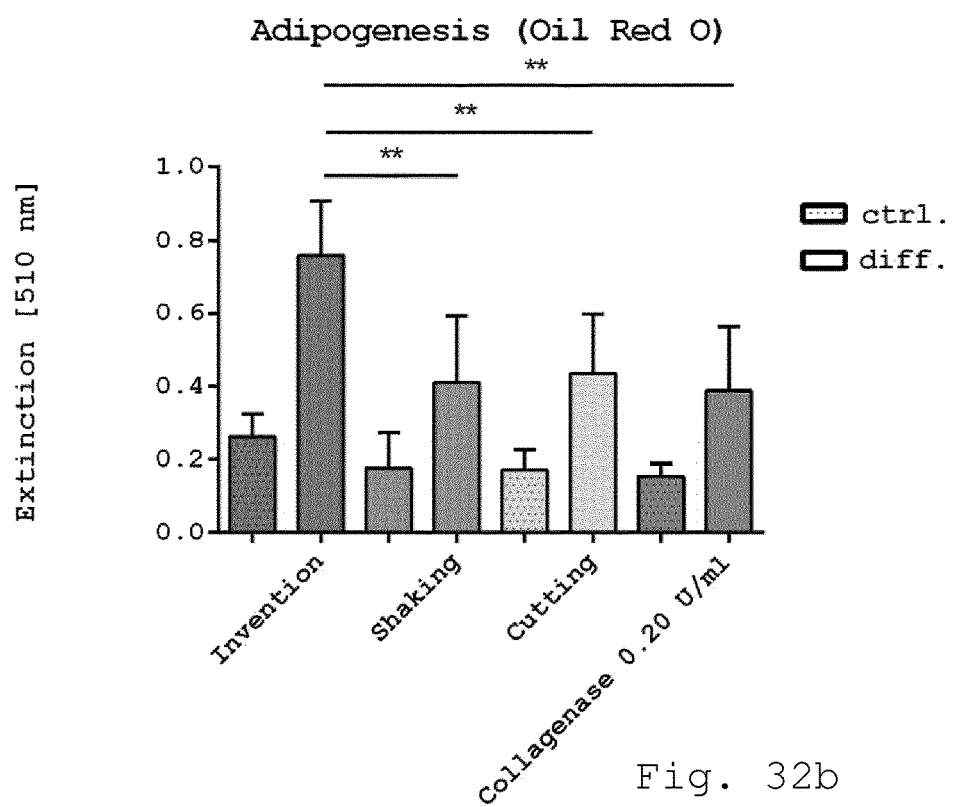
Figure 33A:
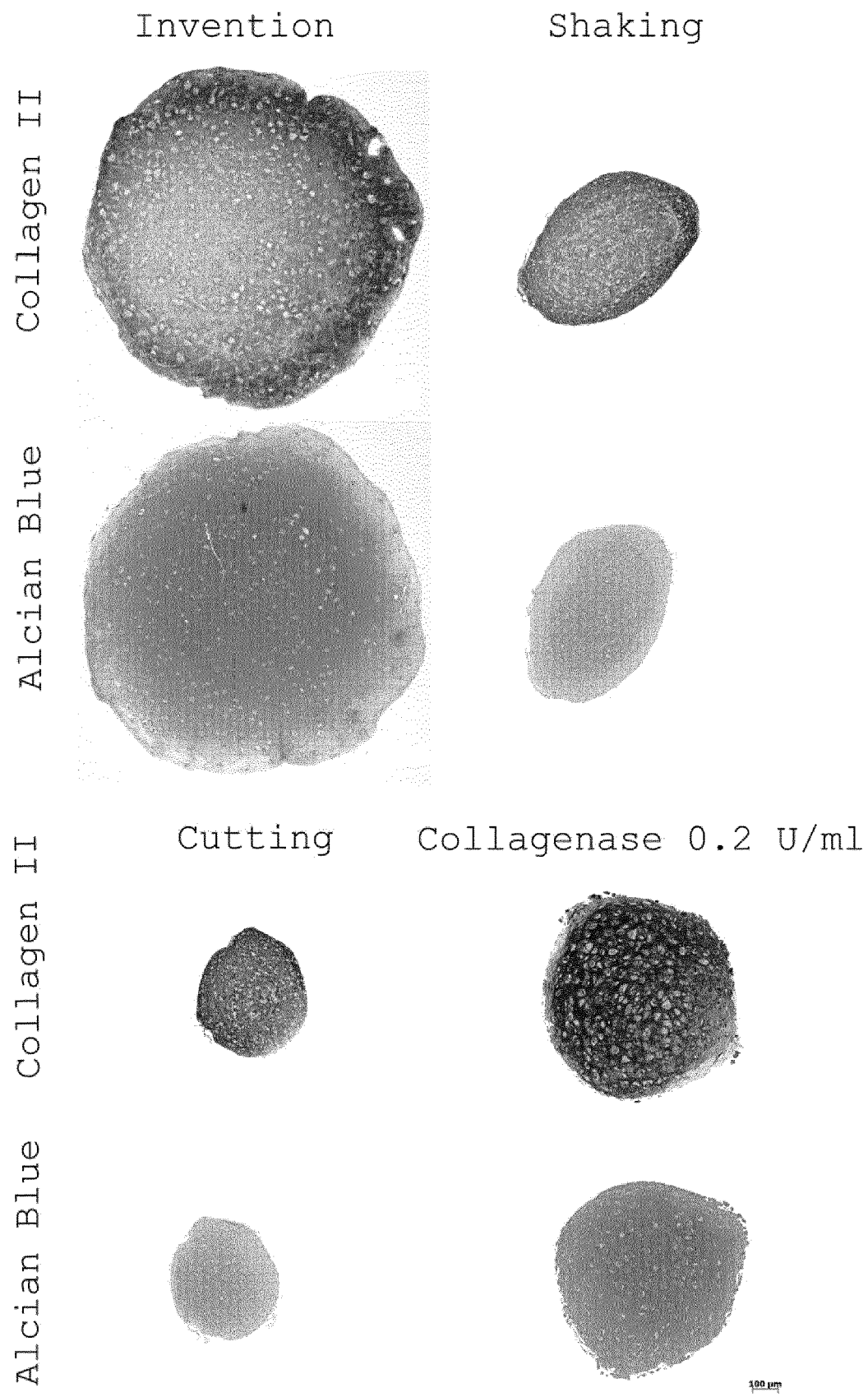
Figure 33B:
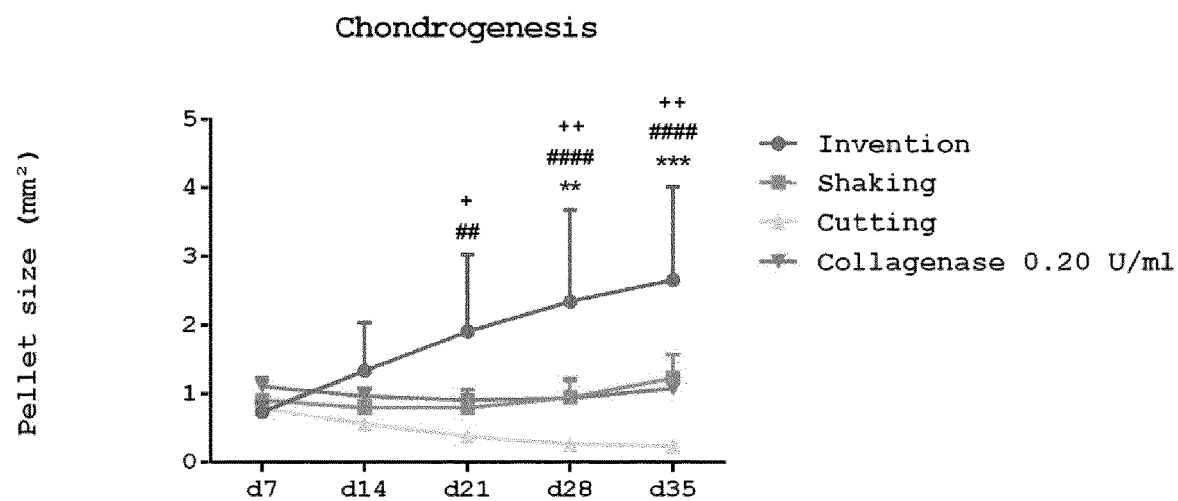
Figure 34:
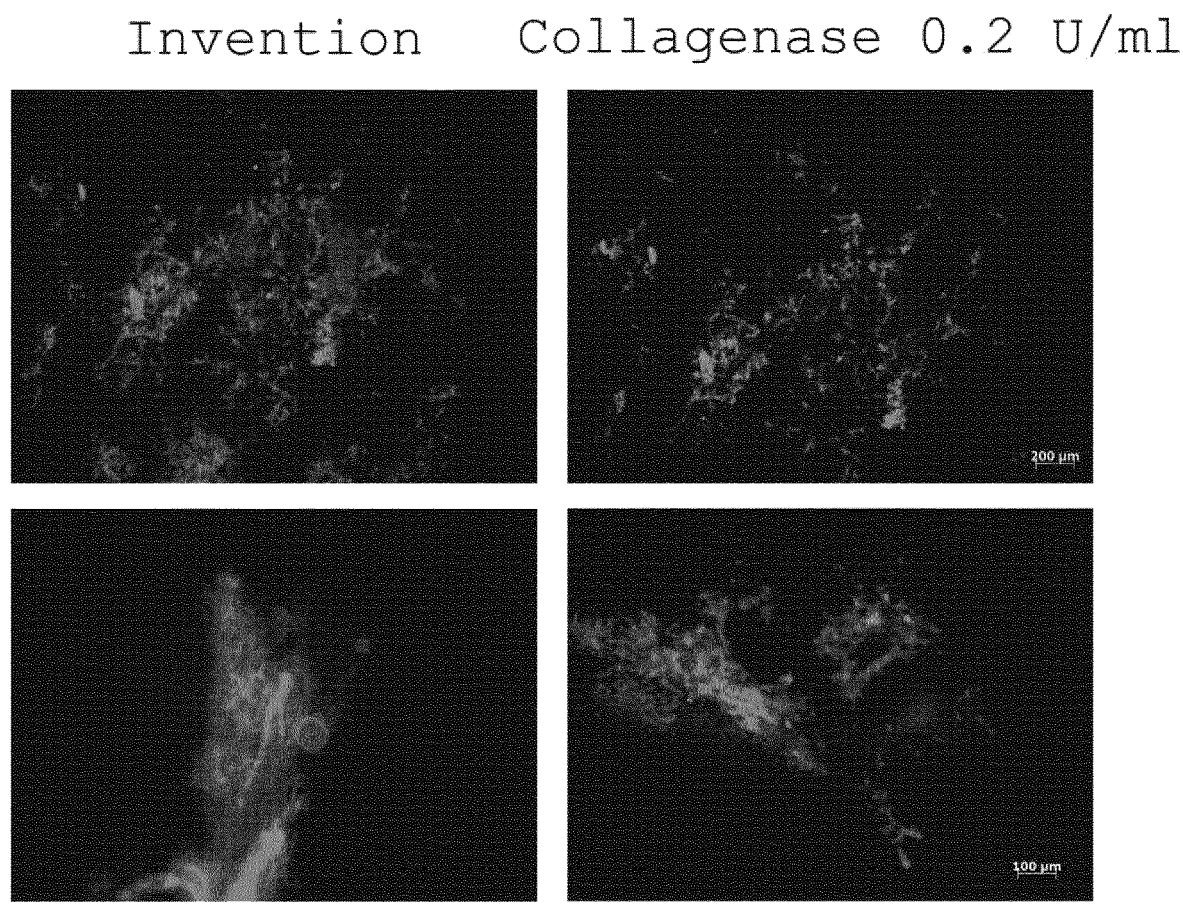
Figure 35:
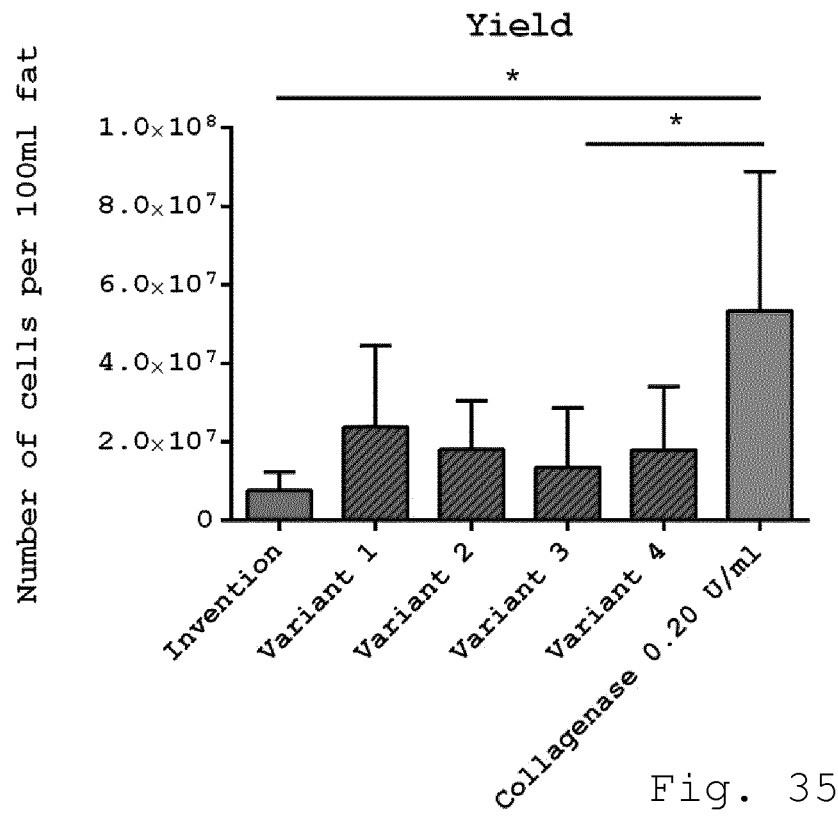
Figure 36:
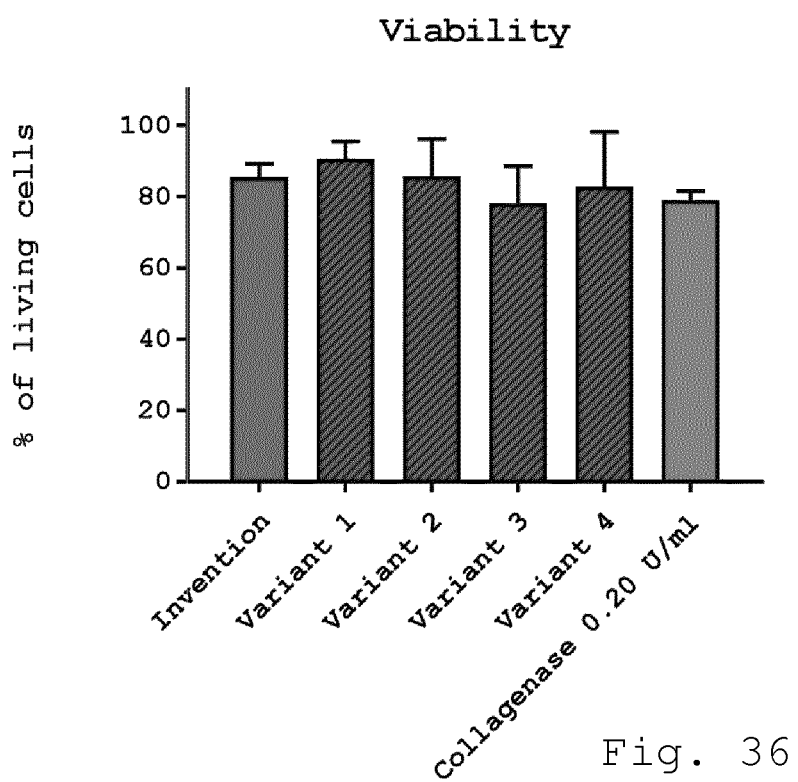
Figure 37:
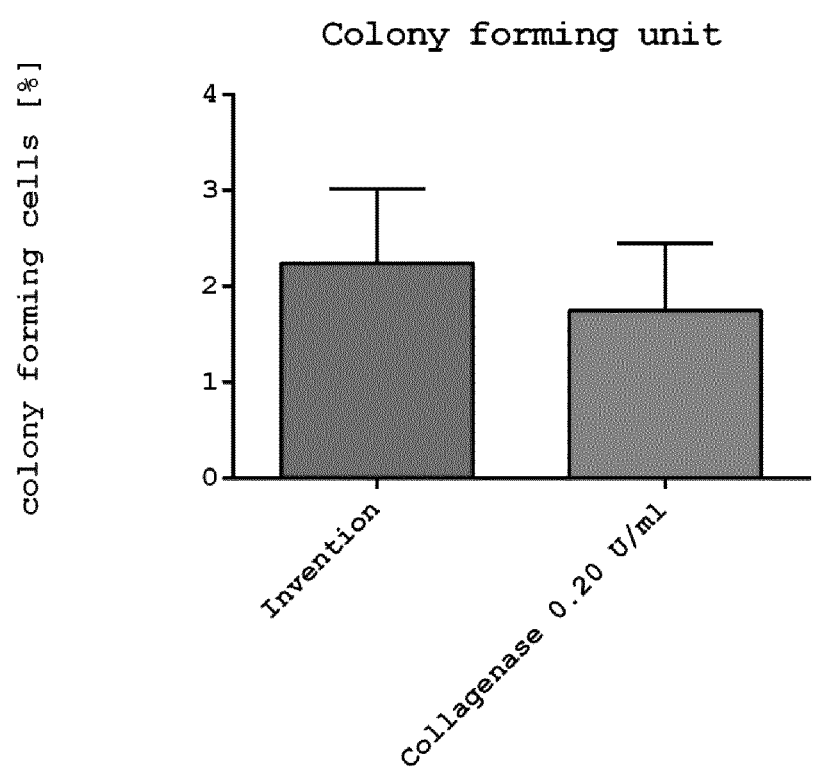
Figure 38A:
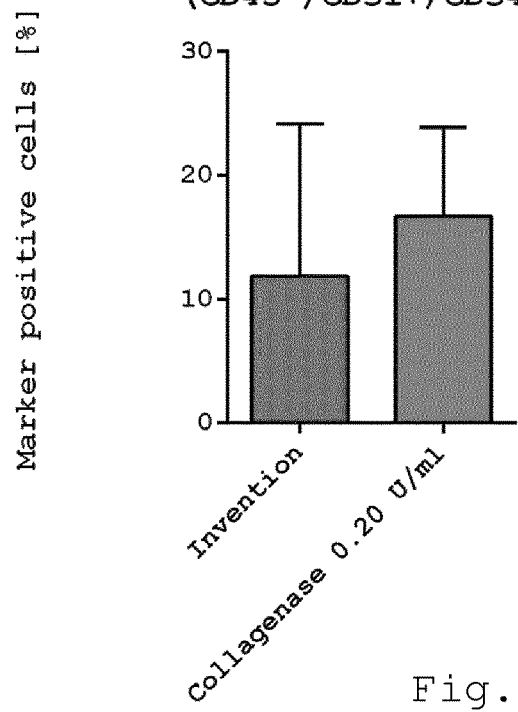
Figure 38B:
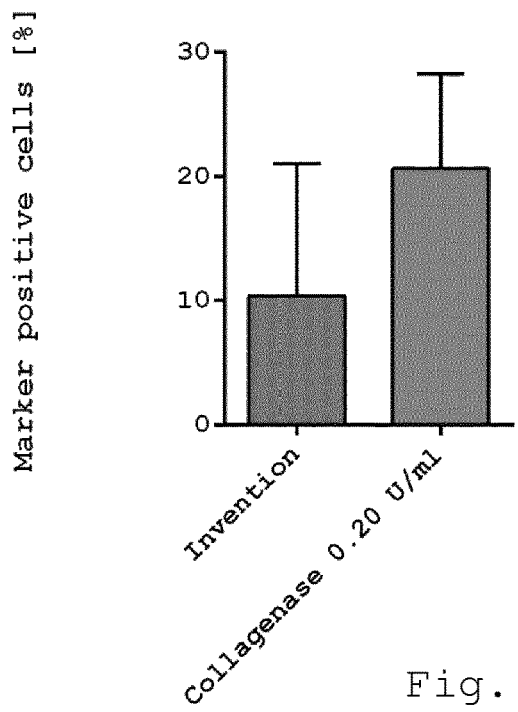
Figure 38C:
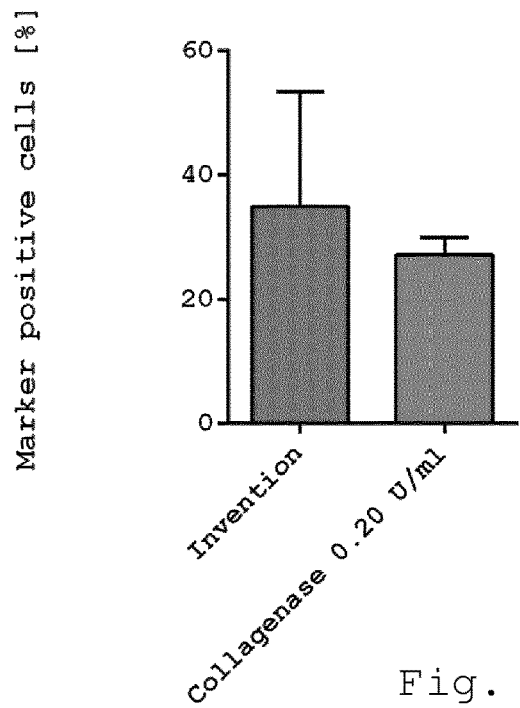
Figure 39:
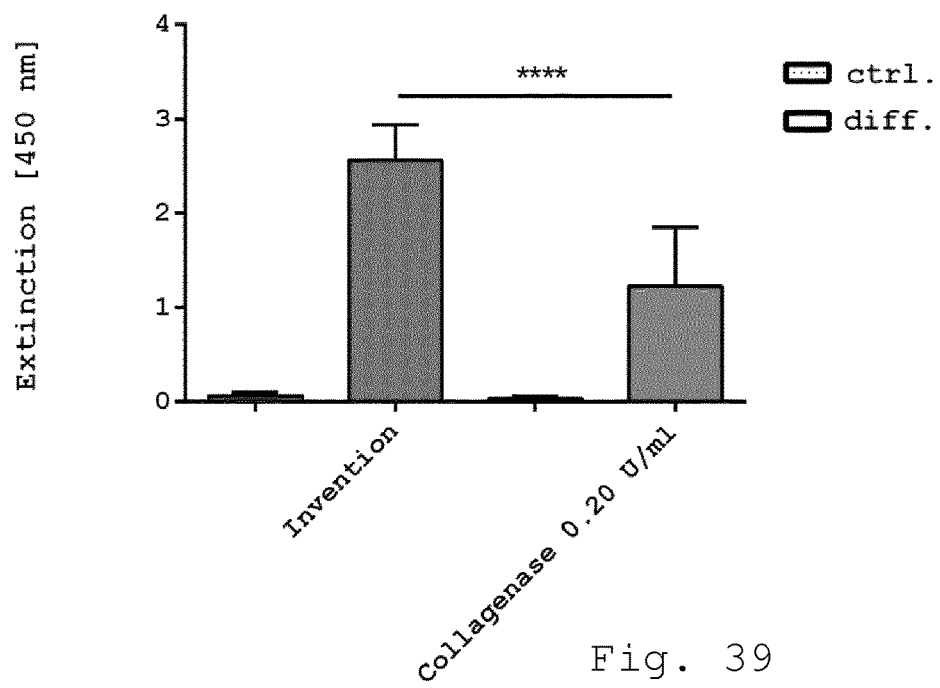
Figure 40:
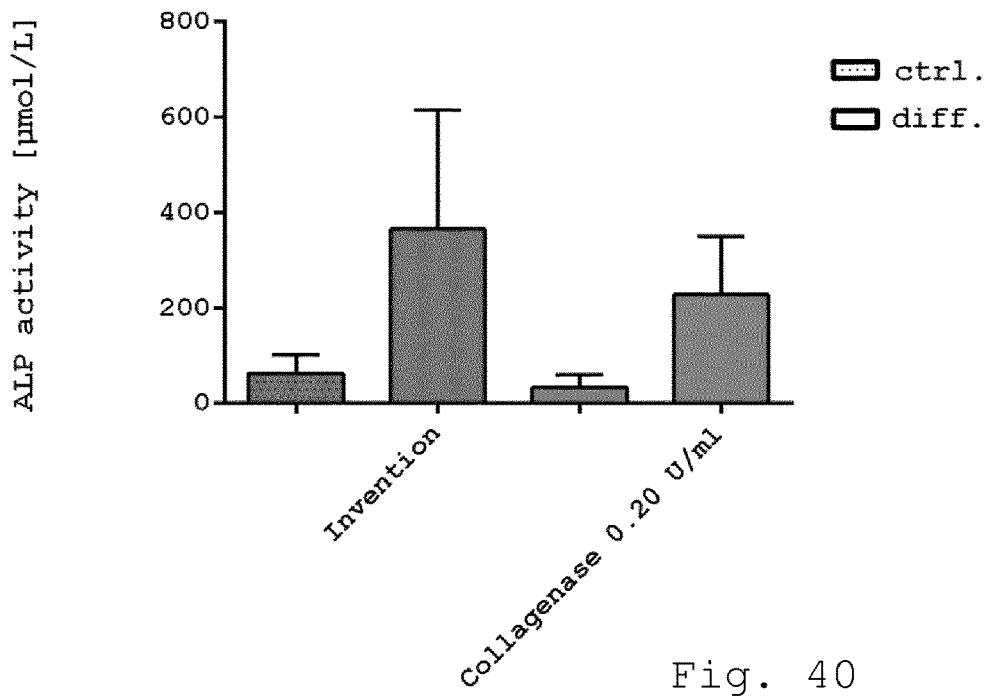
Figure 41:
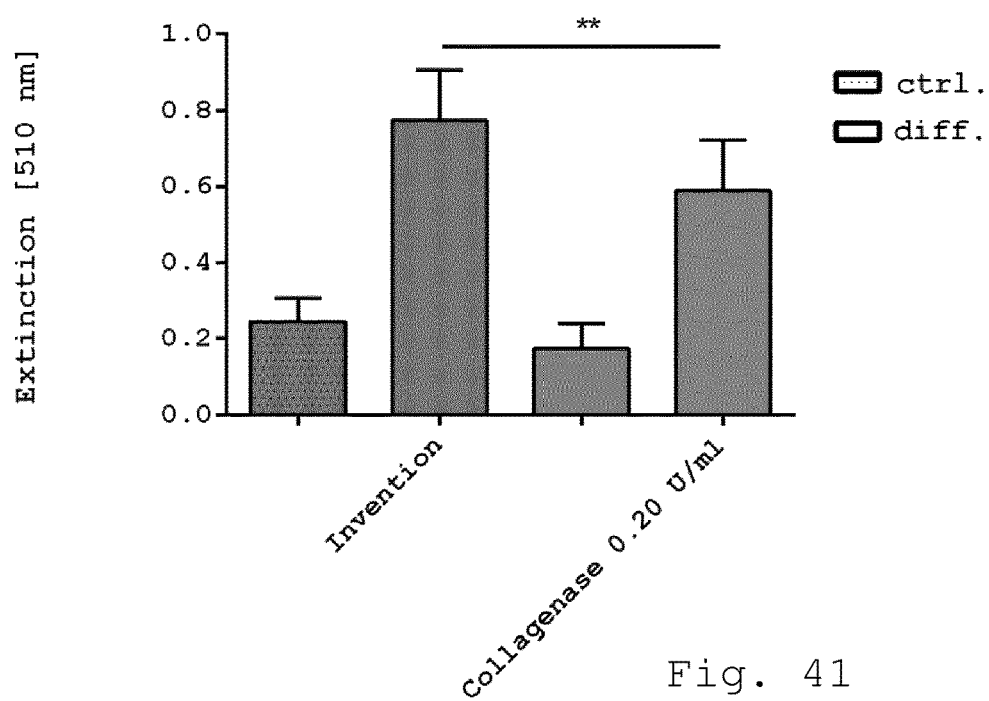
Figure 42A:
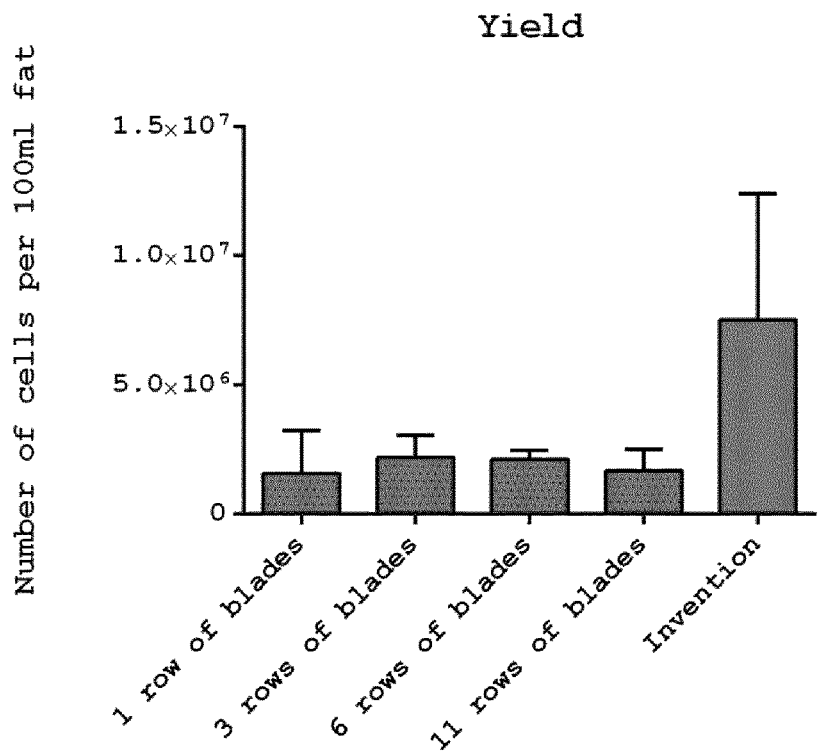
Figure 42B:
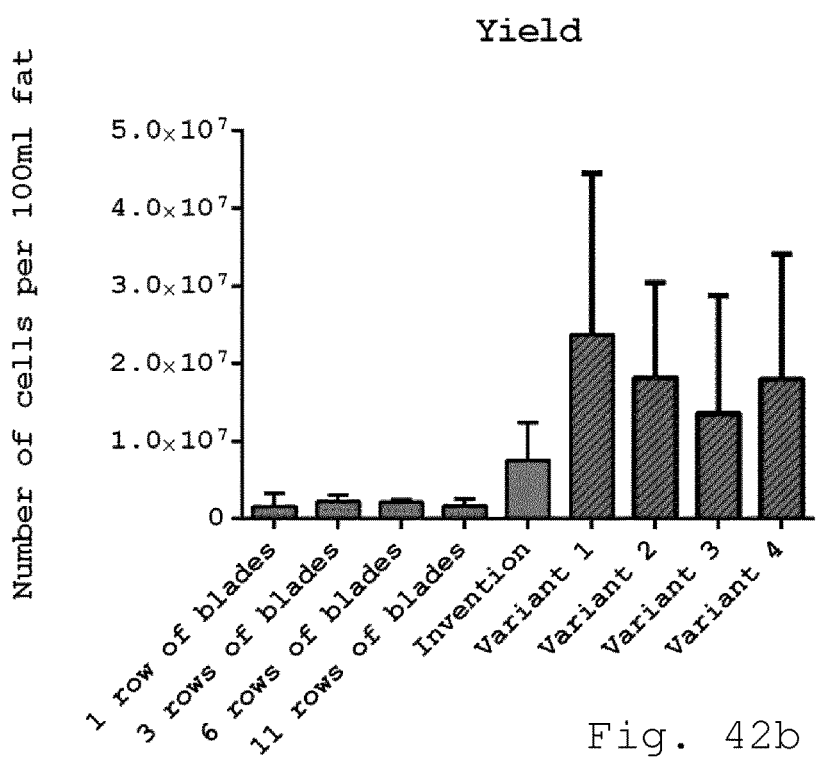
Figure 43A:
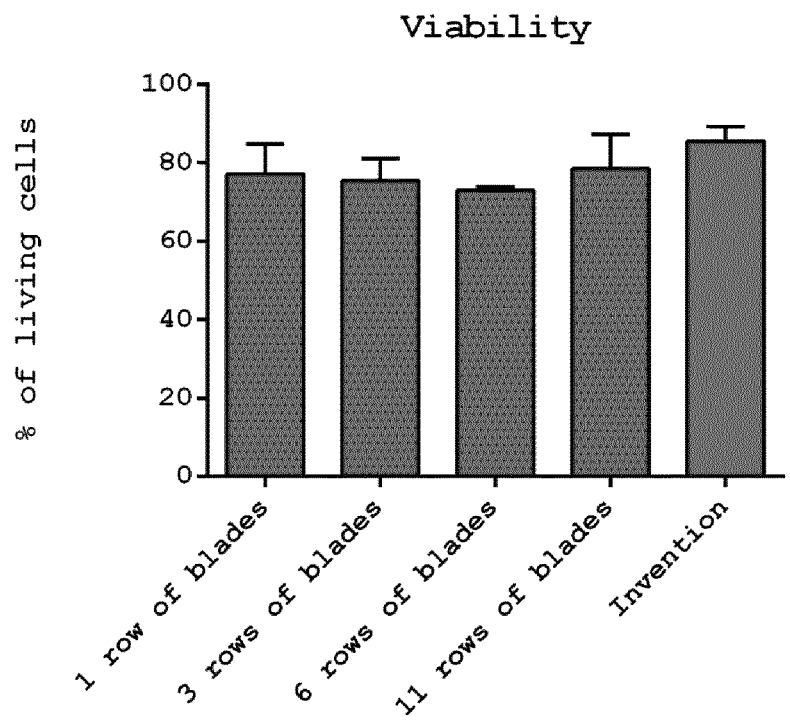
Figure 43B:
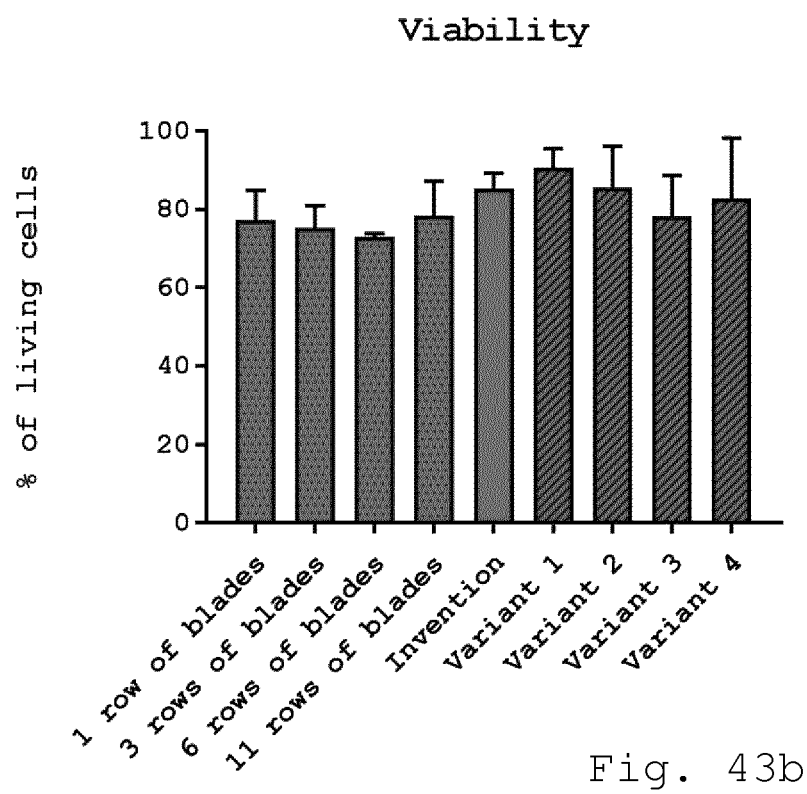

FIG. 22 shows the cell yield of freshly isolated therapeutic cells/microtissue from 100 ml liposuction material, wherein microtissue obtained with the enzymatic isolation method showed significantly higher cell yield compared to cells isolated after performing the inventive method or shaking and cutting method (***p<0.001. n=5-9);

FIG. 23 shows the cell viability of freshly isolated therapeutic cells/microtissue from 100 ml liposuction material, wherein the percentage of freshly isolated living cells derived from enzymatic and non-enzymatic isolation methods was examined by DAPI fluorescence staining. There were no significant differences in the cell viability between the applied enzymatic and non-enzymatic isolation methods. (n=5-9);

FIG. 24a shows representative pictures of a colony-forming unit fibroblast (CFU-F) assay of freshly isolated cells. Freshly isolated cells derived from enzymatic isolation (right-hand side) and according to the invention (left-hand side) were seeded in a defined number of cells in each well of a 6-well plate and after 14 days cultivation the formed colonies were stained with hematoxylin/eosin;

FIG. 24b shows the result of a quantitative analysis, which revealed that cells isolated according to the invention showed a higher potential to form colonies compared to cells obtained by the enzymatic isolation method (n=5);

FIG. 25 shows a diagram of intra-/extracellular ATP of adherent cells. Adherent cells derived from enzymatic and non-enzymatic isolation methods were examined for intra-/extracellular ATP concentration. Cells isolated according to the invention showed significant higher intra-/extracellular ATP concentration compared to the enzymatic isolation method and to the non-enzymatic isolation methods shaking and cutting (*p<0.05; p<0.01; *p<0.001; n=5);

FIGS. 26a and 26b illustrate the proliferation potential of adherent cells. Adherent cells derived from enzymatic and non-enzymatic isolation methods were examined after 3 and 7 days in expansion media by light microscopy (FIG. 26a) and after 7, 14 and 21 days in expansion media for their proliferation potential by population doubling level (PDL) (FIG. 26b). Cells derived from all isolation methods showed spindle-shaped cell morphology on day 7. Size bar=100 μm (FIG. 26a). Cells isolated after processing according to the invention showed similar PDL compared to the enzymatic isolation method or to the non-enzymatic isolation methods shaking and cutting (FIG. 26b) (n=5);

FIG. 27a-f show diagrams comparing the immunophenotype of freshly isolated cells. Freshly isolated cells derived from enzymatic isolation method (0.2 U/ml collagenase) and non-enzymatic isolation according to the invention were examined for cellular composition. While there was no difference in the mesenchymal stem cell marker CD73 (FIG. 27a), CD90 (FIG. 27b) and CD105 (FIG. 27c) endothelial progenitor cells (CD45−/CD31+/CD34+) (FIG. 27d) and pericyte like-cells (CD45−/CD31−/146+) (FIG. 27e) were slightly reduced when using the invention compared to enzymatic isolation. The number of SA-ASC (45−/31−/146−/34+) was enhanced when using the invention compared to enzymatic isolation (FIG. 27f). (n=3-4);

FIG. 28a-d show diagrams comparing the immunophenotype of adherent cells. Adherent cells derived with the invention or enzymatic isolation method (0.2 U/ml collagenase) were examined for cellular composition. While there was no difference in the mesenchymal stem cell marker CD73, CD90 and CD105 as well as the endothelial/pericytic marker CD146, an increase in the hematopoietic marker CD45 and the endothelial marker CD31 and CD34 was visible with the invention (FIG. 28a). Endothelial progenitor cells (CD45−/CD31+/CD34+) were significantly enhanced with the invention compared to enzymatic isolation (FIG. 28b). Also the number of pericyte like-cells (CD45−/CD31−/CD146+) was positively affected by the invention (FIG. 28c). The number of SA-ASC (CD45−/CD31−/146−/34+) was still high after 6 days in culture with the invention but lower than with enzymatic isolation (FIG. 28d). (**p<0.01. n=3);

FIG. 29 shows a diagram comparing the cytotoxicity of freshly isolated cells (LDH release). Cell death was assessed by LDH release after 24 h in expansion media. Cells derived using the invention and enzymatic isolation method (collagenase 0.2 U/ml) were compared to a control using Triton X-100 where 100% of the cells died. Cells derived from the inventive method showed significant lower LDH release compared to the enzymatic isolation method. ($p<0.01$; **$p<0.0001$. n=3);

FIGS. 30a and 30b illustrate a comparison of the osteogenic differentiation potential of adherent cells analyzed with Alizarin red staining (FIG. 30a) and quantification (FIG. 30b). Adherent cells derived by the invention, enzymatic and non-enzymatic isolation methods were examined after 1 week in expansion media and 3 more weeks in osteogenic differentiation media for their osteogenic differentiation potential stained with Alizarin red for matrix mineralization and calcification. Alizarin red staining demonstrated less mineralization for cells isolated with the enzymatic isolation method and the non-enzymatic isolation methods shaking and cutting but intense staining for cells derived with the invention. Size bar=100 μm (FIG. 30a). The quantitative analysis revealed that cells isolated with the invention showed significantly higher Alizarin red extinction compared to cells obtained by the enzymatic isolation method and the non-enzymatic isolation methods cutting and shaking (FIG. 30b). (Ctrl.: cells in control media without growth factors and stimuli, diff.: cells in osteogenic differentiation media. *$p<0.05$; ****$p<0.0001$. n=5);

FIG. 31 shows a diagram of the osteogenic differentiation potential of adherent cells analyzed with alkaline phosphatase (ALP). Adherent cells derived with the invention, enzymatic and non-enzymatic isolation methods were examined after 1 week in expansion media and 3 more weeks in osteogenic differentiation media for their osteogenic differentiation potential stained with ALP which is expressed in active osteoblasts. Cells isolated using the invention showed significant higher ALP activity compared to all other methods. (Ctrl.: cells in control media without growth factors and stimuli, diff.: cells in osteogenic differentiation media. *$p<0.05$. n=5);

FIGS. 32a and 32b illustrate a comparison of the adipogenic differentiation potential of adherent cells analyzed with Oil red O staining (FIG. 32a) and quantification (FIG. 32b). Adherent cells derived with the invention, enzymatic and non-enzymatic isolation methods were examined after 1 week in expansion media and 3 more weeks in adipogenic differentiation media for their adipogenic differentiation potential stained with Oil red O for lipid droplet formation. Oil red O staining demonstrated less lipid droplet formation for cells isolated with the enzymatic isolation method and the non-enzymatic isolation methods shaking and cutting but intense lipid droplet formation for cells derived by the invention. Size bar=100 μm (a). The quantitative analysis revealed that cells isolated with the invention showed significant higher Oil red O extinction compared to cells obtained by the enzymatic isolation method and the non-enzymatic isolation methods cutting and shaking (FIG. 32b). (Ctrl.: cells in control media without growth factors and stimuli, diff.: cells in adipogenic differentiation media. **$p<0.01$, n=5);

FIGS. 33a and 33b illustrate a comparison of the chondrogenic differentiation potential of 3D micromass pellets analyzed with Alcian blue and collagen type II staining (FIG. 33a) and increasing pellet size over time (FIG. 33b). Adherent cells derived with the invention, enzymatic and non-enzymatic isolation methods were transferred after 1 week in expansion media as 3D micromass pellets for 5 more weeks in chondrogenic differentiation media. The 3D micromass pellets were measured every week for their cross section area and after 5 weeks stained with Alcian blue and collagen type II for their chondrogenic differentiation potential. Alcian blue and collagen type II staining demonstrated weak or absent staining for cells isolated with the enzymatic isolation method and the non-enzymatic isolation methods shaking and cutting but intense staining for cells derived with the invention. Size bar=100 μm (FIG. 33a). Cells obtained with the invention showed a faster growth of pellet size in chondrogenic differentiation media compared to all other isolation methods (FIG. 33b). Asterisks indicate significant difference between invention and collagenase, addition signs indicate significant difference between invention and shaking and hashes indicate significant difference between invention and cutting. (*$p<0.05$; $p<0.01$; *$p<0.001$; ****$p<0.0001$. n=4);

FIG. 34 illustrates the vascularization potential of freshly isolated cells analyzed in 3D fibrin matrices. Freshly isolated cells derived from enzymatic isolation and with the invention were mixed with fibrinogen and thrombin for fibrin clot formation. After 2 weeks in expansion media including aprotinin they were analyzed for their vascularization potential with endothelial marker CD31 (green). The staining demonstrated development of tube-like morphology for cells derived from enzymatic isolation and with the invention. Size bar=200 μm (upper row), 100 μm (lower row). (n=1);

FIG. 35 shows the cell yield of freshly isolated therapeutic cells/microtissue from 100 ml liposuction material, wherein microtissue obtained with the enzymatic isolation method showed significantly higher cell yield compared to cells isolated with the inventive method and variations (i.e. variants 1-4 discussed below) of it (*$p<0.001$. n=5-8);

FIG. 36 shows the cell viability of freshly isolated therapeutic cells/microtissue from 100 ml liposuction material, wherein the percentage of freshly isolated living cells derived from enzymatic and non-enzymatic isolation methods were examined by DAPI fluorescence staining. There were no significant differences in the cell viability between the applied enzymatic and the inventive method and variations (i.e. variants 1-4 discussed below) of it. (n=5-10);

FIG. 37 shows the result of a quantitative analysis of a colony-forming unit fibroblast (CFU-F) assay of freshly isolated cells. Freshly isolated cells derived from enzymatic isolation method and the invention method were seeded in a defined number in each well of a 6-well plate and after 14 days cultivation the formed colonies were stained with hematoxylin/eosin. Cells isolated according to the invention showed a higher potential to form colonies compared to cells obtained by the enzymatic isolation method (n=9-16);

FIG. 38a-c show diagrams comparing the immunophenotype of freshly isolated cells. Freshly isolated cells derived from enzymatic isolation method (0.2 U/ml collagenase) and non-enzymatic isolation according to the invention were examined for cellular composition. While there was no difference in the number of endothelial progenitor cells (CD45−/CD31+/CD34+) (FIG. 34a) the number of pericyte like-cells (FIG. 34b) was slightly reduced when using the invention compared to enzymatic isolation. The number of SA-ASC was enhanced although not significant when using the invention compared to enzymatic isolation (FIG. 34c). (n=4);

FIG. 39 shows a diagram comparing the osteogenic differentiation potential of adherent cells analyzed with Alizarin red staining. Adherent cells derived by the invention, enzymatic and non-enzymatic isolation methods were examined after 1 week in expansion media and 3 more weeks in osteogenic differentiation media for their osteogenic differentiation potential stained with Alizarin red for matrix mineralization and calcification. Cells isolated with the invention showed significantly higher Alizarin red extinction compared to cells obtained by the enzymatic isolation method. (Ctrl.: cells in control media without growth factors and stimuli, diff.: cells in osteogenic differentiation media. ****$p<0.0001$. n=7);

FIG. 40 shows a diagram comparing the osteogenic differentiation potential of adherent cells analyzed with alkaline phosphatase (ALP). Adherent cells derived with the invention and enzymatic isolation methods were examined after 1 week in expansion media and 3 more weeks in osteogenic differentiation media for their osteogenic differentiation potential stained with ALP which is expressed in active osteoblasts. Cells isolated using the invention showed higher ALP activity compared to the enzymatic method. (Ctrl.: cells in control media without growth factors and stimuli, diff.: cells in osteogenic differentiation media. (n=5-8);

FIG. 41 shows a diagram comparing the adipogenic differentiation potential of adherent cells analyzed with Oil red O staining. Adherent cells derived with the invention, enzymatic and non-enzymatic isolation methods were examined after 1 week in expansion media and 3 more weeks in adipogenic differentiation media for their adipogenic differentiation potential stained with Oil red O for lipid droplet formation. Cells isolated with the invention showed significant higher Oil red O extinction compared to cells obtained by the enzymatic isolation method. (Ctrl.: cells in control media without growth factors and stimuli, diff.: cells in adipogenic differentiation media. **$p<0.01$. n=8);

FIGS. 42a and 42b show the cell yield of freshly isolated therapeutic cells/microtissue from 100 ml liposuction material, where the invention method shows higher cell yield compared to cells isolated with 1, 3, 6 and 11 rows of blades of the invention. FIG. 42b includes variants 1-4 (discussed below) in the comparison of FIG. 42a. (n=2-6);

FIGS. 43a and 43b show the cell viability of freshly isolated therapeutic cells/microtissue from 100 ml liposuction material, wherein the percentage of freshly isolated living cells derived from non-enzymatic isolation methods was examined by DAPI fluorescence staining. There were no significant differences in the cell viability between the applied invention method and cells isolated with 1, 3, 6 and 11 rows of blades of the invention. FIG. 43b includes variants 1-4 (discussed below) in the comparison of FIG. 43a. (n=2-6);

DISCUSSION OF FIGS. 1-7 AND 21

Figure 1:
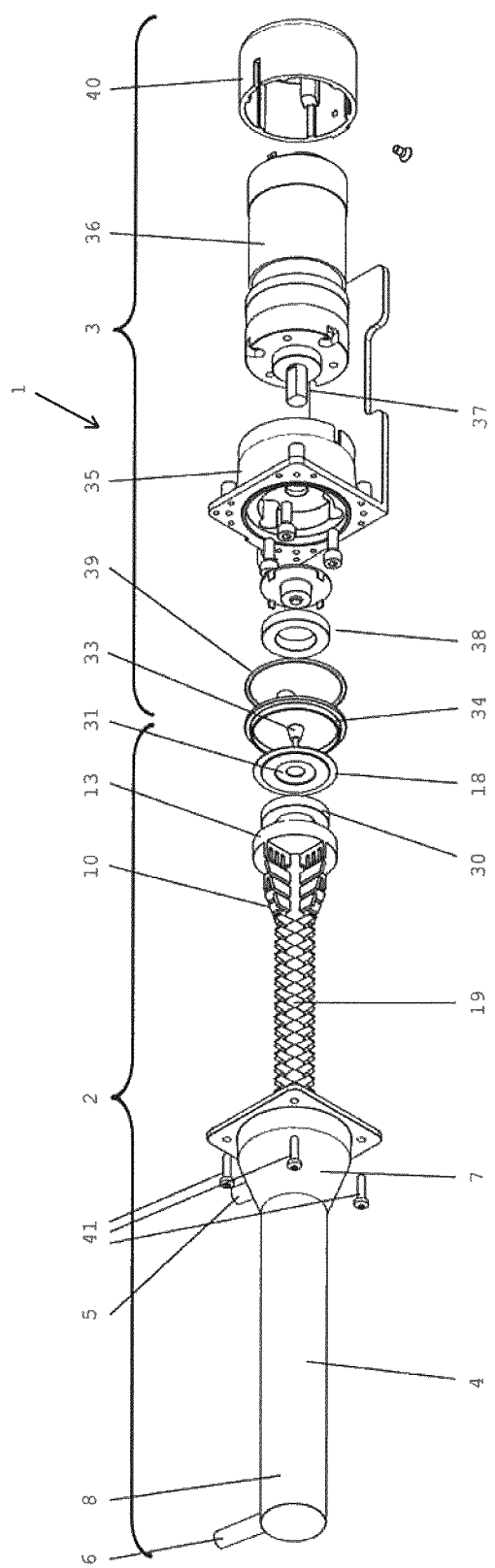
Figure 2:
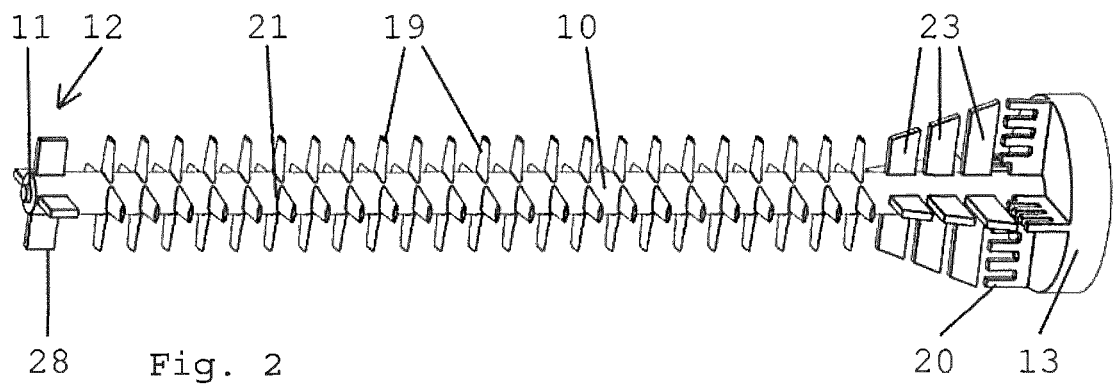
Figure 5:
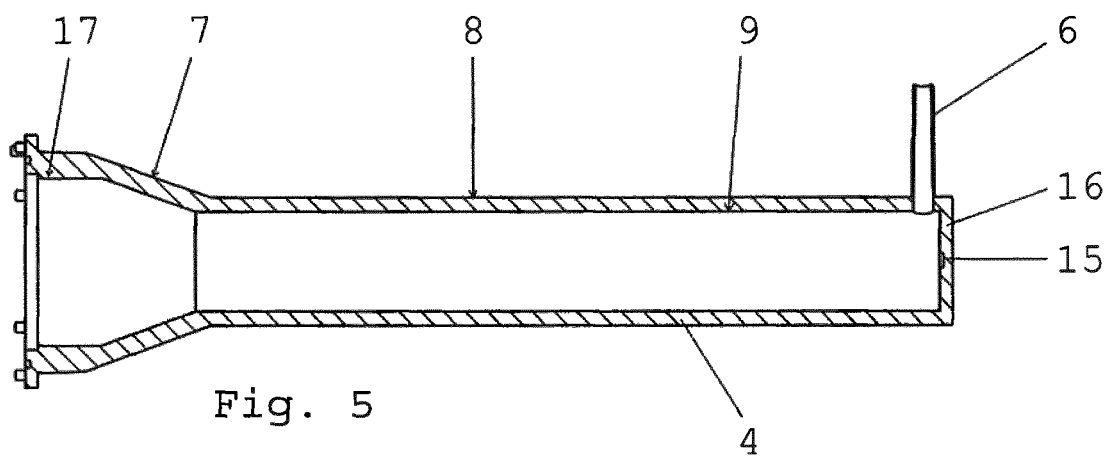
FIG. 5 and FIG. 6 show a cut and top view respectively of the casing of the milling device shown in FIG. 1.

FIG. 1 shows a processing device 1 comprising a milling device 2 and a drive unit 3. The milling device is configured for preparing therapeutic cells from adipose tissue. The milling device 2 comprises a casing 4 having an inlet 5 and an outlet 6. The casing 4 has a tapered section 7 close to the inlet 5. The tapered section 7 leads to a cylindrical section 8 of the casing 4, from which the outlet 6 extends radially. The casing 4 defines an operating volume 9 on its inside (cf. FIG. 5), having a partially tapered and partially cylindrical shape according to the respective sections 7, 8 of the casing 4. The milling device 2 further comprises a rotor 10. The rotor 10 is adapted to be rotatably received within the operating volume 9 of the casing 4. The rotor 10 has an axle pin 11 on its narrow end 12 for supporting the rotor 10 inside the casing 4 and a coupler disk 13 on its wide end 14. When received in the operating volume 9, the narrow end 12 is provided near the outlet 6 whereas the wide end 14 is provided near the inlet 5 of the casing 4. In operation, the axle pin 11 is received in a bearing recess 15 on the inside of an end plate 16 of the casing 4 (see FIG. 5) and the coupler disk 13 is essentially flush with an opening 17 of the casing on the side opposite the end plate 16. The axial length of the axle pin 11 is e.g. 0.9 mm. The diameter of the coupler disk 13 is e.g. 33 mm at a total height of 7 mm. The rotor 10 is pivotable with respect to the casing 4 around an axis of rotation 18. The rotor 10 comprises 28 (twenty-eight) rows of blades 19 in a spaced arrangement with respect to the axis of rotation 18 (see FIG. 3). The overall length of the rotor in axial direction (i.e. parallel to the axis of rotation 18) is about 186 mm. The inlet 5 and the outlet 6 are offset in a direction parallel to the axis of rotation 18 of the rotor 10.

The first blade row 20 when coming from the inlet on the wide end 14 of the rotor 10 is in contact with the coupler disk 13. It comprises four blades each extending radially outward from a central elongate shaft 21 of the rotor 10 and with a midplane essentially parallel to the axis of rotation 18, i.e. with outer edges arranged cylindrically around the shaft 21. The blades are arranged circumferentially with respect to the axis of rotation 18 at different azimuthal angles, i.e. at 0°, 90°, 180° and 270° (see FIG. 4). The diameter of the shaft 21 is e.g. 7 mm and the width of the first blade row 20 is for example 7.5 mm. The four blades of the first blade row 20 each comprise four radially spaced teeth 22, which extend essentially parallel to the axis of rotation 18. The width of the teeth 22 in radial direction varies between 1.4 and 1.8 mm.

The second, third and fourth blade rows 23 each have four circumferentially arranged blades that are essentially parallel to the blades of the first blade row 20. The radially outer ends of the blades of the second, third and fourth blade row 23 are essentially flush with the inner wall of the tapered section 7 of the casing 4, i.e. said radially outer edges are inclined with respect to the axis of rotation 18 of the rotor 10. In other words the outer edges are arranged conically with respect to the axial direction. The first four blade rows 20, 23 are axially separated by gaps 24, which are smaller than the width of the blades of the respective blade rows 20, 23 in axial direction. For instance the width of the blades of the second, third and fourth blade rows 23 may be 5 mm and the width of the gaps 24 between them may be 1.7 mm. The blades of the first four blade rows 20, 23 together form a first group 25 of blades. The blades of the first group 25 are mainly used for homogenization of the tissue introduced through the inlet 5 and to set the tissue in rotation.

The blades of the fifth and up to the 27th blade row form a second group 26 of blades. The blades of this second group 26 are orientated normal to the axis of rotation 18 such that the axis of rotation 18 is essentially perpendicular to the midplane of the blades, i.e. the midplane is parallel to the plane of movement of the blades. The blades of the second group 26 have a roughly elliptical cross-section and are tapered in radial direction. The blades have their maximum width perpendicular to the midplane at the end connected to the shaft 21. This maximum width is about 1.3 mm compared to a minimum width of 0.4 mm at the radially outer end of the blade. The distance of the blades of the second group 26 is about 6 mm, resulting in a width of between 4 and 5 mm of the gaps 27 between the blades.

At the narrow end 12 of the rotor 10 a final blade row 28 is connected to the shaft 21. The four blades of this final blade row 28 are orientated with their midplanes parallel to the axis of rotation 18, similar to the first group 25 of blades. This orientation promotes the ejection of the processed cells and tissue through the outlet 6 adjacent said final blade row 28 by centrifugal force. The length of the blades of the second group 26 and the final blade row 28 measured from the shaft 21 in radial direction is about 6.3 mm, such that the total diameter of the rotor in this region is about 19.5 mm.

Figure 3:
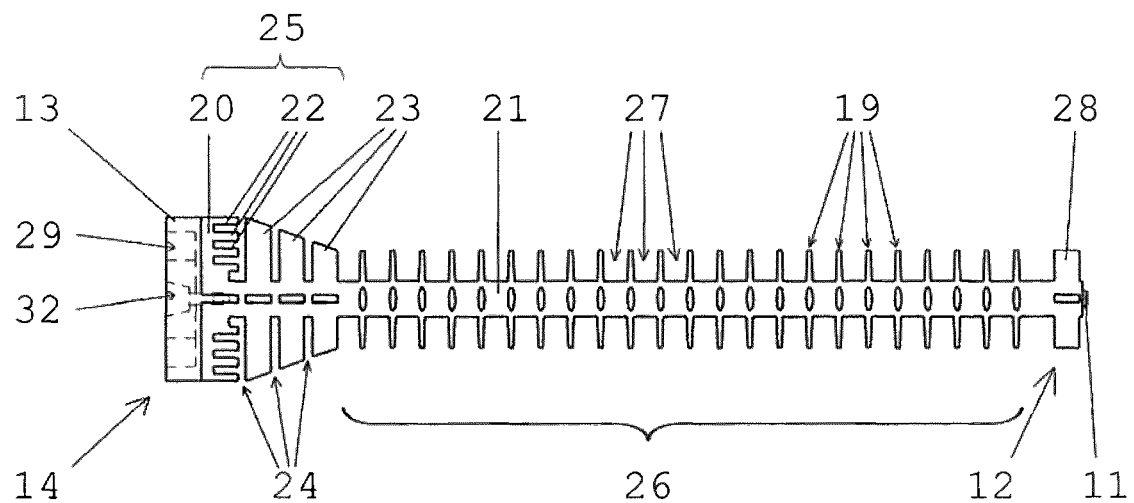
FIG. 3 and FIG. 4 show a side view and top view respectively of the rotor of FIG. 2.
Figure 4:
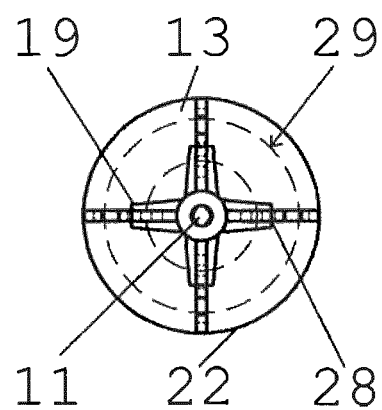

The coupler disk 13 of the rotor 10 has a ring-shaped recess 29 in its outer surface, i.e. facing away from the shaft 21 (s. FIGS. 3 and 4). The ring-shaped recess 29 is configured for receiving a magnetic ring 30, which is part of a magnetic coupling of the rotor 10 to the drive unit 3 (s. FIG. 1). The magnetic ring 30 is held in place by a disk cover 31 attached to the coupler disk 13 and sealing the recess 29. The coupler disk 13 further has a central recess 32 for receiving an axle pin 33 of a sealing washer 34 through a central opening in the disk cover 31. The sealing washer 34 is attached and fixed to the casing 4 to confine and seal the operating volume 9. This construction ensures a sterile closed system. The axle pin 33 of the sealing washer 34 and the bearing recess 15 of the casing 4 together provide the pivot bearing at both ends of the rotor 10. Thus in the present example, the milling device 2 is formed by the casing 4, the rotor 10 and the sealing washer 34, optionally together with the magnetic ring 30 and the disk cover 31 for providing a suitable coupling for driving the rotor 10.

On the outside of the sealing washer 34, i.e. on the side opposite the operating volume 9, the milling device 2 is connected to the drive unit 3. Specifically the casing 4 is fixed to a drive casing 35, which encases a drive 36 formed e.g. by an electrical motor. The drive shaft 37 of the drive 36 is fixed to a second magnetic ring 38, which is arranged opposite the magnetic ring 30 of the rotor 10 in axial direction. The magnetic rings 30, 38 are configured such as to provide a magnetic coupling across the sealing washer 34 and the disk cover 31, wherein the magnetic coupling provides for a transmission of torque applied by the drive 36 to the rotor 10. In order to avoid liquid components of the processed tissue from entering the drive casing 35, an additional seal ring 39 is arranged between the sealing washer 34 and the drive casing 35. The back of the drive casing 35 facing away from the milling device 2 is closed by an end cap 40 attached to the drive casing 35.

The milling device 2 as described above effectively forms a milling cartridge that is removably attached to the drive unit 3 by releasable fixing means 41 such as screws.

Figure 6:
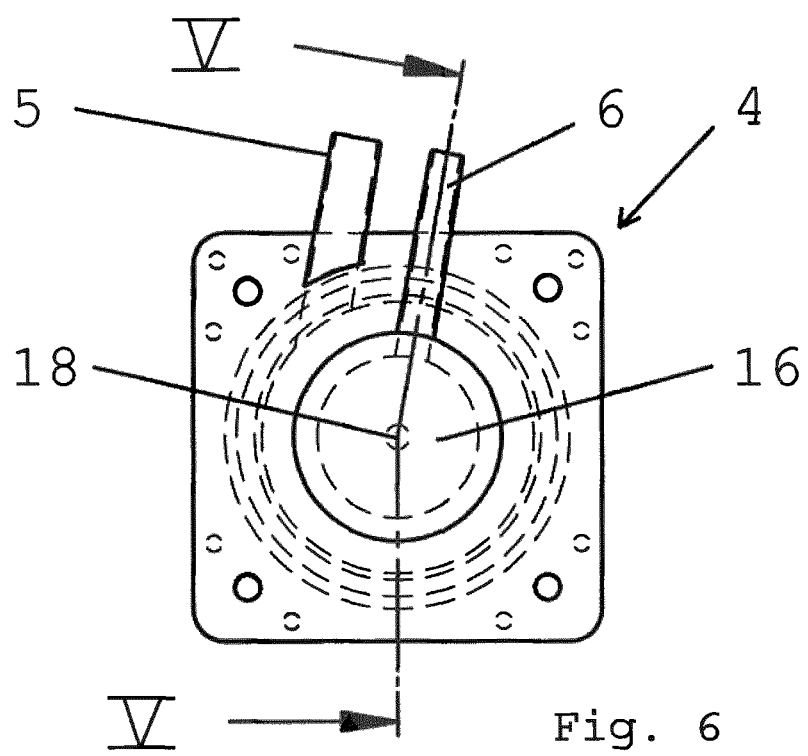

In FIG. 6 the arrangement of the inlet 7 and outlet 6 with respect to the axis of rotation 18 is apparent. Specifically the inlet 5 is provided in a partially tangential arrangement, i.e. offset from the center of the casing 4 and the axis of rotation 18, and such as to guide the introduced tissue in a tangential path onto the first row 20 of blades of the rotor 10. The outlet on the other hand is centered with respect to the operating volume 9 of the casing 4 and extends radially outwards from the axis of rotation 18. This arrangement is most efficient to exploit the centrifugal forces acting on the processed tissue and cells due to the rotation applied by the final row 28 of blades.

Figure 7:
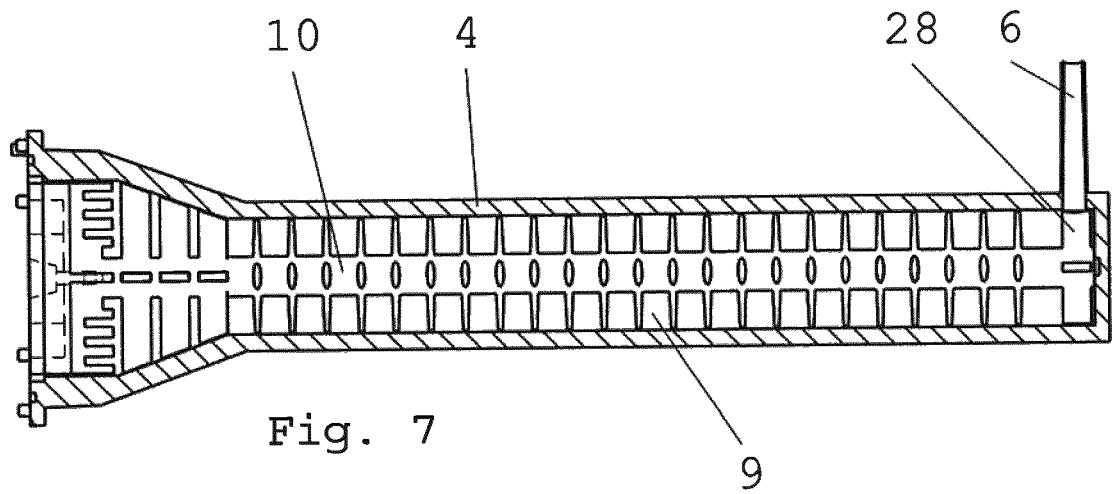
FIG. 7 shows a partial cut view of an assembled milling device comprising a rotor according to FIG. 3 and a casing according to FIG. 5.

FIG. 7 shows the casing 4 together with the rotor 10 received in the operating volume 9 of the casing 4. As is apparent from this view, the outer edges of the blades of all rows of the rotor 10 are essentially flush with the inner wall of the casing 4 delimiting the operating volume 9, such that there is no path for the tissue to avoid contact with the blades. The position and width of the final blade row 28 is adapted to the position and width of the outlet 6 such that the opening of the outlet 6 is basically wiped by the blades of the final blade row 28.

The above preferred embodiment is by no means limiting. The skilled person will readily anticipate from the above description that the blades may have different shapes and arrangements, such as e.g. an essentially constant cross section or a curved arrangement with respect to a radial direction, and a different number and sequence of blades having a parallel, normal and/or inclined arrangement with respect to the axial direction may be used.

FIG. 21 shows a set 42 for liposuction applications. The set 42 comprises a milling device 2 (only partially shown) and a cannula 43. The cannula 43 is connected to an inlet 5 of the milling device 2 by tubing 44. The tubing 44 may accommodate a roller pump or peristaltic pump (not shown). The cannula 43 is schematically illustrated with a needle 45 for use in liposuction.

Four additional variants of the original variant (variant 0, also indicated as "invention" albeit without limitation of the present invention to this variant) discussed above have been tested and will be discussed below: The variant 1 of the invention has a greater shaft diameter and shorter blades than the original variant: the diameter of the shaft 21 is about 13 mm (simplifying casting of the rotor compared to the first embodiment) and the length of the blades of the second group 26 and of the final blade row 28 measured from the shaft 21 in radial direction is about 3 mm, such that the total diameter of the rotor in this region is about 19 mm. The variant 2 has the same specification as variant 1, but every other blade row is shifted by 45 degrees about the axis of rotation of the rotor. The variant 3 has a greater shaft diameter and the same blade length as the original variant: the diameter of the shaft 21 is about 13 mm and all blades have a similar length which is about 6 mm measured from the shaft 21 in radial direction, such that the total diameter of the rotor is about constant over the entire length and amounts to about 25 mm. The variant 4 has the same specification as variant 3, but every other blade row is shifted by 45 degrees about the axis of rotation of the rotor. The dead volume of the original variant is about 71 ml, the dead volume of variants 1 and 2 is about 55 ml (due to the larger volume filled by the shaft) and the dead volume of variants 3 and 4 is about 136 ml (due to the larger operating volume inside the casing).

General Remarks

In order to evaluate the performance of the present method and device, a comparative study has been carried out comparing the quality of the cells resulting from the present method and using the present device with cells obtained using methods and devices according to the prior art. The steps described below in more detail are described for illustration of the comparative study and for understanding of the presented results. Those steps are not limiting to the inventive method. In order to obtain useable cells in practice it suffices to centrifuge the processed tissue withdrawn from the milling device according to the invention.

The collection of human adipose tissue was approved by the local ethical board with patient's consent. Subcutaneous adipose tissue was obtained during routine outpatient liposuction procedures under local tumescence anaesthesia. 100 ml adipose tissue followed by 100 ml phosphate-buffered saline (PBS; Lonza, Austria) were transported through a single use milling device 2 as described in connection with FIGS. 1 to 7. The suspension of homogeneous adipose tissue, separated cells and PBS was drawn from the outlet 6 of the milling device 2 and collected in a sterile container.

During cell isolation all processes were performed in a sterile workbench. Homogenized adipose tissue obtained using the present method was transferred into sterile 50 ml-tubes. After centrifugation at 1200 g for 7 min the cell pellet was incubated with 100 ml erythrocyte lysis buffer (154 mM ammonium chloride (Sigma, Austria), 10 mM potassium bicarbonate (Sigma), 0.1 mM ethylenediaminetetraacetic acid (EDTA; Biochrom, Austria) in aqua dest for 5 min at 37° C. to eliminate red blood cells. The supernatant was aspirated after centrifugation for 5 min at 500 g. The pellet was washed with PBS and filtered through a 100-μm cell strainer (Falcon, Austria). After another centrifugation step at 300 g for 5 min the supernatant was removed and the isolated cells were cultured in endothelial growth media (EGM-2; Lonza) at 37° C., 5% $CO_2$, and 95% air humidity or resuspended in EGM-2 for further analyses.

For comparison a non-enzymatic cell isolation using shaking method was modified from US 2014/0017783 A1 (Gimble, J. M., et al., Non-Enzymatic Method for Isolating Human Adipose-Derived Stromal Stem Cells. 2014, US 20140017783 A1 also Shah, F. S., et al., A non-enzymatic method for isolating human adipose tissue-derived stromal stem cells. Cytotherapy, 2013. 15(8): p. 979-85). 100 ml liposuction material was transferred into a 250 ml-bottle and extensively washed with 50 ml PBS by manual shaking the bottle. This process was repeated for three times, each time with 50 ml PBS. Afterwards, the processed lipoaspirate and PBS was transferred into 50 ml-tubes and treated as described before for the homogenized adipose tissue obtained using the method according to the invention.

Moreover a non-enzymatic cells isolation using cutting method has been carried out for comparison. Based on the Adipofilling method (Capurro, S., Adipofilling. 2007; Available from: www.adipofilling.com) 100 ml liposuction material was transferred into a beaker and cut with a hand blender for 2 min. Afterwards, the hand blender was washed with 50 ml PBS, which was collected in the same beaker. The processed lipoaspirate was transferred into 50 ml-tubes and treated as described before for the homogenized adipose tissue obtained using the method according to the invention.

Enzymatic isolation of cells was performed as modified from Wolbank et al. (Wolbank, S., et al., Dose-dependent immunomodulatory effect of human stem cells from amniotic membrane: a comparison with human mesenchymal stem cells from adipose tissue. Tissue Eng, 2007. 13(6): p. 1173-83). Briefly, 100 ml liposuction material was washed with an equal volume of PBS to remove blood and tumescence solution. Afterwards tissue was digested with 100 ml collagenase NB4 (Serva, Austria) with a concentration of 0.2 U/ml dissolved in PBS containing $Ca^{2+}/Mg^{2+}$ and 25 mM N-2-hydroxyethylpiperazine-N0-2-ethanesulfonic acid (HEPES; Sigma) at 37° C. under moderate shaking (180 rpm) for 1 h. The digested tissue was transferred into 50 ml-tubes and treated as described before for the homogenized adipose tissue obtained using the method according to the invention.

After seeding the cells on plastic surface in expansion media (EGM-2), the adherent cell fraction including ASC can outgrow as adherent monolayer and are cultured to a subconfluent state before passaging. Media was changed every 3 to 4 days. For subcultivation EGM-2 media was aspirated, cells were washed with PBS and incubated with 1× trypsin/EDTA at 37° C. After 2-5 min and gentle tapping of the culture flask, cells were detached and the activity of trypsin was stopped by adding media with 10% fetal calf serum (FCS; PAA, Austria). The dissociated cells were collected in a tube and centrifuged. Thereafter, the pellet was resuspended in EGM-2 media and cells were quantified with trypan blue exclusion in a cell counter (TC-20, Biorad, Austria). Adherent cells from passage 0 were used for ATP, flow cytometry analysis and differentiation potential, whereas freshly isolated cells were used for all other experiments.

Discussion of FIG. 8-20

Cell number and viability was determined using Acridine Orange/DAPI fluorescence staining and quantified in a cell counter (NucleoCounter® NC-200™, Chemometec, Denmark) with integrated fluorescence microscope. Since the heterogeneous cell composition consists also of aggregated cells on remaining extracellular matrix strands the "Viability and Cell Count—Aggregated Cells Assay" protocol was chosen. Each sample was transferred into a Via1-Cassette™, which is coated with Acridine Orange and DAPI and two measurements were performed: One with cell lysis solution to stain all cell nuclei in the sample and one without lysis solution to stain only non-viable cells.

A defined number of cells (4, 20, 100, 500, 2500, 12500) was seeded in each well of a 6-well plate and were cultured in EGM-2 for 14 days, including one media change at day 7. After 14 days of culture single cells have formed colonies. Cells were fixed with 4% formaldehyde and stained with hematoxylin. Afterwards, the cells were washed with tap water and stained with eosin solution. The percentage of cells that formed visible colonies (in the well with 500 seeded cells) was calculated and compared to the total seeded cells.

The amount of intra-/extracellular ATP is an indicator for energy production of cells. To determine the intra-/extracellular ATP concentration CellTiter-Glo® Luminescent Cell Viability Assay (Promega, Austria) was used and performed according to the manufacturer's instructions. Cells were seeded at a density of $1 \times 10^4$ cells per well in a black 96-well plate (Greiner, Austria) in 100 μl EGM-2 media. After 2 h, 100 μl CellTiter-Glo® Reagent were added to each well and the plate was gently agitated on a shaker for 2 min. Afterwards the plate was incubated for 10 min in the dark. The combination of intracellular and extracellular ATP can be measured since CellTiter-Glo® Reagent includes a cell lysis buffer. The luminescent signal was detected with a luminometer (Tecan, Austria) at an exposure time of 2000 ms and correlated to an ATP standard curve.

Proliferation potential was analyzed by determining the population doubling level (PDL). Freshly isolated cells were seeded at a density of $5 \times 10^5$ cells per T-25 culture flask and cultured in EGM-2 media. Media was changed every 3 to 4 days. When cells had reached a subconfluent state they were passaged and cell number was determined as described above. For further analysis of PDL, ASC were seeded at a density of $5 \times 10^4$ in T-25 culture flasks and cultured until passage 3. Cell number was determined after each passage.

Freshly isolated and adherent cells from day 6 of culture were characterized using the following antibodies CD73-FITC (eBiosciences, Austria), CD90-PE (eBiosciences), CD105-V450 Horizon (BD, Austria), CD45-V500 Horizon (BD), CD31-FITC (eBiosciences), CD34-APC (BD) and CD146-PerCP (R&D, Austria) as well as the combination of CD45, CD31, CD34 and CD146 to analyze specific subpopulations: endothelial progenitor cells (CD45−/CD31+/CD34+), pericyte like-cells (CD45−/CD31−/CD146+), and supra-adventitial ASC (SA-ASC) (CD45−/CD31−/CD146−/CD34+).

For staining, $2.5 \times 10^5$ cells in 50 μL PBS with 1% FCS were incubated with 5 μl primary labeled antibodies at room temperature for 15 min in the dark. Cells were washed with 1.5 ml Cell Wash (BD) and centrifuged for 5 min at 400 g. The supernatant was discarded and the cell pellet resuspended in 300 μL 1×Cell Fix (BD; diluted 1:10 with aqua dest). Samples were stored at 4° C. in the dark until analysis on a FACSAria II (BD). Percentage of marker positive cells was determined, compared to a non-specific isotype control.

For quantification of lactate dehydrogenase (LDH) release cellular supernatants were analyzed using Cytotoxicity Detection Kit (Roche, Austria). Freshly non-enzymatic (obtained using the invention) and enzymatic (collagenase 0.2 U/ml) isolated cells were seeded at a density of $2\times10^4$ in a 96-well plate in 200 µl EGM-2 and incubated for 24 h. Enzymatic isolated cells seeded in 100 µl EGM-2 and 100 µl Triton X-100 were used as control for 100% dead cells. After an incubation of 24 h 100 µl of each supernatant was transferred into a new well and 100 µl Reaction mixture was added for 0.5 h. Absorbance was measured with a luminometer (Tecan, Austria) at 490 nm and after subtraction of a reference value at 650 nm it was normalized to positive control Triton X-100, which lyses the cells.

For osteogenic differentiation, cells were seeded at a density of $2\times10^3$ cells per well in a 24-well plate in EGM-2 media and incubated overnight. On the next day, media was changed to osteogenic differentiation media DMEM-low glucose (Lonza) containing 10% FCS, 2 mM L-glutamine (PAA), 100 U/ml Pen/Strep (Lonza), 10 nM dexamethasone (Sigma), 150 µM ascorbat-2-phosphate (Sigma), 10 mM β-glycerophosphate (StemCell Technologies, Germany) and 10 nM dihydroxy-vitamin D3 (Sigma) or control media consisting of DMEM:F12/L-glutamine (Lonza) with 10% FCS and 100 U/ml Pen/Strep. Media was changed every 3 to 4 days.

After 21 days, osteogenic differentiation was analyzed with Alizarin Red staining and quantification, as well as determination of intracellular alkaline phosphatase (ALP) activity.

For Alizarin Red staining of calcified structures, cells were washed with PBS and fixed for 1 h with 70% ethanol at −20° C. After rinsing the fixed cells with aqua dest, cells were stained with 40 mM Alizarin Red solution (pH 4.2; Merck, Austria) for 15 min. The cells were washed with PBS and representative images were taken under the light microscope. For quantitative analysis of Alizarin Red staining, the supernatant was discarded and the cells were incubated with 500 µl 20% methanol and 10% acidic acid (diluted in aqua dest) for 15 min. After resuspension, the mixture of cells and methanol/acidic acid was transferred to a transparent 96-well plate (100 µl per well). The absorbance was measured at 450 nm with a luminometer.

The second method to analyze osteogenic differentiation is the detection of the activity of intracellular alkaline phosphatase (ALP), which is located on the surface of osteoblast cells and has been shown to be a biochemical indicator of bone maturation, mineralization and bone turnover. First, osteogenic media was discarded and the cells were incubated with 100 µl PBS for 1 h at −20° C. Afterwards, the cells were lysed for 1 h by addition of 100 µl PBS containing 0.5% TritonX-100 (Sigma). For quantitative detection of ALP activity, 100 µl substrate solution (4-nitrophenylphosphate) were added in each well and incubated for 1 h in the dark. Finally, the solution was transferred to a transparent 96-well plate (100 µl per well) and absorbance was measured at 405 nm together with a reference wavelength of 620 nm in a luminometer. By creating a standard curve with known p-nitrophenol concentrations diluted in stop solution (0.5% TritonX-100 diluted in PBS 1:2) and measuring the corresponding absorption, the ALP activity of the samples can be calculated.

For adipogenic differentiation, cells were seeded at a density of $1.4\times10^4$ cells per well in a 24-well plate in EGM-2 media and incubated overnight. On the next day, media was changed to adipogenic differentiation media DMEM-high glucose (Lonza) containing 10% FCS, 2 mM L-glutamine, 100 U/ml Pen/Strep, 1 µM dexamethasone, 0.5 mM 3-isobutyl-1-methylxanthine (IBMX; Sigma), 10 µg/ml insulin (Sigma) and 100 µM indomethacin (Sigma) or control media consisting of DMEM:F12/L-glutamine with 10% FCS and 100 U/ml Pen/Strep. Media was changed every 3 to 4 days.

After 21 days, adipogenic differentiation was analyzed with Oil Red O staining and quantification. An Oil Red O stock solution was prepared by dissolving 0.3 g Oil red O (Sigma) in 100 ml isopropanol (Merck, Germany) at 50-60° C. For the working solution the filtered stock solution was diluted in aqua dest 3:2. After 30 min the working solution was filtered once again immediately before usage. The cells were washed with PBS and fixed with 4% formaldehyde for 1 h. After washing with aqua dest, the cells were rinsed with 70% ethanol for 2 min and stained for 5-15 min with Oil Red O working solution. Then the cells were washed with aqua dest and counterstained for 1-3 min with Mayer's haematoxylin solution. Finally, the cells were washed with tap water and evaluated under the light microscope. For quantitative detection of Oil Red O staining, the supernatant was discarded and 500 µl isopropanol were added in each well. After resuspension, the mixture of cells and isopropanol was transferred to a transparent 96-well plate (100 µl per well). The absorbance was measured at 510 nm with a luminometer.

For chondrogenic differentiation and 3D micromass pellet cultures, $3\times10^5$ ASC were centrifuged in chondrogenic differentiation media (hMSC Chondro BulletKit (Lonza) containing 10 ng/ml BMP-6 (R&D) and 10 ng/ml TGF-ß3 (Lonza) in screw cap micro tubes. The tubes were placed in an incubator at 37° C., 5% CO2, and 95% humidity with slightly open cap for gas exchange. After 2 days the pellets were transferred to 96-well U-bottom plates (Greiner) with fresh media. Media was changed every 2 to 3 days. The 3D micromass pellet cultures incubated over 35 days in chondrogenic differentiation media were measured once a week for their cross section area. After 35 days of differentiation, micromass pellets were fixed in 4% phosphate-buffered formalin overnight for histological analysis. The next day the pellets were washed in 1× PBS and dehydrated in increasing concentrations of alcohol. After rinsing the pellets in xylol and infiltration with paraffin, deparaffinized sections were stained with Alcian blue for 30 min and counterstained for 2 min with Mayer's haematoxylin. For collagen type II staining, sections were treated with pepsin for 10 min at 37° C. (AP-9007 RTU, Thermo Scientific, Austria). Endogenous peroxidase was quenched with freshly prepared 3% H2O2 for 10 min at room temperature, followed by normal horse serum 2.5% (Vector RTU) to block unspecific binding. Sections were incubated 1 h with monoclonal anti-collagen type II (MS-306 P0 Thermo Scientific) at 1:100. After washing with TBS, sections were incubated with the secondary antibody (anti mouse DAKO EnVision+ System HRP labelled Polymer, Dako, Austria) for 30 min and rinsed in TBS again. Bindings were visualized using Nova Red (SK4800 Vector Labs, Austria) for 6 min. Counterstaining was performed with Mayer's haematoxylin for 2 min.

For determination of the vascularization potential of adipose tissue-derived cells a fibrin clot culture was performed according to Holnthoner et al. (Holnthoner, W., et al. 2015 as cited above) $4\times10^5$ cells were mixed with fibrinogen (Baxter, Austria; 2.5 mg/ml) and thrombin (Baxter, 0.2

U/ml) for clot formation and pipetted on coverslips in 12-well plates. Clots were polymerized at 37° C. for 30 min and cultured for 2 weeks in EGM-2 containing aprotinin (Baxter, 100 KIU/ml). Media was changed every 3-4 days. After cultivation clots were fixed with 4% PFA, washed with PBS and incubated with a FITC-conjugated monoclonal mouse anti-human CD31 antibody (BD Biosciences; 1:50 dilution in PBS/1% BSA) for 12 hours in the dark. Clots were again washed with PBS and images were taken on a Zeiss Axiovert 200M fluorescence microscope.

Data are presented as mean±standard deviation and statistical analysis was performed using PRISM6 (GraphPad, San Diego, Calif., USA), one-way ANOVA Tukey's post hoc. Statistical analysis of the pellet size was performed using two-way ANOVA Tukey's post hoc. Flow cytometry and CFU-F assay statistical analysis was performed using unpaired t-test. P values of <0.05 were considered to be significant.

Figure 8:
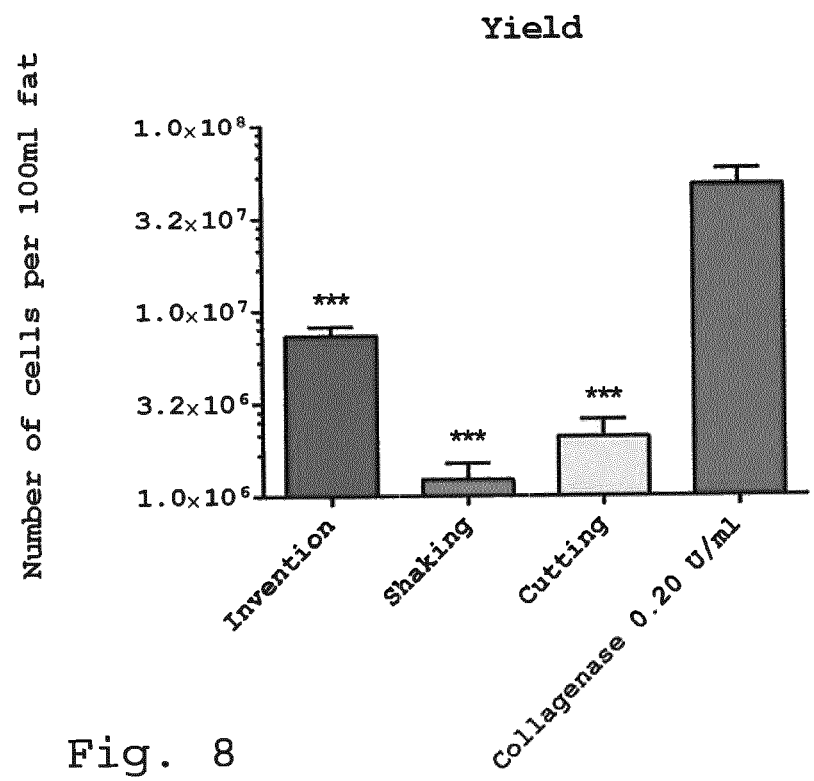
FIG. 8 shows the cell yield of freshly isolated therapeutic cells/microtissue from 100 ml liposuction material, wherein microtissue obtained with the enzymatic isolation method showed significantly higher cell yield compared to cells isolated after performing the inventive method or shaking and cutting method (***$p<0.001$. n=5-7)

The cell yield of freshly isolated cells was significantly higher after enzymatic isolation with $4.8\pm3.1\times10^7$ cells derived from 100 ml lipoaspirate compared to all non-enzymatic isolation methods (FIG. 8). The method according to the present invention resulted in a cell yield of $7.4\pm2.6\times10^6$ cells, while shaking and cutting method reached lower cell numbers of $1.2\pm0.6\times10^6$ and $2.1\pm1.2\times10^6$, respectively. However, cell viability of freshly isolated cells was similar in all applied enzymatic and non-enzymatic isolation methods; reaching from 68.8±11.0% (cutting), 75.4±7.6% (shaking), 78.0±4.2% (collagenase) to 79.0±7.5% (present invention) living cells compared to total cell number (FIG. 9).

Freshly isolated cells derived from enzymatic isolation and according to the invention were seeded in increasing concentration (4, 20, 100, 500, 2500, 12500 cells/well) in a 6-well plate and cultured in proliferation media. After 2 weeks, colony forming capacity of the cells was analyzed by staining the cells with hematoxylin/eosin (FIG. 10a) and calculating the percentage of cells that formed colonies in comparison to total seeded cells. Quantitative analysis revealed a frequency of 1.8±0.52% for cells isolated according to the invention compared to 1.3±0.43% for cells obtained by the enzymatic isolation method (FIG. 10b).

As ATP production is an indicator for energy production of the cells, we analyzed the intra-/extracellular ATP concentration of the adherent cell fraction. Interestingly, the ATP concentration was significantly higher of cells obtained using the present invention (1780±360 nmol/L) compared to the non-enzymatic isolation methods shaking (1237±35 nmol/L) and cutting (1114±69 nmol/L) as well as to the enzymatic isolation method (852±298 nmol/L) (FIG. 11).

Isolated cells derived from all cell isolation methods showed characteristic ASC spindle-shaped cell morphology on day 7 (FIG. 12a).

The proliferation potential of the isolated cells was analyzed over 3 weeks (day 7, 14, 21) by calculating the population doubling level (PDL) (FIG. 12b). Cells isolated according to the invention showed similar PDL compared to the enzymatic isolation method and to the non-enzymatic isolation methods shaking and cutting.

To determine the impact of different isolation methods on the cellular composition of adipose tissue-derived cells we investigated the immunophenotype of freshly isolated and adherent cell fraction derived from the process according to the invention and enzymatic isolation by flow cytometry analysis. While there was no difference in the mesenchymal stem cell marker CD73 (47.7±3.1% vs 46.2±19.9%), CD90 (70.6±7.8% vs 76.0±5.9%) and CD105 (34.5±19.3% vs 32.2±24.3%), (FIGS. 13a, 13b and 13c) analysis of specific subpopulations showed a small decrease of EPC (CD45−/CD31+/CD34+) (15.6±12.1% vs 20.7±1.7%) and pericytic subpopulations (CD45−/CD31−/CD146+) (13.1±11.1% vs 24.8±2.9%) when using the invention compared to enzymatic isolation (FIGS. 13d and 13e). In contrast, the inventive method and device enhanced the number of SA-ASC (CD45−/CD31−/CD146−/CD34+) compared to enzymatic isolation (52.3±4.3% vs 28.9±2.4%) (FIG. 13f).

Regarding the adherent cell immunophenotype there was almost no difference between cells derived according to the invention and by enzymatic isolation in the mesenchymal stem cell marker CD73 (88.4±11.8% vs 92.4±13.9%), CD90 (94.2±9.3% vs 89.4±10.3%), CD105 (89.4±12.3% vs 88.9±20.0%) and the endothelial/pericytic marker CD146 (10.5±13.1% vs 9.5±1.3%). In contrast, cells derived with the invention showed an increase in hematopoietic marker CD45 (5.7±6.0% vs 1.2±1.2%), endothelial marker CD31 (11.8±12.1% vs 5.6±5.8%) and CD34 (8.5±9.9% vs 3.9±4.1%) (FIG. 14a). In consistence to this, the inventive method and device seems to promote the endothelial lineage as there was a clear increase in the EPC subpopulation (CD45−/CD31+/CD34+) (22.8±7.3% vs 0.3±0.1%) after 6 days in culture compared to enzymatic isolation (FIG. 14b). Also the number of pericyte like-cells (CD45−/CD31−/CD146+) was enhanced with the invention (20.3±14.1% vs 8.4±3.9%) (FIG. 14c) and the number of SA-ASC (CD45−/CD31−/CD146−/CD34+) was still increased after 6 days in culture although lower compared to enzymatic isolation (16.0±4.8% vs 23.8±9.1%) (FIG. 14d).

As LDH release in cells is an indicator for cytotoxicity SVF cells derived from enzymatic (collagenase 0.2 U/ml) and non-enzymatic isolation method after employing the invention were normalized to a control using Triton X-100 where 100% of SVF cells died. Cells isolated with the invention expressed significantly lower LDH release (26.6±0.7%) compared to collagenase isolated cells (39.1±2.7%) and control condition Triton X-100 (100%) (FIG. 15).

Adherent SVF derived with the invention, non-enzymatic isolation methods shaking and cutting and enzymatic isolation method (collagenase 0.2 U/ml) were examined by induction with differentiation media for their osteogenic, adipogenic and chondrogenic differentiation potential.

After 3 weeks of incubation with osteogenic media, cells were analyzed for their osteogenic differentiation potential by staining with Alizarin red, which indicates matrix mineralization and calcification, and measuring of intracellular alkaline phosphatase (ALP) activity, which is expressed in active osteoblasts. Alizarin red staining demonstrated less mineralization for cells isolated with the enzymatic isolation method and the non-enzymatic isolation methods shaking and cutting; but strong mineralization after using the invention (FIG. 16a).

These observations were confirmed through quantitative analysis of the Alizarin red staining showing significant higher Alizarin red extinction for cells isolated using the invention (2.6±0.4) compared to the enzymatic isolation method (1.1±0.5) and to the non-enzymatic isolation methods cutting (0.5±0.4) and shaking (1.5±0.9) (FIG. 16b). Similar to Alizarin red staining, ALP activity was significant higher for cells isolated after using the invention (366±248 µmol/L) compared to cells isolated with the enzymatic isolation method (148±59 µmol/L) and non-enzymatic isolation methods shaking (141±70 µmol/L) and cutting (142±108 µmol/L) (FIG. 17).

Adipogenic differentiation potential of the isolated cells was analyzed after 3 weeks of incubation with adipogenic differentiation media by staining with Oil red O, which is an indicator for lipid droplet formation. Oil red O staining demonstrated stronger lipid droplet formation for cells isolated using the invention compared to the enzymatic isolation method and the non-enzymatic isolation methods shaking and cutting (FIG. 18a). Quantitative analysis of the staining confirmed the stronger adipogenic differentiation potential of cells isolated using the invention by showing significant higher Oil red O extinction (0.8±0.2) compared to the enzymatic isolation method (0.4±0.2) and to the non-enzymatic isolation methods cutting (0.4±0.2) and shaking (0.4±0.2) (FIG. 18b).

To analyze chondrogenic differentiation potential, 3D micromass pellets were formed and incubated for 5 weeks in chondrogenic differentiation media. The 3D micromass pellets were investigated every week for their cross section area and after 5 weeks stained with Alcian blue and collagen type II, which are both indicators for chondrogenic differentiation. Histological analysis showed weak or absent Alcian blue and collagen type II staining for cells isolated with the enzymatic isolation method and the non-enzymatic isolation methods shaking and cutting. However, 3D micromass pellets formed by cells isolated using the invention demonstrated intense stainings for Alcian blue and collagen type II (FIG. 19a). Moreover, cells derived with the invention showed a faster growth of 3D micromass pellets as the pellet size was clearly enhanced compared to all other isolation methods increase did not reach statistical significance although the (FIG. 19b).

Freshly isolated cells were examined in 3D fibrin matrices for their vascularization potential. After 2 weeks incubation in expansion media including aprotinin, which prevents fibrin clot degradation, gels were stained with the endothelial marker CD31. The staining demonstrated that cells derived from enzymatic isolation and according to the invention developed a tube-like morphology (FIG. 20) indicating in vitro vasculogenesis.

To isolate cells from adipose tissue, enzymes such as collagenase are used, which is accompanied by high costs, may raise issues with regulatory authorities (see EudraLex, Clinical trial guidelines. 2010 Volume 10; Aarya Hari, S. G., Production of Good Manufacturing Practice Grade Equine Adiposederived Mesenchymal Stem Cells for Therapeutic Use. Journal of Stem Cell Research & Therapy, 2013. 03(05): p. 2157-7633; Sensebe, L., Beyond genetic stability of mesenchymal stromal cells. Cytotherapy, 2013. 15(11): p. 1307-8; EudraLex, Good manufacturing practice (GMP) 2015 Volume 4) and potentially impacts cell efficacy (Busser, H., et al., Isolation of adipose derived stromal cells without enzymatic treatment: expansion, phenotypical and functional characterization. Stem Cells Dev, 2014; Seaman, S. A., et al., Differential Effects of Processing Time and Duration of Collagenase Digestion on Human and Murine Fat Grafts. Plast Reconstr Surg, 2015. 136(2): p. 189e-199e). Alternatively, in order to avoid enzymes, isolation systems using physical forces are available. These systems do not include enzymatic digestion but free cells from the processed adipose tissue by mechanical forces.

The present invention proposes a new closed non-enzymatic method for homogenizing adipose tissue enriched with therapeutic cells for reconstruction, repair and replacement in regenerative medicine. With the assistance of a controllable pump system the collected adipose tissue is on-line transported to special blades/paddles, homogenized and afterwards collected in a container for separation and direct use or cryostorage. Analyses of cells derived with the inventive method and device demonstrated improved cell properties and functionalities.

It is shown that the inventive non-enzymatic method provides adipose tissue enriched with therapeutic cells. These cells exhibit higher intra- and extracellular ATP concentration and differentiate more efficient into the adipogenic, osteogenic and chondrogenic lineage compared to standard enzymatic (collagenase) and non-enzymatic isolation methods (shaking modified from Shah, F. S., et al. 2013 as cited above and Gimble, J. M., et al. 2014 as cited above and cutting method modified from Capurro, S. 2007 as cited above). Although non-enzymatic isolation according to the invention resulted in 3-5 fold higher cell yields than the non-enzymatic isolation methods shaking and cutting, the obtained cell yield was significantly lower compared to enzymatic isolation method. To overcome drawbacks such as inferior cell yield for clinical applications which may require high cell numbers, more tissue material can be used since adipose tissue is abundantly available and the inventive method and device have a high throughput rate of up to 100 ml lipoaspirate per minute. With the shaking method we isolated $2.5 \times 10^6$ cells per 100 ml adipose tissue which is consistent with the published shaking method (Gimble, J. M., et al. 2014 as cited above). Other groups reported incredibly high cell yields of $1.8 \times 10^{12}$ stromal cells "per sample" adipose tissue (Agha-Mohammadi, S., Non-Enzymatic Method for Harvesting Adipose-Derived Stromal Cells and Adipose-Derived Stem Cells from Fat and Lipo-Aspirate. 2013, US 20130034524 A1), unfortunately neither the method nor the sample size nor the identity of the resulting cell population is clearly defined. Similarly, cell yields of about 2-10 million cells/gram adipose tissue were observed with not clearly defined identity (Bright, R., et al., Isolation of stem cells from adipose tissue by ultrasonic cavitation, and methods of use. 2014, WO 2014000031 A1). The cell identity of the yielded cells is of critical importance for their therapeutic potential. The methods for cell quantification used by different working groups differ or are unclear. Among possible impacts on cell numbers are the numbers of erythrocytes within the SVF, which cannot be considered therapeutic cells. Almost all non-enzymatic isolation methods do not use an erythrocyte lysis step to get rid of erythrocytes which are recognized by many cell counter as viable cells (with a cell size of approximately 4 µm). The cell yield analyzed after using the invention represents cells after erythrocyte lysis, which is usually applied during standard enzymatic isolation. We included this step for a proper comparison to a standard enzymatic isolation protocol. Unfortunately, within most of the above mentioned systems no comparison to a standard enzymatic isolation method is described. The cell yield of the non-enzymatic isolation methods used are 10-fold lower than with enzymatic isolation using 0.2 U/ml collagenase. But cells isolated with the invention show a similar proliferation potential and a similar or even higher colony forming potential compared to enzymatically isolated cells. The frequency of stromal progenitors is above the expected >1% cells (Bourin, P., et al., Stromal cells from the adipose tissue-derived stromal vascular fraction and culture expanded adipose tissue-derived stromal/stem cells: a joint statement of the International Federation for Adipose Therapeutics and Science (IFATS) and the International Society for Cellular Therapy (ISCT). Cytotherapy, 2013. 15(6): p. 641-8). However, the present invention brings up cells with 13% reduced LDH release compared to enzymatically isolated cells, which indicates lower cytotoxicity of the isolates. With more than 70% living cells both enzymatic isolation but also isolation with the present invention provide cells lying within the expected viability range (according to the guidelines of IFATS) (Bourin, P., et al. 2013 as cited above).

Interestingly, the inventive method and device provide higher number and variety of specific cell populations with potential therapeutic efficacy such as endothelial progenitor cells, pericyte like-cells and SA-ASC, which should be suitable for distinct cellular therapies. Although there was a slightly reduced number of EPCs and pericyte like-cells in freshly isolated cells after applying the presently proposed method compared to enzymatic isolation, the inventive device seems to protect these subpopulations which were still present after 6 days in culture in a similar quantity. The invention promotes the endothelial lineage as there was a clear increase of 203% in the EPC subpopulation (CD45−/CD31+/CD34+) compared to enzymatic isolation. Also the number of pericyte like-cells (CD45−/CD31−/CD146+) was after 6 days of culture still affected through the inventive method with a 12% increase compared to enzymatic isolation. Similar findings were also shown by Bianchi et al. (Bianchi, F., et al., A new nonenzymatic method and device to obtain a fat tissue derivative highly enriched in pericyte-like elements by mild mechanical forces from human lipoaspirates. Cell Transplant, 2013. 22(11): p. 2063-77) with the non-enzymatic isolation device Lipogems® where expanded cells obtained by outgrowth from the Lipogems clusters expressed a high number of pericyte-like marker (CD146+) and vascular endothelial cells (CD31+; CD34+). In comparison to Bianchi et al., cells isolated with the present invention showed after 6 days in culture still higher endothelial cells and pericyte like-cell numbers. Zimmerlin et al. (Zimmerlin, L., et al., Human adipose stromal vascular cell delivery in a fibrin spray. Cytotherapy, 2013. 15(1): p. 102-8) revealed with Lipivage™ higher amounts of SA-ASC (CD14−/CD33−/CD45−/glycophorin-A−/CD31−/CD146−/CD34+) than we obtained with our method, but lower endothelial progenitor (CD14−/CD33−/CD45−/glycophorin-A−/CD34+/CD31+) and pericyte like-cells (CD14−/CD33−/CD45−/glycophorin-A−/CD31−/CD146+) compared to our method. Gimble et al. isolated with their non-enzymatic method (Gimble, J. M., et al. 2014 as cited above) lower levels of CD34 (endothelial) and CD45 (hematopoietic) expressing cells and higher levels of CD44 (mesenchymal) within the isolated cell population. James et al. could show that pericytes (CD45−, CD146+, CD34−) and adventitial cells (CD45−, CD146−, CD34+) possess strong osteogenic potential in vivo (James A. W., et al. 2012 as cited above). With the present invention we could show that even the microtissue containing a high number of endothelial cells exhibits a substantial increase in osteogenic differentiation potential analyzed by Alizarin red and alkaline phosphatase. Furthermore, these cells possess further a strong adipogenic (Oil red O) and chondrogenic (Alcian blue, collagen type II) differentiation potential and are able to develop tube-like morphology, which is a prerequisite for neovascularization. This means that there are subpopulations which all have the ability to undergo differentiation into the mesodermal lineages. The question is, if the abundance of special populations is important or if more subpopulations are interacting? Nevertheless, application of the present method and device brings out therapeutic cells with high ATP turnover Without the need of enzyme digestion or further tissue processing, the inventive method and device present a safe method with a very high throughput rate resulting in a simple isolation within a short time. This system provides homogenized adipose tissue enriched with therapeutic cells with defined properties for autologous clinical applications.

Discussion of FIG. 22-34

Cell number and viability was determined using DAPI fluorescence staining and quantified in a cell counter (NucleoCounter® NC-200™, Chemometec, Denmark) with integrated fluorescence microscope. Since the heterogeneous cell composition consists also of aggregated cells on remaining extracellular matrix strands the "Viability and Cell Count—Aggregated Cells Assay" protocol was chosen. Each sample was transferred into a Via1-Cassette™, which is coated with DAPI and two measurements were performed: One with cell lysis solution to stain all cell nuclei in the sample and one without lysis solution to stain only non-viable cells.

A defined number of cells (4, 20, 100, 500, 2500, 12500) was seeded in each well of a 6-well plate and were cultured in EGM-2 for 14 days, including one media change at day 7. After 14 days of culture single cells have formed colonies. Cells were fixed with 4% formaldehyde and stained with hematoxylin. Afterwards, the cells were washed with tap water and stained with eosin solution. The percentage of cells that formed visible colonies (in the well with 500 seeded cells) was calculated and compared to the total seeded cells.

The amount of intra-/extracellular ATP is an indicator for energy production of cells. To determine the intra-/extracellular ATP concentration CellTiter-Glo® Luminescent Cell Viability Assay (Promega, Austria) was used and performed according to the manufacturer's instructions. Cells were seeded at a density of $1 \times 10^4$ cells per well in a black 96-well plate (Greiner, Austria) in 100 µl EGM-2 media. After 2 h, 100 µl CellTiter-Glo® Reagent were added to each well and the plate was gently agitated on a shaker for 2 min. Afterwards the plate was incubated for 10 min in the dark. The combination of intracellular and extracellular ATP can be measured since CellTiter-Glo® Reagent includes a cell lysis buffer. The luminescent signal was detected with a luminometer (Tecan, Austria) at an exposure time of 2000 ms and correlated to an ATP standard curve.

Proliferation potential was analyzed by determining the population doubling level (PDL). Freshly isolated cells were seeded at a density of $5 \times 10^5$ cells per T-25 culture flask and cultured in EGM-2 media. Media was changed every 3 to 4 days. When cells had reached a subconfluent state they were passaged and cell number was determined as described above. For further analysis of PDL, ASC were seeded at a density of $5 \times 10^4$ in T-25 culture flasks and cultured until passage 3. Cell number was determined after each passage.

Freshly isolated and adherent cells from day 6 of culture were characterized using the following antibodies CD73-FITC (eBiosciences, Austria), CD90-PE (eBiosciences), CD105-V450 Horizon (BD, Austria), CD45-V500 Horizon (BD), CD31-FITC (eBiosciences), CD34-APC (BD) and CD146-PerCP (R&D, Austria) as well as the combination of CD45, CD31, CD34 and CD146 to analyze specific subpopulations: endothelial progenitor cells (CD45−/CD31+/CD34+), pericyte like-cells (CD45−/CD31−/CD146+), and supra-adventitial ASC (SA-ASC) (CD45−/CD31−/CD146−/CD34+).

For staining, $2.5 \times 10^5$ cells in 50 µL PBS with 1% FCS were incubated with 5 µl primary labeled antibodies at room temperature for 15 min in the dark. Cells were washed with 1.5 ml Cell Wash (BD) and centrifuged for 5 min at 400 g. The supernatant was discarded and the cell pellet resuspended in 300 µL 1×Cell Fix (BD; diluted 1:10 with aqua dest). Samples were stored at 4° C. in the dark until analysis on a FACSAria II (BD). Percentage of marker positive cells was determined, compared to a non-specific isotype control.

For quantification of lactate dehydrogenase (LDH) release cellular supernatants were analyzed using Cytotoxicity Detection Kit (Roche, Austria). Freshly non-enzymatic (obtained using the invention) and enzymatic (collagenase 0.2 U/ml) isolated cells were seeded at a density of $2\times10^4$ in a 96-well plate in 200 µl EGM-2 and incubated for 24 h. Enzymatic isolated cells seeded in 100 µl EGM-2 and 100 µl Triton X-100 were used as control for 100% dead cells. After an incubation of 24 h 100 µl of each supernatant was transferred into a new well and 100 µl Reaction mixture was added for 0.5 h. Absorbance was measured with a luminometer (Tecan, Austria) at 490 nm and after subtraction of a reference value at 650 nm it was normalized to positive control Triton X-100, which lyses the cells.

For osteogenic differentiation, cells were seeded at a density of $2\times10^3$ cells per well in a 24-well plate in EGM-2 media and incubated overnight. On the next day, media was changed to osteogenic differentiation media DMEM-low glucose (Lonza) containing 10% FCS, 2 mM L-glutamine (PAA), 100 U/ml Pen/Strep (Lonza), 10 nM dexamethasone (Sigma), 150 µM ascorbat-2-phosphate (Sigma), 10 mM β-glycerophosphate (StemCell Technologies, Germany) and 10 nM dihydroxy-vitamin D3 (Sigma) or control media consisting of DMEM:F12/L-glutamine (Lonza) with 10% FCS and 100 U/ml Pen/Strep. Media was changed every 3 to 4 days.

After 21 days, osteogenic differentiation was analyzed with Alizarin Red staining and quantification, as well as determination of intracellular alkaline phosphatase (ALP) activity.

For Alizarin Red staining of calcified structures, cells were washed with PBS and fixed for 1 h with 70% ethanol at −20° C. After rinsing the fixed cells with aqua dest, cells were stained with 40 mM Alizarin Red solution (pH 4.2; Merck, Austria) for 15 min. The cells were washed with PBS and representative images were taken under the light microscope. For quantitative analysis of Alizarin Red staining, the supernatant was discarded and the cells were incubated with 500 µl 20% methanol and 10% acidic acid (diluted in aqua dest) for 15 min. After resuspension, the mixture of cells and methanol/acidic acid was transferred to a transparent 96-well plate (100 µl per well). The absorbance was measured at 450 nm with a luminometer.

The second method to analyze osteogenic differentiation is the detection of the activity of intracellular alkaline phosphatase (ALP), which is located on the surface of osteoblast cells and has been shown to be a biochemical indicator of bone maturation, mineralization and bone turnover. First, osteogenic media was discarded and the cells were incubated with 100 µl PBS for 1 h at −20° C. Afterwards, the cells were lysed for 1 h by addition of 100 µl PBS containing 0.5% TritonX-100 (Sigma). For quantitative detection of ALP activity, 100 µl substrate solution (4-nitrophenylphosphate) were added in each well and incubated for 1 h in the dark. Finally, the solution was transferred to a transparent 96-well plate (100 µl per well) and absorbance was measured at 405 nm together with a reference wavelength of 620 nm in a luminometer. By creating a standard curve with known p-nitrophenol concentrations diluted in stop solution (0.5% TritonX-100 diluted in PBS 1:2) and measuring the corresponding absorption, the ALP activity of the samples can be calculated.

For adipogenic differentiation, cells were seeded at a density of $1.4\times10^4$ cells per well in a 24-well plate in EGM-2 media and incubated overnight. On the next day, media was changed to adipogenic differentiation media DMEM-high glucose (Lonza) containing 10% FCS, 2 mM L-glutamine, 100 U/ml Pen/Strep, 1 µM dexamethasone, 0.5 mM 3-isobutyl-1-methylxanthine (IBMX; Sigma), 10 µg/ml insulin (Sigma) and 100 µM indomethacin (Sigma) or control media consisting of DMEM:F12/L-glutamine with 10% FCS and 100 U/ml Pen/Strep. Media was changed every 3 to 4 days.

After 21 days, adipogenic differentiation was analyzed with Oil Red O staining and quantification. An Oil Red O stock solution was prepared by dissolving 0.3 g Oil red O (Sigma) in 100 ml isopropanol (Merck, Germany) at 50-60° C. For the working solution the filtered stock solution was diluted in aqua dest 3:2. After 30 min the working solution was filtered once again immediately before usage. The cells were washed with PBS and fixed with 4% formaldehyde for 1 h. After washing with aqua dest, the cells were rinsed with 70% ethanol for 2 min and stained for 5-15 min with Oil Red O working solution. Then the cells were washed with aqua dest and counterstained for 1-3 min with Mayer's haematoxylin solution. Finally, the cells were washed with tap water and evaluated under the light microscope. For quantitative detection of Oil Red O staining, the supernatant was discarded and 500 µl isopropanol were added in each well. After resuspension, the mixture of cells and isopropanol was transferred to a transparent 96-well plate (100 µl per well). The absorbance was measured at 510 nm with a luminometer.

For chondrogenic differentiation and 3D micromass pellet cultures, $3\times10^5$ ASC were centrifuged in chondrogenic differentiation media (hMSC Chondro BulletKit (Lonza) containing 10 ng/ml BMP-6 (R&D) and 10 ng/ml TGF-ß3 (Lonza) in screw cap micro tubes. The tubes were placed in an incubator at 37° C., 5% CO2, and 95% humidity with slightly open cap for gas exchange. After 2 days the pellets were transferred to 96-well U-bottom plates (Greiner) with fresh media. Media was changed every 2 to 3 days. The 3D micromass pellet cultures incubated over 35 days in chondrogenic differentiation media were measured once a week for their cross section area. After 35 days of differentiation, micromass pellets were fixed in 4% phosphate-buffered formalin overnight for histological analysis. The next day the pellets were washed in 1× PBS and dehydrated in increasing concentrations of alcohol. After rinsing the pellets in xylol and infiltration with paraffin, deparaffinized sections were stained with Alcian blue for 30 min and counterstained for 2 min with Mayer's haematoxylin. For collagen type II staining, sections were treated with pepsin for 10 min at 37° C. (AP-9007 RTU, Thermo Scientific, Austria). Endogenous peroxidase was quenched with freshly prepared 3% H2O2 for 10 min at room temperature, followed by normal horse serum 2.5% (Vector RTU) to block unspecific binding. Sections were incubated 1 h with monoclonal anti-collagen type II (MS-306 P0 Thermo Scientific) at 1:100. After washing with TBS, sections were incubated with the secondary antibody (anti mouse DAKO EnVision+ System HRP labelled Polymer, Dako, Austria) for 30 min and rinsed in TBS again. Bindings were visualized using Nova Red (SK4800 Vector Labs, Austria) for 6 min. Counterstaining was performed with Mayer's haematoxylin for 2 min.

For determination of the vascularization potential of adipose tissue-derived cells a fibrin clot culture was performed according to Holnthoner et al. (Holnthoner, W., et al. 2015 as cited above) $4\times10^5$ cells were mixed with fibrinogen (Baxter, Austria; 2.5 mg/ml) and thrombin (Baxter, 0.2 U/ml) for clot formation and pipetted on coverslips in 12-well plates. Clots were polymerized at 37° C. for 30 min and cultured for 2 weeks in EGM-2 containing aprotinin (Baxter, 100 KIU/ml). Media was changed every 3-4 days. After cultivation clots were fixed with 4% PFA, washed with PBS and incubated with a FITC-conjugated monoclonal mouse anti-human CD31 antibody (BD Biosciences; 1:50 dilution in PBS/1% BSA) for 12 hours in the dark. Clots were again washed with PBS and images were taken on a Zeiss Axiovert 200M fluorescence microscope.

Data are presented as mean±standard deviation and statistical analysis was performed using PRISM6 (GraphPad, San Diego, Calif., USA), one-way ANOVA Tukey's post hoc. Statistical analysis of the pellet size was performed using two-way ANOVA Tukey's post hoc. Flow cytometry and CFU-F assay statistical analysis was performed using unpaired t-test. P values of <0.05 were considered to be significant.

The cell yield of freshly isolated cells was significantly higher after enzymatic isolation with $4.8\pm3.1\times10^7$ cells derived from 100 ml lipoaspirate compared to all non-enzymatic isolation methods (FIG. 22). The method according to the present invention resulted in a cell yield of $7.4\pm2.6\times10^6$ cells, while shaking and cutting method reached lower cell numbers of $1.2\pm0.6\times10^6$ and $2.1\pm1.2\times10^6$, respectively. However, cell viability of freshly isolated cells was similar in all applied enzymatic and non-enzymatic isolation methods; reaching from 68.8±11.0% (cutting), 75.4±7.6% (shaking), 78.0±4.2% (collagenase) to 79.0±7.5% (present invention) living cells compared to total cell number (FIG. 23).

Freshly isolated cells derived from enzymatic isolation and according to the invention were seeded in increasing concentration (4, 20, 100, 500, 2500, 12500 cells/well) in a 6-well plate and cultured in proliferation media. After 2 weeks, colony forming capacity of the cells was analyzed by staining the cells with hematoxylin/eosin (FIG. 24a) and calculating the percentage of cells that formed colonies in comparison to total seeded cells. Quantitative analysis revealed a frequency of 1.8±0.52% for cells isolated according to the invention compared to 1.4±0.43% for cells obtained by the enzymatic isolation method (FIG. 24b).

As ATP production is an indicator for energy production of the cells, we analyzed the intra-/extracellular ATP concentration of the adherent cell fraction. Interestingly, the ATP concentration was significantly higher of cells obtained using the present invention (1780±360 nmol/L) compared to the non-enzymatic isolation methods shaking (1237±35 nmol/L) and cutting (1114±69 nmol/L) as well as to the enzymatic isolation method (852±298 nmol/L) (FIG. 25).

Isolated cells derived from all cell isolation methods showed characteristic ASC spindle-shaped cell morphology on day 7 (FIG. 26a).

The proliferation potential of the isolated cells was analyzed over 3 weeks (day 7, 14, 21) by calculating the population doubling level (PDL) (FIG. 26b). Cells isolated according to the invention showed similar PDL compared to the enzymatic isolation method and to the non-enzymatic isolation methods shaking and cutting.

To determine the impact of different isolation methods on the cellular composition of adipose tissue-derived cells we investigated the immunophenotype of freshly isolated and adherent cell fraction derived from the process according to the invention and enzymatic isolation by flow cytometry analysis. While there was no difference in the mesenchymal stem cell marker CD73 (36.4±24.2% vs 47.7±3.0%), CD90 (64.8±25.6% vs 70.6±7.8%) and CD105 (25.1±24.3% vs 34.4±19.2%), (FIGS. 27a, 27b and 27c) analysis of specific subpopulations showed a small decrease of EPC (CD45−/CD31+/CD34+) (15.6±12.1% vs 20.7±1.7%) and pericytic subpopulations (CD45−/CD31−/CD146+) (13.1±11.1% vs 24.8±2.9%) when using the invention compared to enzymatic isolation (FIGS. 27d and 27e). In contrast, the inventive method and device enhanced the number of SA-ASC (CD45−/CD31−/CD146−/CD34+) compared to enzymatic isolation (38.1±20.4% vs 27.1±3.2%) (FIG. 27f).

Regarding the adherent cell immunophenotype there was almost no difference between cells derived according to the invention and by enzymatic isolation in the mesenchymal stem cell marker CD73 (88.4±11.8% vs 92.4±14.0%), CD90 (94.2±9.3% vs 89.4±10.3%), CD105 (89.4±12.4% vs 88.9±20.0%) and the endothelial/pericytic marker CD146 (10.5±13.1% vs 9.5±1.3%). In contrast, cells derived with the invention showed an increase in hematopoietic marker CD45 (5.7±6.0% vs 1.2±1.2%), endothelial marker CD31 (11.8±12.1% vs 5.6±5.8%) and CD34 (8.5±9.9% vs 3.9±4.1%) (FIG. 28a). In consistence to this, the inventive method and device seems to promote the endothelial lineage as there was a clear increase in the EPC subpopulation (CD45−/CD31+/CD34+) (22.8±7.3% vs 0.3±0.1%) after 6 days in culture compared to enzymatic isolation (FIG. 28b). Also the number of pericyte like-cells (CD45−/CD31−/CD146+) was enhanced with the invention (22.3±14.1% vs 8.4±3.9%) (FIG. 28c) and the number of SA-ASC (CD45−/CD31−/CD146−/CD34+) was still increased after 6 days in culture although lower compared to enzymatic isolation (16.0±4.8% vs 23.8±9.1%) (FIG. 28d).

As LDH release in cells is an indicator for cytotoxicity SVF cells derived from enzymatic (collagenase 0.2 U/ml) and non-enzymatic isolation method after employing the invention were normalized to a control using Triton X-100 where 100% of SVF cells died. Cells isolated with the invention expressed significantly lower LDH release (26.6±0.7%) compared to collagenase isolated cells (39.1±2.7%) and control condition Triton X-100 (100%) (FIG. 29).

Adherent SVF derived with the invention, non-enzymatic isolation methods shaking and cutting and enzymatic isolation method (collagenase 0.2 U/ml) were examined by induction with differentiation media for their osteogenic, adipogenic and chondrogenic differentiation potential.

After 3 weeks of incubation with osteogenic media, cells were analyzed for their osteogenic differentiation potential by staining with Alizarin red, which indicates matrix mineralization and calcification, and measuring of intracellular alkaline phosphatase (ALP) activity, which is expressed in active osteoblasts. Alizarin red staining demonstrated less mineralization for cells isolated with the enzymatic isolation method and the non-enzymatic isolation methods shaking and cutting; but strong mineralization after using the invention (FIG. 30a).

These observations were confirmed through quantitative analysis of the Alizarin red staining showing significant higher Alizarin red extinction for cells isolated using the invention (2.6±0.4) compared to the enzymatic isolation method (1.1±0.5) and to the non-enzymatic isolation methods cutting (0.5±0.4) and shaking (1.5±0.9) (FIG. 30b). Similar to Alizarin red staining, ALP activity was significant higher for cells isolated after using the invention (366±248 μmol/L) compared to cells isolated with the enzymatic isolation method (148±59 μmol/L) and non-enzymatic isolation methods shaking (141±70 μmol/L) and cutting (142±108 μmol/L) (FIG. 31).

Adipogenic differentiation potential of the isolated cells was analyzed after 3 weeks of incubation with adipogenic differentiation media by staining with Oil red O, which is an indicator for lipid droplet formation. Oil red O staining demonstrated stronger lipid droplet formation for cells isolated using the invention compared to the enzymatic isolation method and the non-enzymatic isolation methods shaking and cutting (FIG. 32a). Quantitative analysis of the staining confirmed the stronger adipogenic differentiation potential of cells isolated using the invention by showing significant higher Oil red O extinction (0.8±0.2) compared to the enzymatic isolation method (0.4±0.2) and to the non-enzymatic isolation methods cutting (0.4±0.2) and shaking (0.4±0.2) (FIG. 32b).

To analyze chondrogenic differentiation potential, 3D micromass pellets were formed and incubated for 5 weeks in chondrogenic differentiation media. The 3D micromass pellets were investigated every week for their cross section area and after 5 weeks stained with Alcian blue and collagen type II, which are both indicators for chondrogenic differentiation. Histological analysis showed weak or absent Alcian blue and collagen type II staining for cells isolated with the enzymatic isolation method and the non-enzymatic isolation methods shaking and cutting. However, 3D micromass pellets formed by cells isolated using the invention demonstrated intense stainings for Alcian blue and collagen type II (FIG. 33a). Moreover, cells derived with the invention showed a faster growth of 3D micromass pellets as the pellet size was significantly enhanced compared to all other isolation methods starting from 21 days of differentiation with 1.9±1.1 mm$^2$ compared to shaking 0.8±0.2 mm$^2$ and cutting 0.4±0.1 mm$^2$. On day 28 pellet size of invention was 2.4±1.3 mm$^2$ compared to shaking 1.0±0.2 mm$^2$, cutting 0.3±0.1 mm$^2$ and enzymatic isolation method 0.9±0.3 mm$^2$. On day 35 the pellets represent a size of 2.7±1.4 mm$^2$ for invention compared to shaking 1.2±0.3 mm$^2$, cutting 0.2±0.1 mm$^2$ and enzymatic isolation method 1.1±0.5 mm$^2$ (FIG. 33b).

Freshly isolated cells were examined in 3D fibrin matrices for their vascularization potential. After 2 weeks incubation in expansion media including aprotinin, which prevents fibrin clot degradation, gels were stained with the endothelial marker CD31. The staining demonstrated that cells derived from enzymatic isolation and according to the invention developed a tube-like morphology (FIG. 34) indicating in vitro vasculogenesis.

Discussion of FIG. 35-43

The cell yield of freshly isolated cells was significantly higher after enzymatic isolation with 5.3±3.6×10$^7$ cells derived from 100 ml lipoaspirate compared to present invention with 7.5±4.9×10$^6$ cells and variation 3 of the invention with 1.4±1.5×10$^7$ cells (FIG. 35). The method according to the variation 1, 2 and 4 of invention resulted in a cell yield of 2.4±2.1×10$^7$ cells, 1.8±1.2×10$^7$ cells and 1.8±1.6×10$^7$ cells. However, cell viability of freshly isolated cells was similar in all applied enzymatic and non-enzymatic isolation methods; reaching from 79.0±2.5% (collagenase), 85.4±3.8% (present invention), 90.6±4.9 (variation 1 of present invention), 85.6±10.6 (variation 2 of present invention), 78.1±10.4 (variation 3 of present invention) to 82.7±15.5% (variation 4 of present invention) living cells compared to total cell number (FIG. 36).

Freshly isolated cells derived from enzymatic isolation and according to the invention were seeded in increasing concentration (4, 20, 100, 500, 2500, 12500 cells/well) in a 6-well plate and cultured in proliferation media. After 2 weeks, colony forming capacity of the cells was analyzed by staining the cells with hematoxylin/eosin and calculating the percentage of cells that formed colonies in comparison to total seeded cells. Quantitative analysis revealed a frequency of 2.2±0.8% for cells isolated according to the invention compared to 1.7±0.7% for cells obtained by the enzymatic isolation method (FIG. 37).

To determine the impact of different isolation methods on the cellular composition of adipose tissue-derived cells we investigated the immunophenotype of freshly isolated cells derived from the process according to the invention and enzymatic isolation by flow cytometry analysis. The analysis of specific subpopulations showed a small decrease of EPC (CD45-/CD31+/CD34+) (11.8±12.3% vs 16.7±7.2%) and pericytic subpopulations (CD45-/CD31-/CD146+) (10.4±10.7% vs 20.7±7.6%) when using the invention compared to enzymatic isolation (FIGS. 38a and 38b). In contrast, the inventive method and device enhanced the number of SA-ASC (CD45-/CD31-/CD146-/CD34+) compared to enzymatic isolation (35.0±18.4% vs 27.2±2.8%) (FIG. 38c).

Adherent SVF derived with the invention and enzymatic isolation method (collagenase 0.2 U/ml) were examined by induction with differentiation media for their osteogenic and adipogenic differentiation potential.

After 3 weeks of incubation with osteogenic media, cells were analyzed for their osteogenic differentiation potential by staining with Alizarin red, which indicates matrix mineralization and calcification, and measuring of intracellular alkaline phosphatase (ALP) activity, which is expressed in active osteoblasts. The quantitative analysis of the Alizarin red staining shows significant higher Alizarin red extinction for cells isolated using the invention (2.6±0.4) compared to the enzymatic isolation method (1.2±0.6) (FIG. 39). Similar to Alizarin red staining, ALP activity was higher for cells isolated after using the invention (366±248 µmol/L) compared to cells isolated with the enzymatic isolation method (229±122 µmol/L) (FIG. 40).

Adipogenic differentiation potential of the isolated cells was analyzed after 3 weeks of incubation with adipogenic differentiation media by staining with Oil red O, which is an indicator for lipid droplet formation. The quantitative analysis of the staining demonstrated the stronger adipogenic differentiation potential of cells isolated using the invention by showing significant higher Oil red O extinction (0.8±0.1) compared to the enzymatic isolation method (0.6±0.1) (FIG. 41).

The cell yield of freshly isolated cells was slightly enhanced after the invention method with 7.5±4.9×10$^6$ cells derived from 100 ml lipoaspirate compared to 1, 3, 6 and 11 rows of blades of the invention method which reached lower cell numbers of 1.6±1.7×10$^6$, 2.2±0.8×10$^6$, 2.1±0.3×10$^6$ and 1.7±0.8×10$^6$, respectively (FIGS. 42a and 42b).

However, cell viability of freshly isolated cells showed no significance in all applied non-enzymatic isolation methods with 77.1±7.7% (1 row of blades of the invention), 75.3±5.7% (3 rows of blades of the invention), 72.9±0.9% (6 rows of blades of the invention), 78.4±8.8% (11 rows of blades of the invention) to 85.4±3.8% (present invention) living cells compared to total cell number (FIGS. 43a and 43b).

To isolate cells from adipose tissue, enzymes such as collagenase are used, which is accompanied by high costs, may raise issues with regulatory authorities (see EudraLex, Clinical trial guidelines. 2010 Volume 10; Aarya Hari, S. G., Production of Good Manufacturing Practice Grade Equine Adiposederived Mesenchymal Stem Cells for Therapeutic Use. Journal of Stem Cell Research & Therapy, 2013. 03(05): p. 2157-7633; Sensebe, L., Beyond genetic stability of mesenchymal stromal cells. Cytotherapy, 2013. 15(11): p. 1307-8; EudraLex, Good manufacturing practice (GMP) 2015 Volume 4) and potentially impacts cell efficacy (Busser, H., et al., Isolation of adipose derived stromal cells without enzymatic treatment: expansion, phenotypical and functional characterization. Stem Cells Dev, 2014; Seaman, S. A., et al., Differential Effects of Processing Time and Duration of Collagenase Digestion on Human and Murine Fat Grafts. Plast Reconstr Surg, 2015. 136(2): p. 189e-199e). Alternatively, in order to avoid enzymes, isolation systems using physical forces are available. These systems do not include enzymatic digestion but free cells from the processed adipose tissue by mechanical forces.

The present invention proposes a new closed non-enzymatic method for homogenizing adipose tissue enriched with therapeutic cells for reconstruction, repair and replacement in regenerative medicine. With the assistance of a controllable pump system the collected adipose tissue is on-line transported to special blades/paddles, homogenized and afterwards collected in a container for separation and direct use or cryostorage. Analyses of cells derived with the inventive method and device demonstrated improved cell properties and functionalities.

It is shown that the inventive non-enzymatic method provides adipose tissue enriched with therapeutic cells. These cells exhibit higher intra- and extracellular ATP concentration and differentiate more efficient into the adipogenic, osteogenic and chondrogenic lineage compared to standard enzymatic (collagenase) and non-enzymatic isolation methods (shaking modified from Shah, F. S., et al. 2013 as cited above and Gimble, J. M., et al. 2014 as cited above and cutting method modified from Capurro, S. 2007 as cited above). Although non-enzymatic isolation according to the invention resulted in 4-6 fold higher cell yields than the non-enzymatic isolation methods shaking and cutting, the obtained cell yield was significantly lower compared to enzymatic isolation method. To overcome drawbacks such as inferior cell yield for clinical applications which may require high cell numbers, more tissue material can be used since adipose tissue is abundantly available and the inventive method and device have a high throughput rate of up to 100 ml lipoaspirate per minute. With the shaking method we isolated $2.5 \times 10^6$ cells per 100 ml adipose tissue which is consistent with the published shaking method (Gimble, J. M., et al. 2014 as cited above). Other groups reported incredibly high cell yields of $1.8 \times 10^{12}$ stromal cells "per sample" adipose tissue (Agha-Mohammadi, S., Non-Enzymatic Method for Harvesting Adipose-Derived Stromal Cells and Adipose-Derived Stem Cells from Fat and Lipo-Aspirate. 2013, US 20130034524 A1), unfortunately neither the method nor the sample size nor the identity of the resulting cell population is clearly defined. Similarly, cell yields of about 2-10 million cells/gram adipose tissue were observed with not clearly defined identity (Bright, R., et al., Isolation of stem cells from adipose tissue by ultrasonic cavitation, and methods of use. 2014, WO 2014000031 A1). The cell identity of the yielded cells is of critical importance for their therapeutic potential. The methods for cell quantification used by different working groups differ or are unclear. Among possible impacts on cell numbers are the numbers of erythrocytes within the SVF, which cannot be considered therapeutic cells. Before analyzing the cell yield, almost all non-enzymatic isolation methods do not use an erythrocyte lysis step to get rid of erythrocytes which are recognized by many standard cell counter as viable cells (with a cell size of approximately 4 µm). Our specialized cell counter does not include erythrocytes since it only recognizes nucleated cells. Moreover, aggregated cells within the SVF can be precisely counted due to a 2-step protocol comprising of a lysis step, where all cells are counted and a second step, where only dead cells are counted. Our cell yield analyzed after using the invention represents cells after erythrocyte lysis, which is usually applied during standard enzymatic isolation. We included this step for a proper comparison to a standard enzymatic isolation protocol, but it is not necessary for clinical use. Unfortunately, within most of the above mentioned articles no comparison to a standard enzymatic isolation method is described. The cell yield of the invention method is 7-fold lower than with enzymatic isolation while the optimized variants (i.e. variants 1-4 discussed above) of the inventive method provides cell yields 3-fold higher than the inventive method. Cells isolated with the invention show a similar proliferation potential and a similar or even higher colony forming potential compared to enzymatically isolated cells. The frequency of stromal progenitors is above the expected >1% cells (Bourin, P., et al., Stromal cells from the adipose tissue-derived stromal vascular fraction and culture expanded adipose tissue-derived stromal/stem cells: a joint statement of the International Federation for Adipose Therapeutics and Science (IFATS) and the International Society for Cellular Therapy (ISCT). Cytotherapy, 2013. 15(6): p. 641-8). With more than 78% living cells both enzymatic isolation but also isolation with the present invention provide cells lying within the expected viability range (according to the guidelines of IFATS) (Bourin, P., et al. 2013 as cited above).

Interestingly, the inventive method and device provide higher number and variety of specific cell populations with potential therapeutic efficacy such as endothelial progenitor cells, pericyte like-cells and SA-ASC, which should be suitable for distinct cellular therapies. Although there was a slightly reduced number of EPCs and pericyte like-cells in freshly isolated cells after applying the presently proposed method compared to enzymatic isolation, the inventive device seems to protect these subpopulations as their number has duplicated after 6 days in culture. The invention promotes the endothelial lineage as there was a clear increase of 23% in the EPC subpopulation (CD45−/CD31+/CD34+) compared to enzymatic isolation. Also the number of pericyte like-cells (CD45−/CD31−/CD146+) was after 6 days of culture still affected through the inventive method with a 14% increase compared to enzymatic isolation. Similar findings were also shown by Bianchi et al. (Bianchi, F., et al., A new nonenzymatic method and device to obtain a fat tissue derivative highly enriched in pericyte-like elements by mild mechanical forces from human lipoaspirates. Cell Transplant, 2013. 22(11): p. 2063-77) with the non-enzymatic isolation device Lipogems® where expanded cells obtained by outgrowth from the Lipogems clusters expressed a high number of pericyte-like marker (CD146+) and vascular endothelial cells (CD31+; CD34+). In comparison to Bianchi et al., cells isolated with the present invention showed after 6 days in culture still higher endothelial progenitor cells and pericyte like-cell numbers. Zimmerlin et al. (Zimmerlin, L., et al., Human adipose stromal vascular cell delivery in a fibrin spray. Cytotherapy, 2013. 15(1): p. 102-8) revealed with Lipivage™ higher amounts of SA-ASC (CD14−/CD33−/CD45−/glycophorin-A−/CD31−/CD146−/CD34+) than we obtained with our method, but lower endothelial progenitor (CD14−/CD33−/CD45−/glycophorin-A−/CD34+/CD31+) and pericyte like-cells (CD14−/CD33−/CD45−/glycophorin-A−/CD31−/CD146+) compared to our method. Gimble et al. isolated with their non-enzymatic method (Gimble, J. M., et al. 2014 as cited above) lower levels of CD34 (endothelial) and CD45 (hematopoietic) expressing cells and higher levels of CD44 (mesenchymal) within the isolated cell population. James et al. could show that pericytes (CD45−, CD146+, CD34−) and adventitial cells (CD45−, CD146−, CD34+) possess strong osteogenic potential in vivo (James A. W., et al. 2012 as cited above). With the present invention we could show that a high number of endothelial progenitor cells exhibits a substantial increase in osteogenic differentiation potential analyzed by Alizarin red and alkaline phosphatase. Furthermore, these cells possess further a strong adipogenic (Oil red O) and chondrogenic (Alcian blue, collagen type II) differentiation potential and are able to develop tube-like morphology, which is a prerequisite for neovascularization. This means that there are subpopulations which all have the ability to undergo differentiation into the mesodermal lineages. The question is, if the abundance of special populations is important or if more subpopulations are interacting?

Without the need of enzyme digestion or further tissue processing, the inventive method and device present a safe method with a very high throughput rate resulting in a simple isolation within a short time. This system provides homogenized adipose tissue enriched with therapeutic cells with defined properties for potential autologous clinical applications.

The invention claimed is:

1. A milling device for preparing therapeutic cells from adipose tissue, the milling device comprising:
    a casing having an inlet and an outlet and defining an operating volume;
    a rotor received within the operating volume and pivotable with respect to the casing around an axis of rotation;
    the rotor comprising at least eight rows of blades in a spaced arrangement with respect to the axis of rotation of the rotor; and
    the inlet and the outlet being arranged at opposite ends of the rotor close to a first and last row of the blades respectively in a direction of flow;
    wherein the rotor is connected to a drive by a magnetic coupling;
    wherein at least a section of the operating volume has a tapered shape with a cross-section decreasing in a direction from the inlet to the outlet; and
    wherein radially outer ends of the longest blades arranged in the section of the operating volume having a tapered shape are essentially flush with an inner wall of the casing.

2. Milling device according to claim 1, wherein:
    the rotor comprises between 20 and 80 rows of blades.

3. Milling device according to claim 1, wherein:
    at least eight of the rows of blades each comprise two, three, or four blades arranged circumferentially with respect to the axis of rotation of the rotor.

4. Milling device according to claim 1, wherein:
    at least one of the blades comprises two or more radially spaced teeth extending parallel to the axis of rotation.

5. Device according to claim 1, wherein:
    the casing is formed from one or more components connected to each other in a fixed arrangement.

6. Milling device according to claim 1, wherein:
    the milling device is provided as a milling cartridge.

7. A processing device for preparing therapeutic cells from adipose tissue, said processing device comprising:
    at least one milling device according to claim 1; and
    a drive connected to the rotor of the milling device via a driveshaft, and a drive being formed by a motor.

8. Processing device according to claim 7, wherein:
    the milling device is formed by a milling cartridge that is provided as an expendable part of the processing device.

9. A set for liposuction applications, said set comprising:
    a milling device according to claim 1; and
    a cannula that is connected to an inlet of the milling device by tubing that accommodates also a roller pump.

10. A continuous non-enzymatic method for preparing therapeutic cells from adipose tissue comprising:
    (a) continuously feeding the adipose tissue to a milling device, said milling device comprising:
        a casing having an inlet and an outlet and defining an operating volume; and
        a rotor received within the operating volume and pivotable with respect to the casing around an axis of rotation;
        the rotor comprising at least eight rows of blades in a spaced arrangement with respect to the axis of rotation of the rotor;
        the inlet and the outlet being arranged at opposite ends of the rotor close to a first and last row of blades respectively in a direction of flow;
        the rotor being connected to a drive by a magnetic coupling;
        at least a section of the operating volume having a tapered shape with a cross-section decreasing in a direction from the inlet to the outlet;
        radially outer ends of the longest blades arranged in the section of the operating volume having; a tapered shape being essentially flush with an inner wall of the casing;
    (b) continuous controlled processing the adipose tissue inside the milling device by mechanically separating the cells or cell aggregates from adipose tissue moving through the milling device by means of a multiplicity of blades, the blades being arranged in a spaced arrangement with respect to the overall direction of flow and the blades moving about an axis of rotation, the axis of rotation being provided essentially parallel to said overall direction of flow;
    (c) continuously withdrawing processed tissue comprising the separated cells from the milling device.

11. Method according to claim 10, wherein:
    the flow rate through the miffing device in operation is at least 100 ml/min.

12. Method according to claim 10, wherein:
    the flow rate through the milling device in Operation is at least 200 ml/min.

13. Method according to claim 10, further comprising:
    controlling the speed of rotation to a predefined constant speed.

14. Method according to claim 13, wherein:
    the constant speed is between 700-1100 rpm.

15. Method according to claim 10, further comprising:
    continuously withdrawing the processed tissue comprising the cell aggregates separated cells from the milling device by applying a suction to an outlet of the milling device and/or by applying a pressure to an inlet of the milling device.

16. Method according to claim 10, wherein:
    the rotor comprises between 20 and 80 rows of blades.

17. Method according to claim 10, wherein:
    at least eight of the rows of blades each comprise two, three, or four blades arranged circumferentially with respect to the axis of rotation of the rotor.

18. Method according to claim 10, wherein:
at least one of the blades comprises two or more radially spaced teeth extending parallel to the axis of rotation.
19. Method according to claim 10, wherein:
the casing is formed from one or more components connected to each other in a fixed arrangement.
20. Method according to claim 10, wherein:
the milling device is provided as a milling cartridge.

* * * * *